(12) United States Patent
Baik et al.

(10) Patent No.: US 12,258,597 B2
(45) Date of Patent: Mar. 25, 2025

(54) METHODS AND COMPOSITIONS FOR THERAPEUTIC PROTEIN DELIVERY

(71) Applicant: Regeneron Pharmaceuticals, Inc., Tarrytown, NY (US)

(72) Inventors: Andrew Baik, Scarsdale, NY (US); Katherine Cygnar, New York, NY (US); Maria Praggastis, Cortlandt Manor, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1142 days.

(21) Appl. No.: 16/968,452

(22) PCT Filed: Feb. 7, 2019

(86) PCT No.: PCT/US2019/017116
§ 371 (c)(1),
(2) Date: Aug. 7, 2020

(87) PCT Pub. No.: WO2019/157224
PCT Pub. Date: Aug. 15, 2019

(65) Prior Publication Data
US 2020/0399623 A1 Dec. 24, 2020

Related U.S. Application Data

(60) Provisional application No. 62/777,683, filed on Dec. 10, 2018, provisional application No. 62/627,721, filed on Feb. 7, 2018.

(51) Int. Cl.
*C12N 9/26* (2006.01)
*A61K 39/00* (2006.01)
(Continued)

(52) U.S. Cl.
CPC .......... *C12N 9/2408* (2013.01); *A61K 48/005* (2013.01); *A61P 3/00* (2018.01);
(Continued)

(58) Field of Classification Search
CPC combination set(s) only.
See application file for complete search history.

(56) References Cited

U.S. PATENT DOCUMENTS 4,444,878 A 4/1984 Paulus
5,030,717 A 7/1991 Tramontano et al.
(Continued)

FOREIGN PATENT DOCUMENTS

EP 1716232 B1 4/2010
EP 1587923 B1 8/2011
(Continued)

OTHER PUBLICATIONS

Kishnani, P.S. (2015). Challenges of Enzyme Replacement Therapy: Poor Tissue Distribution in Lysosomal Diseases Using Pompe Disease as a Model. In: Rosenberg, A., Demeule, B. (eds) Biobetters. AAPS Advances in the Pharmaceutical Sciences Series, vol. 19. Springer, New York, NY. (Year: 2015).*
(Continued)

*Primary Examiner* — Adam Weidner
*Assistant Examiner* — Laura Ann Essex
(74) *Attorney, Agent, or Firm* — Alston & Bird LLP

(57) ABSTRACT

Compositions and methods for delivering a therapeutic protein to the central nervous system (CNS), in order to treat diseases and disorders that impair the CNS, such as treating lysosomal storage diseases are disclosed. Therapeutic proteins delivered via a therapeutically effective amount of a nucleotide composition encoding the therapeutic protein
(Continued)

Figure 1A:
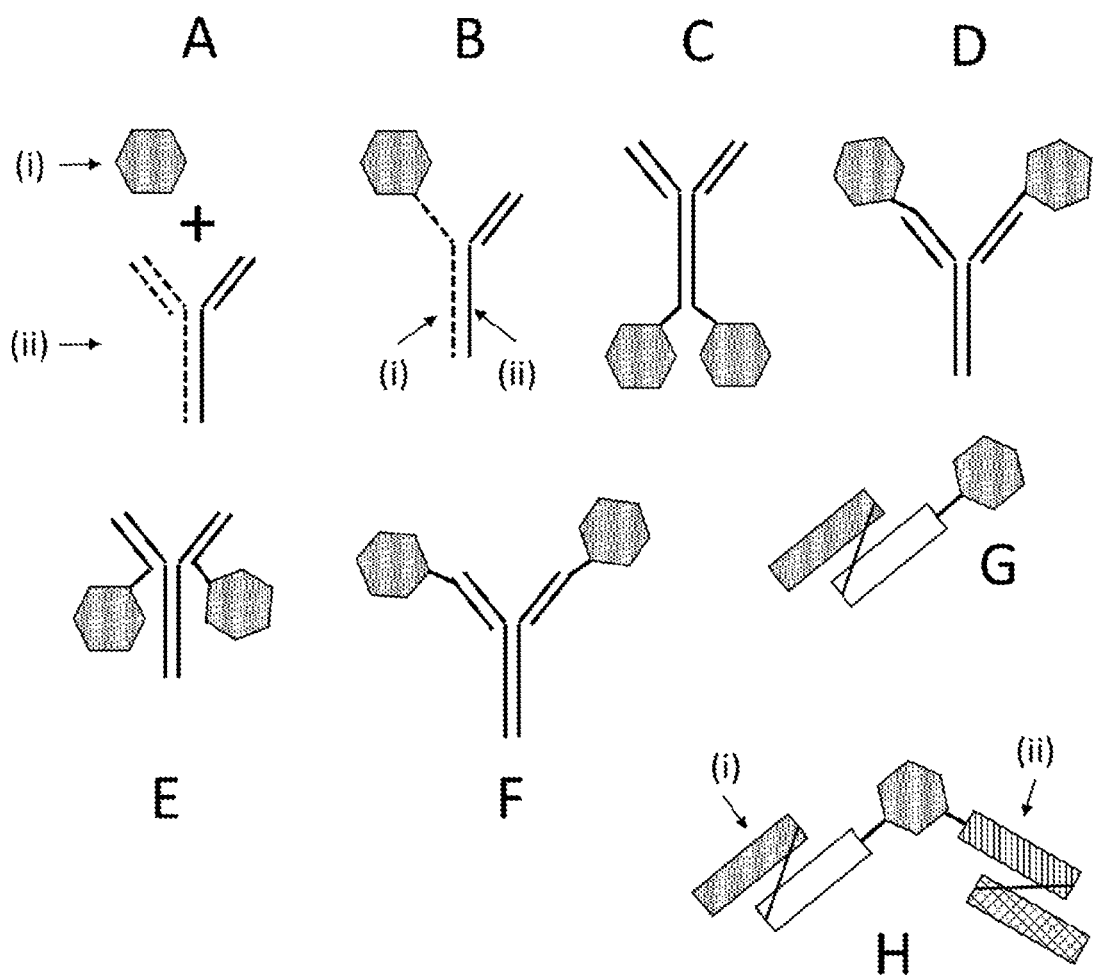

conjugated to a cell surface receptor-binding protein that crosses the blood brain barrier (BBB) are provided.

23 Claims, 28 Drawing Sheets

Specification includes a Sequence Listing.

(51) Int. Cl.
 *A61K 48/00* (2006.01)
 *A61P 3/00* (2006.01)
 *C07K 16/28* (2006.01)

(52) U.S. Cl.
 CPC ...... *C07K 16/2881* (2013.01); *C07K 16/2896* (2013.01); *C12Y 302/0102* (2013.01); *A61K 2039/505* (2013.01); *C07K 2317/622* (2013.01); *C07K 2319/33* (2013.01); *C12N 2750/14143* (2013.01)

(56) References Cited

U.S. PATENT DOCUMENTS

| | | | |
|---|---|---|---|
| 5,126,258 A | 6/1992 | Lerner et al. | |
| 5,156,965 A | 10/1992 | Schochetman et al. | |
| 5,229,272 A | 7/1993 | Paul et al. | |
| 5,436,153 A | 7/1995 | Sprecher et al. | |
| 5,441,931 A | 8/1995 | Sprecher et al. | |
| 5,585,108 A | 12/1996 | Ruddy et al. | |
| 5,602,021 A | 2/1997 | Davis et al. | |
| 5,677,146 A | 10/1997 | Sprecher et al. | |
| 5,731,168 A | 3/1998 | Carter et al. | |
| 5,858,351 A | 1/1999 | Podsakoff et al. | |
| 5,935,854 A | 8/1999 | Sprecher et al. | |
| 5,962,313 A | 10/1999 | Podsakoff et al. | |
| 6,265,389 B1 | 7/2001 | Burke | |
| 6,335,011 B1 | 1/2002 | Podsakoff et al. | |
| 6,372,205 B1 | 4/2002 | Duncan et al. | |
| 6,387,674 B1 | 5/2002 | Trasciatti et al. | |
| 6,479,265 B1 | 11/2002 | Napper et al. | |
| 6,555,525 B2 | 4/2003 | Burke | |
| 6,610,290 B2 | 8/2003 | Podsakoff et al. | |
| 6,703,488 B1 | 3/2004 | Burton et al. | |
| 6,855,804 B2 | 2/2005 | Paul et al. | |
| 7,041,298 B2 | 5/2006 | Deshaies et al. | |
| 7,105,348 B2 | 9/2006 | Murphy et al. | |
| 7,223,556 B1 | 5/2007 | Zhou et al. | |
| 7,335,504 B2 | 2/2008 | Haupts et al. | |
| 7,371,539 B2 | 5/2008 | Church et al. | |
| 7,431,923 B2 | 10/2008 | Young et al. | |
| 7,442,777 B2 | 10/2008 | Young et al. | |
| 7,560,424 B2 | 7/2009 | LeBowitz et al. | |
| 7,704,492 B2 | 4/2010 | Podsakoff et al. | |
| 7,785,856 B2 | 8/2010 | LeBowitz et al. | |
| 7,858,367 B2 | 12/2010 | Amalfitano et al. | |
| 8,048,991 B2 | 11/2011 | Lundgren-Åkerlund | |
| 8,257,745 B2 | 9/2012 | Ketelson et al. | |
| 8,278,036 B2 | 10/2012 | Kariko et al. | |
| 8,563,255 B2 | 10/2013 | Lundgren-Åkerlund | |
| 8,618,264 B2 | 12/2013 | Cunningham et al. | |
| 8,642,835 B2 | 2/2014 | Macdonald et al. | |
| 8,679,478 B2 | 3/2014 | Koeberl | |
| 8,785,168 B2 | 7/2014 | LeBowitz et al. | |
| 8,883,979 B2 | 11/2014 | Ma et al. | |
| 8,974,791 B2 | 3/2015 | Pardridge et al. | |
| 9,023,357 B2 | 5/2015 | Ma et al. | |
| 9,186,420 B2 | 11/2015 | Koeberl | |
| 9,241,989 B2 | 1/2016 | Otto et al. | |
| 9,302,015 B2 | 4/2016 | Papadopoulos et al. | |
| 9,315,790 B2 | 4/2016 | Sakuraba et al. | |
| 9,353,186 B2 | 5/2016 | Freiberg et al. | |
| 9,453,241 B2 | 9/2016 | Pan | |
| 9,545,450 B2 | 1/2017 | Do | |
| 9,545,451 B2 | 1/2017 | Papadopoulos et al. | |
| 9,611,323 B2 | 4/2017 | Dennis et al. | |
| 9,622,459 B2 | 4/2017 | Macdonald et al. | |
| 9,629,801 B2 | 4/2017 | Shusta et al. | |
| 9,649,374 B2 | 5/2017 | Otto et al. | |
| 9,688,764 B2 | 6/2017 | Papadopoulos et al. | |
| 9,708,406 B2 | 7/2017 | Zhang et al. | |
| 9,738,717 B2 | 8/2017 | Azorsa | |
| 9,777,063 B2 | 10/2017 | Freiberg et al. | |
| 9,849,195 B2 | 12/2017 | Davidson | |
| 9,873,868 B2 | 1/2018 | Koeberl et al. | |
| 10,017,581 B2 | 7/2018 | Armstrong et al. | |
| 10,087,253 B2 | 10/2018 | Lundgren-Åkerlund | |
| 10,098,905 B2 | 10/2018 | Koeberl | |
| 10,106,616 B2 | 10/2018 | Papadopoulos et al. | |
| 10,293,000 B2 | 5/2019 | Rebar | |
| 10,512,676 B2 | 12/2019 | Char et al. | |
| 10,556,015 B2 | 2/2020 | Zhang et al. | |
| 10,759,864 B2 | 9/2020 | Sonoda et al. | |
| 10,857,212 B2 | 12/2020 | Do et al. | |
| 10,869,906 B2 | 12/2020 | Kishnani et al. | |
| 10,912,804 B2 | 2/2021 | Byrne et al. | |
| 11,129,903 B2 | 9/2021 | Andreev et al. | |
| 11,191,844 B2 | 12/2021 | Andreev et al. | |
| 11,208,458 B2 | 12/2021 | Baik et al. | |
| 11,352,446 B2 | 6/2022 | Cygnar et al. | |
| 11,578,135 B2 | 2/2023 | Papadopoulos et al. | |
| 2003/0219415 A1 | 11/2003 | Podsakoff et al. | |
| 2004/0204379 A1 | 10/2004 | Cheng et al. | |
| 2004/0248262 A1 | 12/2004 | Koeberl et al. | |
| 2004/0258666 A1 | 12/2004 | Passini et al. | |
| 2005/0142141 A1 | 6/2005 | Pardridge et al. | |
| 2005/0220766 A1 | 10/2005 | Amalfitano et al. | |
| 2005/0244400 A1 | 11/2005 | LeBowitz et al. | |
| 2006/0078542 A1 | 4/2006 | Mah et al. | |
| 2006/0099184 A1 | 5/2006 | Podsakoff et al. | |
| 2006/0171926 A1 | 8/2006 | Passini et al. | |
| 2006/0210474 A1 | 9/2006 | Young et al. | |
| 2007/0280945 A1 | 12/2007 | Stevens et al. | |
| 2008/0044408 A1 | 2/2008 | Young et al. | |
| 2008/0069803 A1 | 3/2008 | Podsakoff et al. | |
| 2008/0089891 A1 | 4/2008 | Hahn et al. | |
| 2008/0269149 A1 | 10/2008 | Bowles et al. | |
| 2008/0279945 A1 | 11/2008 | Mah et al. | |
| 2009/0117091 A1 | 5/2009 | LeBowitz et al. | |
| 2009/0155262 A1 | 6/2009 | Young et al. | |
| 2009/0191178 A1 | 7/2009 | Zankel et al. | |
| 2010/0183577 A1 | 7/2010 | Stern et al. | |
| 2010/0221225 A1 | 9/2010 | Byrne et al. | |
| 2010/0331527 A1 | 12/2010 | Davis et al. | |
| 2011/0184049 A1 | 7/2011 | Chuah et al. | |
| 2011/0223147 A1 | 9/2011 | Lebowitz et al. | |
| 2011/0223176 A1 | 9/2011 | Barlow et al. | |
| 2012/0034625 A1 | 2/2012 | Lundgren-Åkerlund | |
| 2012/0093794 A1 | 4/2012 | LeBowitz et al. | |
| 2012/0183502 A1 | 7/2012 | Meeker et al. | |
| 2012/0228565 A1 | 9/2012 | Adams et al. | |
| 2012/0265001 A1 | 10/2012 | Asmatulu et al. | |
| 2012/0283503 A1 | 11/2012 | Ostrovska et al. | |
| 2012/0315276 A1 | 12/2012 | Otto et al. | |
| 2012/0322861 A1 | 12/2012 | Byrne et al. | |
| 2013/0022606 A1 | 1/2013 | Otto et al. | |
| 2013/0129739 A1 | 5/2013 | Otto et al. | |
| 2013/0171147 A1 | 7/2013 | Otto et al. | |
| 2013/0243775 A1 | 9/2013 | Papadopoulos et al. | |
| 2013/0259833 A1 | 10/2013 | Pan | |
| 2013/0267473 A1 | 10/2013 | Piens et al. | |
| 2013/0272968 A1 | 10/2013 | Otto et al. | |
| 2014/0065158 A1 | 3/2014 | Ma et al. | |
| 2014/0079711 A1 | 3/2014 | Cunningham et al. | |
| 2014/0099716 A1 | 4/2014 | Lundgren-Åkerlund | |
| 2014/0141003 A1 | 5/2014 | Freiberg et al. | |
| 2014/0186326 A1 | 7/2014 | Canfield et al. | |
| 2014/0271659 A1 | 9/2014 | Ma et al. | |
| 2014/0356366 A1 | 12/2014 | Cheong et al. | |
| 2015/0056221 A1 | 2/2015 | Papadopoulos et al. | |
| 2015/0093393 A1 | 4/2015 | Ma et al. | |
| 2015/0110791 A1 | 4/2015 | Zhang et al. | |
| 2015/0196663 A1 | 7/2015 | Shusta et al. | |
| 2015/0196671 A1 | 7/2015 | Byrne et al. | |

(56) References Cited

U.S. PATENT DOCUMENTS

| | | |
|---|---|---|
| 2015/0252116 A1 | 9/2015 | Ma et al. |
| 2015/0322149 A1 | 11/2015 | Bohrmann et al. |
| 2016/0002342 A1 | 1/2016 | Ma et al. |
| 2016/0089451 A1 | 3/2016 | Armstrong |
| 2016/0108133 A1 | 4/2016 | Armstrong et al. |
| 2016/0115229 A1 | 4/2016 | Azorsa |
| 2016/0152719 A1 | 6/2016 | Pardridge et al. |
| 2016/0208006 A1 | 7/2016 | Pardridge et al. |
| 2016/0251442 A1 | 9/2016 | Papadopoulos et al. |
| 2016/0319023 A1 | 11/2016 | Lundgren-Åkerlund |
| 2016/0319029 A1 | 11/2016 | Freiberg et al. |
| 2016/0324984 A1 | 11/2016 | Brinkmann et al. |
| 2016/0369297 A1 | 12/2016 | Byrne et al. |
| 2017/0007715 A1 | 1/2017 | Andreev et al. |
| 2017/0008965 A1 | 1/2017 | Ma et al. |
| 2017/0028002 A1 | 2/2017 | Byrne et al. |
| 2017/0051071 A1 | 2/2017 | Rueger et al. |
| 2017/0114152 A1 | 4/2017 | Pardridge et al. |
| 2017/0174778 A1 | 6/2017 | Shusta et al. |
| 2017/0189497 A1 | 7/2017 | Do et al. |
| 2017/0204191 A1* | 7/2017 | Bamdad .............. C12N 5/0693 |
| 2017/0260292 A1 | 9/2017 | Dennis et al. |
| 2018/0002433 A1 | 1/2018 | Zhang et al. |
| 2018/0028676 A1 | 2/2018 | Armstrong |
| 2018/0036388 A1 | 2/2018 | McIvor et al. |
| 2018/0057604 A1 | 3/2018 | Liu et al. |
| 2018/0094066 A1 | 4/2018 | Papadopoulos et al. |
| 2018/0125949 A1 | 5/2018 | LeBowitz et al. |
| 2018/0134797 A1 | 5/2018 | Zhang et al. |
| 2018/0185504 A1 | 7/2018 | Kelly et al. |
| 2018/0222992 A1 | 8/2018 | Duerr et al. |
| 2018/0222993 A1 | 8/2018 | Duerr et al. |
| 2018/0230212 A1 | 8/2018 | Hosen et al. |
| 2018/0236105 A1 | 8/2018 | Davidson et al. |
| 2018/0251571 A1 | 9/2018 | Armstrong et al. |
| 2018/0264090 A1 | 9/2018 | McIvor et al. |
| 2018/0271956 A1 | 9/2018 | McIvor et al. |
| 2018/0282408 A1 | 10/2018 | Dengl et al. |
| 2018/0344869 A1 | 12/2018 | Fischer et al. |
| 2018/0355017 A1 | 12/2018 | Baik et al. |
| 2018/0371440 A1 | 12/2018 | Koeberl et al. |
| 2019/0000984 A1 | 1/2019 | Andreev et al. |
| 2019/0030059 A1 | 1/2019 | Koeberl |
| 2019/0112588 A1 | 4/2019 | Baik et al. |
| 2019/0224246 A1 | 7/2019 | Rebar |
| 2019/0241633 A1 | 8/2019 | Fotin-Mleczek et al. |
| 2019/0269797 A1 | 9/2019 | Davidson et al. |
| 2019/0309061 A1 | 10/2019 | Papadopoulos et al. |
| 2019/0390184 A1 | 12/2019 | Mingozzi et al. |
| 2019/0390225 A1 | 12/2019 | Mingozzi et al. |
| 2020/0009267 A1 | 1/2020 | Davidson et al. |
| 2020/0095338 A1 | 3/2020 | Cygnar et al. |
| 2020/0248205 A1 | 8/2020 | Kirn et al. |
| 2020/0317798 A1 | 10/2020 | Sonoda et al. |
| 2020/0399623 A1 | 12/2020 | Baik et al. |
| 2020/0407746 A1 | 12/2020 | Vandendriessche et al. |
| 2021/0038739 A1 | 2/2021 | Takahashi et al. |
| 2021/0040464 A1 | 2/2021 | Armstrong et al. |
| 2021/0040503 A1 | 2/2021 | Mingozzi et al. |
| 2021/0079109 A1 | 3/2021 | Cygnar et al. |
| 2022/0008548 A1 | 1/2022 | Andreev et al. |
| 2022/0195011 A1 | 6/2022 | Baik et al. |
| 2022/0267477 A1 | 8/2022 | Cygnar et al. |
| 2023/0220100 A1 | 7/2023 | Cygnar et al. |

FOREIGN PATENT DOCUMENTS

| | | |
|---|---|---|
| EP | 1879624 B1 | 9/2011 |
| EP | 2420256 B1 | 2/2012 |
| EP | 1620133 B1 | 12/2015 |
| EP | 2475376 B1 | 3/2016 |
| EP | 2279210 B1 | 4/2017 |
| EP | 2861263 B1 | 12/2017 |
| EP | 3315606 A1 | 5/2018 |
| EP | 2269658 B1 | 12/2018 |
| EP | 2687597 B1 | 12/2018 |
| EP | 3075386 B1 | 10/2019 |
| EP | 3292875 B1 | 5/2020 |
| EP | 2981551 B1 | 6/2020 |
| EP | 3272773 B1 | 7/2020 |
| EP | 3461905 B1 | 8/2020 |
| KR | 10-2017-0010896 | 2/2017 |
| WO | 1997/005266 A1 | 2/1997 |
| WO | 1998/016254 A1 | 4/1998 |
| WO | 2003/057179 A2 | 7/2003 |
| WO | 2004/023973 A2 | 3/2004 |
| WO | 2005/077333 A2 | 8/2005 |
| WO | 2005/092381 A1 | 10/2005 |
| WO | 2006/108052 A2 | 10/2006 |
| WO | 2007/024323 A2 | 3/2007 |
| WO | WO 2007/075270 A1 | 7/2007 |
| WO | 2008/011710 A1 | 1/2008 |
| WO | 2008/017828 A2 | 2/2008 |
| WO | WO 2008/022295 A1 | 2/2008 |
| WO | 2009/094561 A1 | 7/2009 |
| WO | 2010/036460 A2 | 4/2010 |
| WO | 2010/119119 A1 | 10/2010 |
| WO | 2011/012316 A2 | 2/2011 |
| WO | 2011/029823 A1 | 3/2011 |
| WO | 2011/069794 A1 | 6/2011 |
| WO | 2011/069795 A1 | 6/2011 |
| WO | 2011/069796 A1 | 6/2011 |
| WO | 2011/069797 A1 | 6/2011 |
| WO | 2011/069798 A1 | 6/2011 |
| WO | 2011/069799 A1 | 6/2011 |
| WO | 2011/112566 A2 | 9/2011 |
| WO | 2012/075037 A1 | 6/2012 |
| WO | 2012/125987 A2 | 9/2012 |
| WO | 2012/136519 A1 | 10/2012 |
| WO | 2012/163932 A1 | 12/2012 |
| WO | 2013/078377 A1 | 5/2013 |
| WO | 2013/081706 A1 | 6/2013 |
| WO | 2013/138400 A1 | 9/2013 |
| WO | 2014/036076 A1 | 3/2014 |
| WO | WO 2014/085621 A1 | 6/2014 |
| WO | 2014/185908 A2 | 11/2014 |
| WO | 2014/189973 A2 | 11/2014 |
| WO | 2015/146132 A1 | 1/2015 |
| WO | 2015/026907 A1 | 2/2015 |
| WO | 2015/101588 A1 | 7/2015 |
| WO | 2015/187596 A2 | 12/2015 |
| WO | 2016/044947 A1 | 3/2016 |
| WO | 2016/065319 A1 | 4/2016 |
| WO | 2016/077840 A2 | 5/2016 |
| WO | 2016/081640 A1 | 5/2016 |
| WO | 2016/081643 A1 | 5/2016 |
| WO | 2016/094566 A2 | 6/2016 |
| WO | WO-2016085820 A1 * | 6/2016 ............. C07K 16/40 |
| WO | WO 2016/179257 A2 | 11/2016 |
| WO | 2016/207240 A1 | 12/2016 |
| WO | 2017/055540 A1 | 4/2017 |
| WO | 2017/055542 A1 | 4/2017 |
| WO | 2017/058944 A1 | 4/2017 |
| WO | 2017/100467 A2 | 6/2017 |
| WO | WO 2006/088503 A1 | 8/2017 |
| WO | WO 2017/131496 A1 | 8/2017 |
| WO | WO-2017134197 A1 * | 8/2017 ......... A61K 47/6803 |
| WO | 2017/186182 A1 | 11/2017 |
| WO | WO 2017/190079 A1 | 11/2017 |
| WO | 2017/214456 A1 | 12/2017 |
| WO | 2017/214458 A2 | 12/2017 |
| WO | 2017/214462 A2 | 12/2017 |
| WO | WO 2018/031424 A1 | 2/2018 |
| WO | 2018/102304 A1 | 6/2018 |
| WO | 2018/138322 A1 | 8/2018 |
| WO | 2018/165619 A1 | 9/2018 |
| WO | 2018/210898 A1 | 11/2018 |
| WO | 2018/213340 A1 | 11/2018 |
| WO | 2018/226861 A1 | 12/2018 |
| WO | 2019/011719 A1 | 1/2019 |
| WO | WO 2019/075417 A1 | 4/2019 |
| WO | 2019/153009 A1 | 8/2019 |
| WO | 2019/157224 A1 | 8/2019 |
| WO | 2014/143909 A1 | 9/2019 |

(56) References Cited

FOREIGN PATENT DOCUMENTS

| WO | WO 2019/197428 A1 | 10/2019 |
| WO | 2019/222411 A1 | 11/2019 |
| WO | WO 2019/222663 A1 | 11/2019 |
| WO | 2020/023390 A1 | 1/2020 |
| WO | 2020/028841 A1 | 2/2020 |
| WO | 2020/041773 A1 | 2/2020 |
| WO | 2020/102645 A1 | 5/2020 |
| WO | 2020/223362 A1 | 5/2020 |
| WO | 2020/117898 A1 | 6/2020 |
| WO | WO 2020/144233 A1 | 7/2020 |
| WO | 2020/163480 A1 | 8/2020 |
| WO | 2021/005176 A1 | 1/2021 |
| WO | WO 2017/007796 A1 | 9/2023 |

OTHER PUBLICATIONS

Pardridge WM, Boado RJ. Reengineering biopharmaceuticals for targeted delivery across the blood-brain barrier. Methods Enzymol. 2012;503:269-92. doi: 10.1016/B978-0-12-396962-0.00011-2. PMID: 22230573. (Year: 2015).*

Pardridge WM. Blood-brain barrier drug delivery of IgG fusion proteins with a transferrin receptor monoclonal antibody. Expert Opin Drug Deliv. Feb. 2015;12(2):207-22. doi: 10.1517/17425247. 2014.952627. Epub Aug. 20, 2014. PMID: 25138991. (Year: 2015).*

Spiess C, Zhai Q, Carter PJ. Alternative molecular formats and therapeutic applications for bispecific antibodies. Mol Immunol. Oct. 2015;67(2 Pt A):95-106. doi: 10.1016/j.molimm.2015.01.003. Epub Jan. 27, 2015. PMID: 25637431. (Year: 2015).*

Jäger V, Büssow K, Wagner A, Weber S, Hust M, Frenzel A, Schirrmann T. High level transient production of recombinant antibodies and antibody fusion proteins in HEK293 cells. BMC Biotechnol. Jun. 26, 2013;13:52. doi: 10.1186/1472-6750-13-52. PMID: 23802841; PMCID: PMC3699382. (Year: 2013).*

Matsui T, Sashihara S, Oh Y, Waxman SG. An orphan nuclear receptor, mROR alpha, and its spatial expression in adult mouse brain. Brain Res Mol Brain Res. Nov. 1995;33(2):217-26. doi: 10.1016/0169-328x(95)00126-d. PMID: 8750880. (Year: 1995).*

Davies AM, Sutton BJ. Human IgG4: a structural perspective. Immunol Rev. Nov. 2015;268(1):139-59. doi: 10.1111/imr.12349. PMID: 26497518; PMCID: PMC4670484. (Year: 2015).*

Salem TZ, Seaborn CP, Turney CM, Xue J, Shang H, Cheng XW. The Influence of SV40 polyA on Gene Expression of Baculovirus Expression Vector Systems. PLoS One. Dec. 14, 2015;10(12):e0145019. doi: 10.1371/journal.pone.0145019. PMID: 26659470; PMCID: PMC4686012. (Year: 2015).*

Ohashi T., Enzyme replacement therapy for lysosomal storage diseases, Pediatr Endocrinol Rev, 2012, vol. 10 Suppl. 1, pp. 26-34, see the abstract.

Ferrua F. et al., Twenty-Five Years of Gene Therapy for ADA-SCID: From Bubble Babies to an Approved Drug. Hum Gene Ther, 2017, vol. 28, N. 11, pp. 972-981, see the abstract.

Braun S.E. et al., Preclinical studies of lymphocyte gene therapy for mild Hunter syndrome (mucopolysaccharidosis type II), Hum Gene Ther, 1996, vol. 7, N. 3, pp. 283-290, see the abstract.

Rofo et al., "Enhanced neprilysin-mediated degradation of hippocampal Aβ42 with a somatostatin peptide that enters the brain," Theranostics, 11(2):789-804, (Jan. 2021).

Tanaka et al., "A novel approach to CNS dysfunction of Pompe disease with a fusion protein consisting of anti-transferrin receptor antibody and GAA enzyme," Mol. Genet. Metab., 129(2):S150-S151, (Feb. 2020).

Andrady et al., "Antibody-enzyme fusion proteins for cancer therapy," Immunotherapy,3(2):193-211, abstract only, (Feb. 2011).

Hofmeyer et al., "Protein production in Yarrowia lipolytica via fusion to the secreted lipase Lip2p," Mol. Biotechnol., 56(1):79-90, (Jul. 2013).

Jahn et al., "How to systematically evaluate immunogenicity of therapeutic proteins—regulatory considerations," N. Biotechnol., 25(5):280-286, abstract only, (Jun. 2009).

Ohashi, "Enzyme replacement therapy for lysosomal storage diseases," Pediatr. Endocrinol. Rev., 10 Suppl 1:26-34, abstract only, (Oct. 2012).

Shen et al., "Single variable domain-IgG fusion. A novel recombinant approach to Fc domain-containing bispecific antibodies," J. Biol. Chem., 281(16):10706-10714, (Apr. 2006).

Wingren et al., "Fusion of a signal sequence to the interleukin-1 beta gene directs the protein from cytoplasmic accumulation to extracellular release," Cell. Immunol., 169(2):226-237, abstract only, (May 1996).

Sun et al., "New perspectives for ERT in Pompe disease: Extending the action of the enzyme to cytosolic targets," Molecular Genetics and Metabolism, 2016, 117:S110-S111, Abstract No. 295 doi:10. 1016/j.ymgme.2015.12.453.

Statement of Relatedness under MPEP 2001.06 with Respect to U.S. Appl. No. 16/968,452, submitted Jul. 8, 2022.

Audran et al., "Internalization of human macrophage surface antigens induced by monoclonal antibodies," Journal of Immunological Methods, 1995, 188:147-154.

Azorsa, et al. "CD63/Pltgp40: A Platelet Activation Antigen Identical to the Stage-Specific Melanoma-Associated Antigen ME491," Blood, 1991, 78(2):280-284.

Barrio, et al. "Monoclonal Antibody FC-5.01, Directed Against CD63 Antigen, is Internalized into Cytoplasmic Vesicles in the IIB-BR-G Human Breast Cancer Cell Line," Hybridoma, 1998, 17(6):517-525.

Dakour, et al. "Characterization of melanosome-associated proteins by establishment of monoclonal antibodies and immunoscreening of a melanoma cDNA library through an anti-melanosome antibody," Melanoma Research, 1993, 3(5):331-336.

Demetrick, et al. "ME491 Melanoma-Associated Glycoprotein Family: Antigenic Identity of ME491, NKI/C-3, Neuroglandular Antigen (NGA), and CD63 Proteins," Journal Natl. Cancer Inst., 1992; 84(6):422-429.

Fukuda et al., "Autophagy and Mistargeting of Therapeutic Enzyme in Skeletal Muscle in Pompe Disease," Mol. Therapy, 2006, 14(6):831-839.

Fukuda et al., "Dysfunction of Endocytic and Autophagic Pathways in a Lysosomal Storage Disease," Ann Neurol, 2006, 59(4):700-708.

Hořejší and Vlček "Novel structurally distinct family of leucocyte surface glycoproteins including CD9, CD37, CD53 and CD63," FEBS, Aug. 1991, 288(1,2):1-4.

Israels and McMillan-Ward, "CD63 modulates spreading and tyrosine phosphorylation of platelets on immobilized fibrinogen," Thromb. Haemost., 2005, 93(2):311-318.

Kennel, et al., "Monoclonal Antibody to Rat CD63 Detects Different Molecular Form in Rat Tissue," Hybridoma, 1998, 17(6):509-515.

Knol, et al. "Monitoring human basophil activation via CD63 monoclonal antibody 435," J. Allergy Clin. Immunol., 1991, 88(3, Part 1):328-338.

Kraft et al., "Anti-CD63 antibodies suppress IgE-dependent allergic reactions in vitro and in vivo," JEM, 2005, 201(3):385-396.

Lee et al., "Novel strategy for a bispecific antibody: induction of dual target internalization and degradation," Oncogene, 2016, 35(34):4437-4446.

Moody et al., "Receptor Crosslinking: A General Method to Trigger Internalization and Lysosomal Targeting of Therapeutic Receptor: Ligand Complexes," Molecular Therapy, 2015, 23(12):1888-1898.

Pacak et al. "Tissue specific promoters improve specificity of AAV9 mediated transgene expression following intra-vascular gene delivery in neonatal mice," Genetic Vaccines and Therapy, 2008 6:13 (5 pages).

Valadi et al., "Exosome-mediated transfer of mRNAs and microRNAs is a novel mechanism of genetic exchange between cells," Nature Cell Biology, Jun. 2007, 9(6):654-659 and Supplementary Information (18 pages).

Verjan Garcia, et al., "SIRPa/CD172a Regulates Eosinophil Homeostasis," Journal of Immunology, 2011, 187:2268-2277.

Vischer and Wagner, "CD63 Is a Component of Weibel-Palade Bodies of Human Endothelial Cells," Blood, 1993, 82(4):1184-1191.

(56) References Cited

OTHER PUBLICATIONS

Statement of Relatedness under MPEP 2001.06 with Respect to U.S. Appl. No. 16/968,452 dated Aug. 17, 2022.
Author Unknown, The Journal of the Japanese Society of Internal Medicine, (2009) vol. 98, No. 4, p. 875-882, submitted with the English Translation of Office Action dated Mar. 24, 2022 with respect to JP 2019-567722.
Baik et al., "Engineering tissue specific delivery of enzymes for lysosomal disease treatment," Abstracts, Molecular Genetics and Metabolism, 2016, 120:S23-S24.
Ozawa, K., "Gene therapy using AAV," Virus, (2007) vol. 57, No. 1, p. 47-56 (includes English translation).
Van Der Ploeg and Reuser "Lysosomal Storage Disease 2," Lancet, 2008, 372:1342-1353.
Office Action Mar. 24, 2022 English Translation of Office Action with respect to JP 2019-567722.
Statement of Relatedness under MPEP 2001.06 with Respect to U.S. Appl. No. 16/968,452 dated Apr. 21, 2022.
Ahmad et al., "scFv Antibody: Principles and Clinical Application," Clinical and Developmental Immunology, vol. 2012, article ID 980250, 15 pages.
Andreev et al., "Bispecific Antibodies and Antibody-Drug Conjugates (ADCs) Bridging HER2 and Prolactin Receptor Improve Efficacy of HER2 ADCs," Mol. Cancer Ther., Apr. 2017, 16(4):681-693.
Anzai et al., "c-kit associated with the transmembrane 4 superfamily proteins constitutes a functionally distinct subunit in human hematopoietic progenitors," Blood, 2002, 99(12):4413-4421, doi:10.1182/blood.V99.12.4413.
Arai et al., "Design of the linkers which effectively separate domains of a bifunctional fusion protein," Protein Engineering, 2001, 14(8):529-532.
Arnold et al. "Metabolic Biotinylation Provides a Unique Platform for the Purification and Targeting of Multiple AAV Vector Serotypes," Molecular Therapy, 2006, 14(1):97-106.
Arribas and Cutler, "Weibel-Palade Body Membrane Proteins Exhibit Differential Trafficking After Exocytosis in Endothelial Cells," Traffic, 2000, 1:783-793.
Aurnhammer et al., "Universal Real-Time PCR for the Detection and Quantification of Adeno-Associated Virus Serotype 2-Derived Inverted Terminal Repeat Sequences," Hum. Gene Ther. Methods, Part B, 2012, 23:18-28.
Baik et al., "Next-generation antibody-guided enzyme replacement therapy in Pompe disease mice," Molecular Genetics and Metabolism, 2018, 123(2):S21 Abstract Only.
Baik, et al., "Targeted delivery of acid alpha-glucosidase corrects skeletal muscle phenotypes in Pompe disease mice," Biorxiv, Apr. 23, 2020; retrieved from the internet Nov. 3, 2020 https://www.biorxiv.org/content/10.1101/2020.04.22.051672v1.full.pdf.
Banerjee et al., "Targeted and armed oncolytic adenovirus via chemoselective modification," Bioorganic and Medicinal Chemistry Letters, 2011, 21(17):4985-4988.
Bareford and Swaan, "Endocytic mechanisms for targeted drug delivery," Advanced Drug Delivery Reviews, Elsevier, Amsterdam, NL, 2007, 59(8):748-758.
Bartlett et al., "Infectious Entry Pathway of Adeno-Associated Virus and Adeno-Associated Virus Vectors," Journal of Virology, 2000, 74(6):2777-2785.
Barzel et al., "Promoterless gene targeting without nucleases ameliorates hemophilia B in mice," Nature, 2015, 517(7534):360-364.
Battig et al., "Programmable Release of Multiple Protein Drugs from Aptamer-Functionalized Hydrogels via Nucleic Acid Hybridization," J. Am. Chem. Society., 2012, 134:12410-12413.
Beatty, "Trafficking from CD63-positive late endocytic multivesicular bodies is essential for intracellular development of *Chlamydia trachomatis*," Journal of Cell Science, 2006, 119(2):350-359.
Bedinger et al., "Differential Pathway Coupling of the Activated Insulin Receptor Drives Signaling Selectivity by XMetA, an Allosteric Partial Agonist Antibody," Journal of Pharmacology and Experimental Therapeutics, 2015, 353(1):35-43.

Berditchevski et al., "Specific Association of CD63 with the VLA-3 and VLA-6 Integrins," Journal of Biological Chemistry, 1995, 270(30):17784-17790.
Berditchevski et al., "Characterization of Novel Complexes on the Cell Surface between Integrins and Proteins with 4 Transmembrane Domains (TM4 proteins)," Molecular Biology of the Cell, 1996, 7:193-207.
Berditchevski et al., "A Novel Link between Integrins, Transmembrane-4 Superfamily Proteins (CD63 and CD81), and Phosphatidylinositol 4-Kinase*," Journal of Biological Chemistry, Jan. 1997, 272(5):2595-2598.
Berditchevski et al., "Generation of Monoclonal Antibodies to Integrin-associated Proteins," Journal of Biological Chemistry, Nov. 1997, 272(46):29174-29180.
Berditchevski et al., "Expression of the Palmitoylation-deficient CD151 Weakens the Association of $\alpha 3\beta 1$ Integrin with the Tetraspanin-enriched Microdomains and Affects Integrin-dependent Signaling*," Journal of Biological Chemistry, 2002, 277(40):36991-37000.
Berger et al., "Fusion protein technologies for biopharmaceuticals: Applications and challenges," mAbs, 2015, 7(3):456-460.
Bezwada et al., "A Novel Allosteric Insulin Receptor-Activating Antibody Reduces Hyperglycemia without Hypoglycemia in Diabetic Cynomolgus Monkeys," Journal of Pharmacology and Experimental Therapeutics, 2016, 356(2):466-473.
Bian et al., "Selective gene transfer in vitro to tumor cells via recombinant Newcastle disease virus," Cancer Gene Ther., 2005, 12:295-303.
Bian et al., "In vivo efficacy of systemic tumor targeting of a viral RNA vector with oncolytic properties using a bispecific adapter protein," Int. J. Oncol., 2006, 29:1359-1369.
Bixby et al. "A Phase I Study of IGN523, a Novel Anti-CD98 Monoclonal Antibody in Patients with Relapsed or Refractory Acute Myeloid Leukemia (AML)," Blood, 2015, 126(23):3809.
Blechacz and Russell, "Measles Virus as an Oncolytic Vector Platform," Current Gene Therapy, 2008, 8:162-175.
Boado et al., "Genetic Engineering of a Lysosomal Enzyme Fusion Protein for Targeted Delivery Across the Human Blood-Brain Barrier," Biotechnology and Bioengineering, Feb. 1, 2008, 99(2):475-484.
Boado et al., "IgG-Enzyme Fusion Protein: Pharmacokinetics and Anti-Drug Antibody Response in Rhesus Monkeys," Bioconjugate Chemistry, 2013, 24(1):97-104.
Boado et al, "Insulin Receptor Antibody-Sulfamidase Fusion Protein Penetrates the Primate Blood-Brain Barrier and Reduces Glycosoaminoglycans in Sanfilippo Type A Cells," Mol Pharm. 11(8):2928-2934 (Aug. 4, 2014).
Boado et al., "Very High Plasma Concentrations of a Monoclonal Antibody against the Human Insulin Receptor Are Produced by Subcutaneous Injection in the Rhesus Monkey," Mol. Pharmaceutics, 2016, 13(9):3241-3246.
Boado et al., "Reduction in Brain Heparan Sulfate with Systemic Administration of an IgG Trojan Horse-Sulfamidase Fusion Protein in the Mucopolysaccharidosis Type IIIA Mouse," Molecular Pharmaceutics, 2018, 15:602-608.
Bode et al., "Antibody-Directed Fibrinolysis: An Antibody Specific for Both Fibrin and Tissue Plasminogen Activator," Journal of Biological Chemistry, Jan. 1989, 264(2):944-948.
Bonardi et al., "Delivery of Saporin to Human B-Cell Lymphoma Using Bispecific Antibody: Targeting via CD22 but not CD19, CD37, or Immunoglobulin Results in Efficient Killing," Cancer Research, Jul. 1993, 53(13):3015-3021.
Boustany, "Lysosomal storage diseases—the horizon expands," Nat. Rev. Neurol., Oct. 2013, 9(10):583-598.
Cabezon et al., "Trafficing of Gold Nanoparticles Coated with the 8D3 Anti-Transferrin Receptor Antibody at the Mouse Blood-Brain Barrier," Molecular Pharmaceutics, 2015, 12(11),4137-4145 DOI: 10.1021/acs.molpharmaceut.5b00597.
Campadelli-Fiume et al., "Rethinking herpes simplex virus: the way to oncolytic agents," Reviews in Medical Virology, 2011, 21:213-226.

(56) References Cited

OTHER PUBLICATIONS

Catelas et al., "Controlled Release of Bioactive Transforming Growth Factor Beta-1 from Fibrin Gels In Vitro," Tissue Engineering: Part C, 2008, 14(2):119-128.
Chadwick et al., "Modification of Retroviral Tropism by Display of IGF-I," Journal of Molecular Biology, 1999, 285:485-494.
Chen et al., "Fusion Protein Linkers: Property, Design and Functionality," Adv Drug Deliv Rev., 2013, 65(10):1357-1369.
Chiba, "Molecular Mechanism in α-Glucosidase and Glucoamylase," Biosci. Biotechnol. Biochem., 1997, 61(8):1233-1239.
Chuah et al., "Liver-Specific Transcriptional Modules Identified by Genome-Wide In Silico Analysis Enable Efficient Gene Therapy in Mice and Non-Human Primates," Mol. Ther., 2014, 22(9):1605-1613.
Cieniewicz et al., "Novel Monoclonal Antibody Is an Allosteric Insulin Receptor Antagonist That Induces Insulin Resistance," Diabetes, 2017, 66(1):206-217.
Clevenger and Kline, "Prolactin receptor signal transduction," 10(10) Lupus, (2001) 10:706-718.
Corti et al., "Safety of Intradiaphragmatic Delivery of Adeno-Associated Virus-Mediated Alpha-Glucosidase (rAAV1-CMV-hGAA) Gene Therapy in Children Affected by Pompe Disease," Human Gene Therapy Clinical Development, 2017, 28(4):208-218.
Couch et al. "Addressing Safety Liabilities of TfR Bispecific Antibodies That Cross the Blood-Brain Barrier," Science Translational Medicine, 2013, vol. 5, Issue 183, pp. 183ra57 DOI: 10.1126/scitranslmed.3005338.
Dalba et al., "Beyond Oncolytic Virotherapy: Replication-Competent Retrovirus Vectors for Selective and Stable Transduction of Tumors," Current Gene Therapy, 2005, 5:655-667.
Darvish-Damavandi et al., "Towards the development of an enzyme replacement therapy for the metabolic disorder propionic acidemia," Molecular Genetics and Metabolism Reports, 2016, 8(1):51-60.
De Goeij et al., "Efficient Payload Delivery by a Bispecific Antibody-Drug Conjugate Targeting HER2 and CD63," Mol. Cancer Ther., 2016, 15(11):2688-2697.
Derosa et al., "Therapeutic efficacy in a hemophilia B model using a biosynthetic mRNA liver depot system," Gene Therapy, 2016, 23:699-707.
Desnick and Schuchman, "Enzyme replacement therapy for lysosomal diseases: lessons from 20 years of experience and remaining challenges," 13 Annu. Rev. Genomics Hum. Genet., 2012, 13:307-335.
Dhital et al., "Mammalian Mucosal α-Glucosidases Coordinate with α-Amylase in the Initial Starch Hydrolysis Stage to Have a Role in Starch Digestion Beyond Glucogenesis," PLoS One, 2013, 8(4):e62546, 13 pages.
Dimauro and Spiegel, "Progress and problems in muscle glycogenosis," Acta Myologica, Oct. 2011, 30(2):96-102.
Doyle et al., "CD63 is an essential cofactor to leukocyte recruitment by endothelial P-selectin," Blood, 2011, 118(15):4265-427.
Duffield et al., "The tetraspanin CD63 enhances the internalization of the H,K-ATPase β-subunit," Proc. Nail. Acad. Sci. USA, Dec. 2003, 100(26):15560-15565.
Egea et al., "Tissue inhibitor of metalloproteinase-1 (TIMP-1) regulates mesenchymal stem cells through let-7f microRNA and Wnt/β-catenin signaling," PNAS, 2012, 109(6):E309-E316.
Einfeld, et al., "Reducing the Native Tropism of Adenovirus Vectors Requires Removal of both CAR and Integrin Interactions," J. Virol., 2001, 75(23):11284-11291.
Elmallah et al., "Sustained Correction of Motoneuron Histopathology Following Intramuscular Delivery of AAV in Pompe Mice," The American Society of Gene & Cell Therapy, Apr. 2014, 22(4):702-712.
Engering and Pieters, "Association of distinct tetraspanins with MHC class II molecules at different subcellular locations in human immature dendritic cells," International Immunology, 2001, 13(2):127-134.
Erlwein et al., "Chimeric Ecotropic MLV Envelope Proteins that Carry EGF Receptor-Specific Ligands and the Pseudomonas Exotoxin A Translocation Domain to Target Gene Transfer to Human Cancer Cells," Virology, 2002, 302:333-341.
Falk et al., "Peripheral nerve and neuromuscular junction pathology in Pompe disease," Human Molecular Genetics, 2015, 24(3):625-636.
Ferland et al., "The effect of chloroquine on lysosomal prolactin receptors in rat liver," Endocrinology, 1984, 115(5):1842-1849.
Flannery et al., "Palmitoylation-dependent association with CD63 targets the CA2+ sensor synaptotagmin VII to lysosomes," J. Cell Biol., Nov. 2010, 191(3):599-613.
Fuentealba et al., "Low-Density Lipoprotein Receptor-Related Protein 1 (LRP1) Mediates Neuronal Aβ42 Uptake and Lysomal Trafficking," PLoS One 5(7):e11884, pp. 1-10, Jul. 2010.
Fuller et al., "Isolation and characterisation of a recombinant, precursor form of lysosomal acid alpha-glucosidase," European Journal of Biochemistry, 1995, 234(3):903-909.
Galanis, "Therapeutic Potential of Oncolytic Measles Virus: Promises and Challenges," Clinical Pharmacology and Therapeutics, 2010, 88(5):620-625.
Galmiche et al., "Expression of a functional single chain antibody on the surface of extracellular enveloped vaccinia virus as a step towards selective tumour cell targeting," Journal of General Virology, 1997, 78:3019-3027.
Gao et al., "Novel adeno-associated viruses from rhesus monkeys as vectors for human gene therapy," PNAS, 2002, 99(18):11854-11859.
Geel et al., "Pompe disease: Current state of treatment modalities and animal models," Molecular Genetics and Metabolism, 2007, 92:299-307.
Gelperina et al., "The Potential Advantages of Nanoparticle Drug Delivery Systems in Chemotherapy of Tuberculosis," Am J Respir Crit Care Med., 172(12):1487-1490 (2005).
Genty et al., "Endocytosis and degradation of prolactin and its receptor in Chinese hamster ovary cells stably transfected with prolactin receptor cDNA," Mol. Cell Endocrinol., 1994, 99(2):221-228.
Ghaderi et al., "Production platforms for biotherapeutic glycoproteins. Occurrence, impact, and challenges of non-human sialylation," Biotechnol. Genet. Eng. Rev., 2012, 28:147-175.
Ghosh et al., "An Endocytosed TGN38 Chimeric Protein is Delivered to the TGN after Trafficking Through the Endocytic Recycling Compartment in CHO Cells," J. Cell Bioi., Aug. 1998, 142(4):923-936.
Gigout et al., "Altering AAV Tropism with Mosaic Viral Capsids," Molecular Therapy, 2005, 11(6):856-865.
Girod et al., "Genetic capsid modifications allow efficient re-targeting of adeno-associated virus type 2," Nature Medicine, 1999, 5(9):1052-1056.
Glasgow et al., "A Strategy for Adenovirus Vector Targeting with a Secreted Single Chain Antibody," PLOS One, 2009, 4(12):e8355, 12 pages.
Grabow and Jaeger, "Loaded-up microsponges," Nature Materials, 2012, 11:268-269.
Gray et al., "Production of recombinant adeno-associated viral vectors and use in vitro and in vivo administration", Current Protocols in Neuroscience, 2011, Chapter: Unit 4.17, 36 pages, doi:10.1002/0471142301.ns0417s57.
Grifman et al., "Incorporation of Tumor-Targeting Peptides into Recombinant Adeno-associated Virus Capsids," Molecular Therapy, 2001, 3(6):964-975.
Guse et al., "Oncolytic vaccinia virus for the treatment of cancer," Expert Opinion on Biological Therapy, 2011, 11(5):595-608.
Haijema et al., "Switching Species Tropism: an Effective Way to Manipulate the Feline Coronavirus Genome," J. Virol., 2003, 77(8):4528-4538.
Haijema et al., "Live, Attenuated Coronavirus Vaccines through the Directed Deletion of Group-Specific Genes Provide Protection against Feline Infectious Peritonitis," J. Virology, 2004, 78(8):3863-3871.
Hakomori, "Glycosphingolipids in Cellular Interaction, Differentiation, and Oncogenesis," Annual Review of Biochemistry, Jul. 1981, 50:733-764.

(56) References Cited

OTHER PUBLICATIONS

Hammond et al., "Single-Chain Antibody Displayed on a Recombinant Measles Virus Confers Entry through the Tumor-Associated Carcinoembryonic Antigen," Journal of Virology, 2001, 75(5):2087-2096.
Hayashi et al., "Apolipoprotein E-Containing Lipoproteins Protect Neurons from Apoptosis via Signaling Pathway Involving Low-Density Lipoprotein Receptor-Related Protein-1," Journal of Neuroscience, 27(8):1933-1941, Feb. 21, 2007.
Hayes et al., "Antitumor activity of an anti-CD98 antibody," International Journal of Cancer, 2015, 137:710-720.
Hemler, (2008) "Targeting of tetraspanin proteins—potential benefits and strategies," Nat. Rev. Drug. Discov. 7(9):747-758, doi:10.1038/nrd2659.
Hemminki et al., "Targeting Oncolytic Adenoviral Agents to the Epidermal Growth Factor Pathway with a Secretory Fusion Molecule," Cancer Res., 2001, 61: 6377-6381.
Henning et al., "Genetic Modification of Adenovirus 5 Tropism by a Novel Class of Ligands Based on a Three-Helix Bundle Scaffold Derived from Staphylococcal Protein A," Human Gene Therapy, 2002, 13:1427-1439.
Hesselink et al., "Lysosomal dysfunction in muscle with special reference to glycogen storage disease type II," Biochim. Biophys. Acta., 2003, 1637(2):164-170.
Hirst et al., "Characterization of a Fourth Adaptor-related Protein Complex," Molecular Biology of the Cell, 1999, 10:2787-2802.
Holliger et al., ""Diabodies": Small bivalent and bispecific antibody fragments," PNAS USA, 1993, 90:6444-6448.
Hordeaux et al., "Long-term neurologic and cardiac correction by intrathecal gene therapy in Pompe disease," Acta Neuropathologica Communications, 2017, 5:66 (19 pages).
Huie et al., "Increased Occurrence of Cleft Lip in Glycogen Storage Disease Type II (GSDII): Exclusion of a Contiguous Gene Syndrome in Two Patients by Presence of Intragenic Mutations Including a Novel Nonsense Mutation Gln58Stop," Am. J. Med. Genet., 1999, 85(1):5-8.
Huie et al., "Glycogen Storage Disease Type II: Identification of Four Novel Missense Mutations (D645N, G648S, R672W, R672Q) and Two Insertions/Deletions in the Acid α-Glucosidase Locus of Patients of Differing Phenotype," Biochem. Biophys. Res. Commun., 1998, 244(3):921-927.
Huston et al, "Protein engineering of antibody binding sites: Recovery of specific activity in an anti-digoxin single-chain Fv analogue produced in *Escherichia coli*," PNAS, 1988, 85:16:5879-5883.
Kelly et al., "Preclinical Activity of the Novel Anti-Prolactin Receptor (PRLR) Antibody-Drug Conjugate REGN2878-DM1 in PRLR-Positive Breast Cancers," Mol. Cancer Ther., 2017, 16(7):1299-1311 doi:10.1158/1535-7163.MCT-16-0839.Epub2017Apr4.
Kidd et al., "Fibrin hydrogels for lentiviral gene delivery in vitro and in vivo," Journal of Controlled Release, 2012, 157(1):80-85.
Kitani et al., "A Cell Surface Glycoprotein of Rat Basophilic Leukemia Cells Close to the High Affinity IgE Receptor (FcεRI)," Journal of Biological Chemistry, 1991, 266(3):1903-1909.
Klimstra et al., "Targeting Sindbis virus-based vectors to Fc receptor-positive cell types," Virology, 2005, 338:9-21.
Kobayashi et al., "The Tetraspanin CD63/lamp3 Cycles between Endocytic and Secretory Compartments in Human Endothelial Cells," Molecular Biology, May 2000, 11:1829-1843.
Koeberl et al., "Enhanced efficacy of enzyme replacement therapy in Pompe disease through mannose-6-phosphate receptor expression in skeletal muscle," Mol. Genet. Metab., 2011, 103(2):107-112.
Kraft et al., "The tetraspanin CD63 is required for efficient IgE-mediated mast cell degranulation and anaphylaxis," J. Immunol, 2013, 191(6):2871-2878.
Latysheva et al., "Syntenin-1 Is a New Component of Tetraspanin-Enriched Microdomains: Mechanisms and Consequences of the Interaction of Syntenin-1 with CD63," Molecular and Cellular Biology, Oct. 2006, 26(20):7707-7718.

Lee et al., "Impaired Retrograde Membrane Traffic Through Endosomes in a Mutant CHO Cell Defective in Phosphalidyl Serine Synthesis," Genes to Cells, 2012, 17:728-736.
Lekishvili et al., "The tumour-associated antigen L6 (L6-Ag) is recruited to the tetraspanin-enriched microdomains: implication for tumour cell motility," Journal of Cell Science, 2008, 121(5):685-694, doi:10.1242/jcs.020347.
Lieu et al., "The Golgin GCC88 Is Required for Efficient Retrograde Transport of Cargo from the Early Endosomes to the Trans-Golgi Network," Mol. Bioi. Cell, Dec. 2007, 18:4979-4991.
Maecker et al., "The tetraspanin superfamily: molecular facilitators," FASEB J., May 1997, 11(6)428-442.
Maga et al., "Glycosylation-independent Lysosomal Targeting of Acid α-Glucosidase Enhances Muscle Glycogen Clearance in Pompe Mice," J. Biol. Chem., 2013, 288(3):1428-1438.
Mantegazza et al., "CD63 Tetraspanin Slows Down Cell Migration and Translocates to the Endosomal-Lysosomal-MIICs Route after Extracellular Stimuli in Human Immature Dendritic Cells," Blood, Aug. 2004, 104(4):1183-1190.
Martin et al., "Tetraspanins in Viral Infections: a Fundamental Role in Viral Biology?," Journal of Virology, 2005, 79(17):10839-10851.
Metzelaar et al., "CD63 antigen. A novel lysosomal membrane glycoprotein, cloned by a screening procedure for intracellular antigens in eukaryotic cells," J. Biol. Chem., 1991, 266(5):3239-3245.
Muenzer, "Early initiation of enzyme replacement therapy for the mucopolysaccharidoses," Mol. Genet. Metab., Feb. 2014, 111(2):63-72.
Nakamura and Russell "Oncolytic measles viruses for cancer therapy," Expert Opinion on Biological Therapy, 2004, 4(10):1685-1692.
Nakano et al., "Herpes Simplex Virus Targeting to the EGF Receptor by a gD-Specific Soluble Bridging Molecule," Mol. Ther., Apr. 2005, 11(4):617-624.
Nicklin and Baker, "Tropism-Modified Adenoviral and Adeno-Associated Viral Vectors for Gene Therapy," Curr. Gene Ther., 2002, 2:273-293.
Nishibori et al., "The Protein CD63 Is in Platelet Dense Granules, Is Deficient in a Patient with Hermansky-Pudlak Syndrome, and Appears Identical to Granulophysin," J. Clin. Invest., 1993, 91(4):1775-1782.
Nishijima et al., "Human Scavenger Receptor A1-Mediated Inflammatory Response to Silica Particle Exposure Is Size Specific," Frontiers in Immunology, 2017, 8(0):379, 12 pages.
Nishiyama et al., "Akt inactivation induces endoplasmic reticulum stress-independent autophagy in fibroblasts from patients with Pompe disease," Molecular Genetics and Metabolism, 2012, 107:490-495.
Ohno et al., "Cell-specific targeting of Sindbis virus vectors displaying IgG-binding domains of protein A," Nature Biotechnology, 1997, 15:763-767.
Oka and Bulleid, "Forming disulfides in the endoplasmic reticulum," Biochim Biophys Acta, 2013, 1833(11):2425-2429.
Otto, et al., "A Neutralizing Prolactin Receptor Antibody Whose In Vivo Application Mimics the Phenotype of Female Prolactin Receptor-Deficient Mice," Endocrinology, 2015, 156: 4365-4373.
Papapetrou and Schambach, "Gene Insertion Into Genomic Safe Harbors for Human Gene Therapy," J. Molecular Therapy, Apr. 2016, 24(4):678-684.
Pardridge "Blood-brain barrier drug delivery of IgG fusion proteins with a transferrin receptor monoclonal antibody," Expert Opinion, Drug Delivery, 2015, 12(2):207-222.
Pardridge "Blood-brain barrier endogenous transporters as therapeutic targets: a new model for small molecule CNS drug discovery," Expert Opinion on Therapeutic Targets, 2015, 19(8):1059-1072.
Pardridge "Re-engineering therapeutic antibodies for Alzheimer's disease as blood-brain barrier penetrating bi-specific antibodies," Expert Opinion on Biological Therapy, 2016, 16(12):1455-1468.
Pardridge "CSF, blood-brain barrier, and brain drug delivery," Expert Opinion on Drug Delivery, 2016, 13(7):963-975.
Pardridge et al., "Plasma Pharmacokinetics of Valanafusp Alpha, a Human Insulin Receptor Antibody-Iduronidase Fusion Protein, in Patients with Mucopolysaccharidosis Type I," BioDrugs, 2018, 32(2):169-176.

(56) References Cited

OTHER PUBLICATIONS

Parenti et al., "Lysomal Storage Diseases: From Pathophysiology to Therapy," Ann. Rev. Med., 66:471-486, Jan. 2015.
Park et al., "Cancer gene therapy using adeno-associated virus vectors," Frontiers in Bioscience, Jan. 2008, 13:2653-2659.
Park et al., "Epidermal growth factor (EGF) receptor targeted delivery of PEGylated adenovirus," Biochemical and Biophysical Research Communications, 2008, 366:769-774.
Paul et al., "Specific Tumor Cell Targeting by a Recombinant MVA Expressing a Functional Single Chain Antibody on the Surface of Intracellular Mature Virus (IMV) Particles," Viral Immunology, 2007, 20(4):664-671.
Pereboeva et al., "Targeting EGFR with metabolically biotinylated fiber-mosaic adenovirus," Gene Therapy, 2007, 14(8):627-637.
Pizzato et al., "Evidence for nonspecific adsorption of targeted retrovirus vector particles to cells," Gene Therapy, 2001, 8:1088-1096.
Poljak et al., "Production and structure of diabodies," Structure, 1994, 2:1121-1123.
Pols and Klumperman, "Trafficking and Function of the Tetraspanin CD63," Exp. Cell Res., Oct. 2009, 315:1584-1592.
Ponnazhagan et al., "Conjugate-Based Targeting of Recombinant Adeno-Associated Virus Type 2 Vectors by Using Avidin-Linked Ligands," J. Virol., 2002, 76(24):12900-12907.
Prabakaran et al., "Mannose 6-Phosphate Receptor and Sortilin Mediated Endocytosis of α-Galactosidase A in Kidney Endothelial Cells," PLoS One, 2012, 7(6):e39975, 9 pages.
Puzzo et al., "Rescue of Pompe disease in mice by AAV-mediated liver delivery of secretable acid α-glucosidase," Science Translational Medicine, Nov. 29, 2017, 9(418):eaam6375 (12 pages).
Quetglas et al., "Alphavirus vectors for cancer therapy," Virus Research, 2010, 153:179-196.
Quezada-Calvillo et al., "Luminal Starch Substrate "Brake" on Maltase-Glucoamylase Activity is Located within the Glucoamylase Subunit," Journal of Nutrition, 2008, 138(4):685-692.
Raben et al., "Enzyme replacement therapy in the mouse model of Pompe disease," Molecular Genetics and Metabolism, 2003, 80:159-169.
Robinson e al., "Optimizing the stability of single-chain proteins by linker length and composition mutagenesis," PNAS, 1998, 95(11):5929-5934.
Rous et al., "Role of Adaptor Complex AP-3 in Targeting Wild-Type and Mutated CD63 to Lysosomes," Molecular Biology of the Cell, Mar. 2002, 13:1071-1082.
Rubinstein et al., "CD9, CD63, CD81, and CD82 are components of a surface tetraspan network connected to HLA-DR and VLA integrins," Eur. J. Immunol., 1996, 26:2657-2665.
Russell and Cosset, "Modifying the Host Range Properties of Retroviral Vectors," Journal of Gene Medicine, 1999, 1:300-311.
Russell and Peng, "Measles virus for cancer therapy," Current Topics in Microbiology and Immunology, 2009, 330:213-241.
Sasisekharan et al., "Glycomics Approach to Structure-Function Relationships of Glycosaminoglycans," Ann. Rev. Biomed. Eng., Dec. 2014, 8(1):181-231.
Schänzer et al., "Quantification of muscle pathology in infantile Pompe disease," Neuromuscular Disorders, 2017, 27:141-152.
Schröder et al., "Deficiency of the Tetraspanin CD63 Associated with Kidney Pathology but Normal Lysosomal Function," Mol. Cell. Biol., 2009, 29(4):1083-1094.
Shah and Breakefield, "Hsv Amplicon Vectors for Cancer Therapy," Current Gene Therapy, 2006, 6:361-370.
Shen et al., "A map of the cis-regulatory sequences in the mouse genome," Nature, 2012, 488(7409):116-120, doi:10.1038/nature11243.
Shi et al., "Insertional Mutagenesis of the Adeno-Associated Virus Type 2 (AAV2) Capsid Gene and Generation of AAV2 Vectors Targeted to Alternative Cell-Surface Receptors," Human Gene Therapy, 2001, 12:1697-1711.

Shi and Bartlett, "RGD Inclusion in VP3 Provides Adeno-Associated Virus Type 2 (AAV2)-Based Vectors with a Heparan Sulfate-Independent Cell Entry Mechanism," Molecular Therapy, Apr. 2003, 7(4):515-525.
Shimamoto et al., "Peptibodies: A flexible alternative format to antibodies," Mabs, 2012, 4(5):586-591.
Sidman et al., "Temporal Neuropathological and Behavioral Phenotype of $6^{Neo}/6^{Neo}$ Pompe Disease Mice," Author Manuscript, J. Neuropathol. Exp. Neurol., Aug. 2008, 67(8):803-818.
Sim et al., "Human Intestinal Maltase-Glucoamylase: Crystal Structure of the N-Terminal Catalytic Subunit and Basis of Inhibition and Substrate Specificity," J. Mol. Biol., 2008, 375:782-792.
Skubitz et al., "CD63 associates with tyrosine kinase activity and CD11/CD18, and transmits an activation signal in neutrophils," Journal of Immunology, 1996, 157:3617-3626.
Spicer and Mikos, "Fibrin Glue as a Drug Delivery System," Journal of Controlled Release, 2010, 148(1):49-55.
Stachler and Bartlett, "Mosaic vectors comprised of modified AAV1 capsid proteins for efficient vector purification and targeting to vascular endothelial cells," Gene Ther., 2006, 13:926-931.
Stachler et al., "Site-specific Modification of AAV Vector Particles With Biophysical Probes and Targeting Ligands Using Biotin Ligase," Molecular Therapy, 2008, 16(8):1467-1473.
Tai and Kasahara, "Replication-competent retrovirus vectors for cancer gene therapy," Frontiers in Bioscience, 2008., 13:3083 3095.
Tajima et al., "Use of a Modified α-N-Acetylgalactosaminidase in the Development of Enzyme Replacement Therapy for Fabry Disease," Am. J. Hum. Genet., 2009, 85(5):569-580.
Takino et al., "Tetraspanin CD63 promotes targeting and lysosomal proteolysis of membrane-type 1 matrix metalloproteinase," Biochem. Biophys. Res. Commun., 2003, 304:160-166.
Tuli et al., "Mechanism for amyloid precursor-like protein 2 enhancement of major histocompatibility complex class I molecule degradation," J Biol Chem. 2009, 284(49):34296-34307, doi: 10.1074/jbc.M109.039727. Epub Oct. 6, 2009.
Tuma and Hubbard, "Transcytosis: Crossing Cellular Barriers," Physiological Reviews, Jul. 1, 2003, 83(3):871-935.
Umapathysivam et al., "Correlation of acid alpha-glucosidase and glycogen content in skin fibroblasts with age of onset in Pompe disease," Clin. Chim. Acta., 2005, 361:191-198.
Van Beusechem et al., "Conditionally replicative adenovirus expressing a targeting adapter molecule exhibits enhanced oncolytic potency on CAR-deficient tumors," Gene Therapy, 2003, 10:1982-1991.
Verheije and Rottier, (2012) "Retargeting of Viruses to Generate Oncolytic Agents," Advances in Virology, 2012, 2012:1-15.
Vincent and Zurini, "Current strategies in antibody engineering: Fc engineering and pH-dependent antigen binding, bispecific antibodies and antibody drug conjugates," Biotechnol. J., 2012, 7:1444-1450.
Ward et al., "Binding activities of a repertoire of single immunoglobulin variable domains secreted from *Escherichia coli*," Nature, 1989, 341:544-546.
White et al., "Targeted Gene Delivery to Vascular Tissue In Vivo by Tropism-Modified Adeno-Associated Virus Vectors," Circulation, 2004, 109:513-519.
Wurdinger et al., "Targeting non-human coronaviruses to human cancer cells using a bispecific single-chain antibody," Gene Therapy, 2005, 12:1394-1404.
Xiao and Gan "Receptor-Mediated Endocytosis and Brain Delivery of Therapeutic Biologics," International Journal of Cell Biology, vol. 2013, Article ID 703545, 14 pages.
Yauch and Hemler, "Specific interactions among transmembrane 4 superfamily (TM4SF) proteins and phosphoinositide 4-kinase," Biochem. J., 2000, 351:629-637.
Yi et al., "Antibody-mediated enzyme replacement therapy targeting both lysosomal and cytoplasmic glycogen in Pompe disease," J. Mol. Med., 2017, 95(5):513-521.
Yoshida et al., "A CD63 Mutant Inhibits T-cell Tropic Human Immunodeficiency Virus Type 1 Entry by Disrupting CXCR4 Trafficking to the Plasma Membrane," Traffic, Feb. 2008, 9:540-558.
Yu et al. "Pattern Recognition Scavenger Receptor CD204 Attenuates Toll-like Receptor 4-induced NF-κB Activation by Directly

(56) References Cited

OTHER PUBLICATIONS

Inhibiting Ubiquitination of Tumor Necrosis Factor (TNF) Receptor-associated Factor 6*," Journal of Biological Chemistry, 2011, 286(21):18795-18806.

Yu et al., "Boosting Brain Uptake of a Therapeutic Antibody by Reducing Its Affinity for a Transcytosis Target," Science Translational Medicine, 2011, vol. 3, Issue 84, pp. 84ra44.

Yu et al., "Therapeutic bispecific antibodies cross the blood-brain barrier in nonhuman primates," Science Translational Medicine, Nov. 5, 2014, 6(261)261ra154 DOI: 10.1126/scitranslmed.3009835.

Zhu et al., "Conjugation of Mannose-6-Phosphate-containing Oligosaccharides to Acid α-Glucosidase Improves the Clearance of Glycogen in Pompe Mice," J. Biol. Chem., 2004, 279(48):50336-50341.

Zolotukhin et al., "Recombinant adeno-associated virus purification using novel methods improves infectious titer and yield," Gene Ther., 1999, 6:973-985.

Zuchero et al., "Discovery of Novel Blood-Brain Barrier Targets to Enhance Brain Uptake of Therapeutic Antibodies," Neuron, 89(1):70-82 (Jan. 6, 2016).

R & D Systems "Integrin alpha 7: Products" for exemplary non-limiting anti-IGTA7 antibodies https://www.rndsystems.com/target/integrin-alpha-7?category=Primary%20Antibodies&utm_source=genecards&utm_medium=referral&utm_campaign=product&utm_term=primaryantibodies.

Origene Antibodies for ASGR2 https://www.origene.com/category/antibodies?q=ASGR2&sub_category=Primary+Antibodies&reactivities=Human.

R&D Systems product sheet for MAB27081, Human SR-AI/MSR1 Antibody (R&D Systems #MAB27081) https://www.rndsystems.com/products/human-sr-ai-msr1-antibody-351620_mab27081.

R&D Systems product sheet for AF2708, Human SR-AI/MSR1 Antibody (R&D Systems # AF2708) https://www.rndsystems.com/products/human-sr-ai-msr-antibody_af2708.

Anti-Macrophage Scavenger Receptor I antibody [EPR7536] (Abcam #ab151707) (Rabbit) https://www.abcam.com/cd204-antibody-epr7536_ab151707.html.

International Search Report and Written Opinion Received for PCT Application No. PCT/US2019/017116, mailed May 15, 2019.

Statement of Relatedness under MPEP 2001.06 with Respect to U.S. Appl. No. 16/968,452 dated Jul. 15, 2021.

Almagro et al., "Progress and Challenges in the Design and Clinical Development of Antibodies for Cancer Therapy," Front. Immunol., 8:1751, (Jan. 2018).

Brown et al., :"Tolerance of single, but not multiple, amino acid replacements in antibody VH CDR 2: a means of minimizing B cell wastage from somatic hypermutation?," J. Immunol., 156(9): 3285-3291, (1996).

Chiu et al., "Antibody Structure and Function: The Basis for Engineering Therapeutics," Antibodies (Basel), 8(4):55, (2019).

Devay et al., "Improved Lysosomal Trafficking Can Modulate the Potency of Antibody Drug Conjugates," Bioconjug. Chem., 28(4):1102-1114, (Feb. 2017).

Hsu et al., "Enhanced delivery of α-glucosidase for Pompe disease by ICAM-1-targeted nanocarriers: comparative performance of a strategy for three distinct lysosomal storage disorders," Nanomedicine, 8(5):731-739, (2012).

Mazor et al.. "Enhanced tumor-targeting selectivity by modulating bispecific antibody binding affinity and format valence," Sci. Rep., 7:40098, (Jan. 2017).

Pardridge, "Blood-brain barrier drug delivery of IgG fusion proteins with a transferrin receptor monoclonal antibody," Expert Opin. Drug Deliv., 12(2):207-22, (Aug. 20, 2014).

Paterson et al., "Exploiting transferrin receptor for delivering drugs across the blood-brain barrier," Drug Discov. Today Technol., 20:49-52, (Oct. 27, 2016).

Rudikoff et al., "Single amino acid substitution altering antigen-binding specificity," Proc. Natl. Acad. Sci. U.S.A., 79(6):1979-1983, (Mar. 1982).

Saftig et al., "Lysosome biogenesis and lysosomal membrane proteins: trafficking meets function," Nature Reviews, Molecular Cell Biology, vol. 10, 623-635, (Sep. 2009).

Zhou et al., "Antibody-Mediated Enzyme Therapeutics and Applications in Glycogen Storage Diseases," Trends Mol. Med., 25(12):1094-1109, (2019).

* cited by examiner

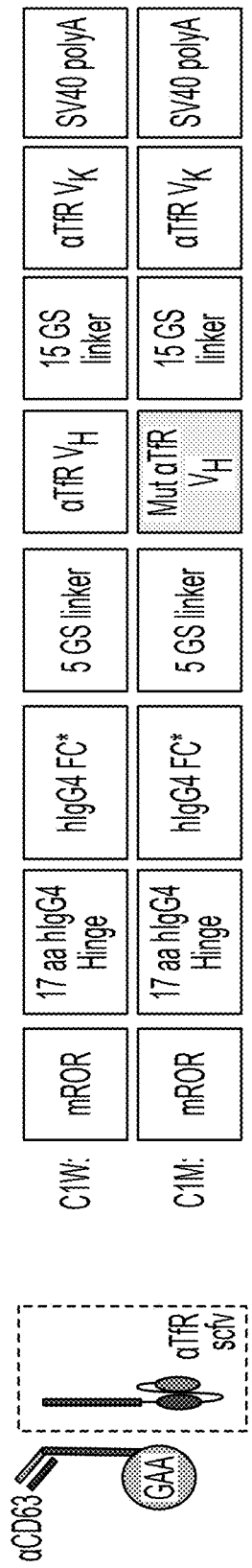

| | | | | | | | | | | | |
|---|---|---|---|---|---|---|---|---|---|---|---|
| C3W1: | mROR | αCD63 V_H | 15 GS linker | αCD63 V_K | 5 GS linker | Δ42 GAA | 5 GS linker | αTfR V_H | 15 GS linker | αTfR V_K | SV40 polyA |
| C3M1: | mROR | αCD63 V_H | 15 GS linker | αCD63 V_K | 5 GS linker | Δ42 GAA | 5 GS linker | Mut αTfR V_H | 15 GS linker | αTfR V_K | SV40 polyA |
| C3W2: | mROR | αCD63 V_H | 15 GS linker | αCD63 V_K | 5 GS linker | Δ42 GAA | 10 GS linker | αTfR V_H | 15 GS linker | αTfR V_K | SV40 polyA |
| C3M2: | mROR | αCD63 V_H | 15 GS linker | αCD63 V_K | 5 GS linker | Δ42 GAA | 10 GS linker | Mut αTfR V_H | 15 GS linker | αTfR V_K | SV40 polyA |

Construct 3:

FIGURE 1F

| | | | | | | | | | | |
|---|---|---|---|---|---|---|---|---|---|---|
| C4W1: | mROR | αCD63 V_H | 15 GS linker | αCD63 V_K | 5 GS linker | αTfR V_H | 15 GS linker | αTfR V_K | 15 GS linker | Δ42 GAA | SV40 polyA |
| C4M1: | mROR | αCD63 V_H | 15 GS linker | αCD63 V_K | 5 GS linker | Mut αTfR V_H | 15 GS linker | αTfR V_K | 15 GS linker | Δ42 GAA | SV40 polyA |
| C4W2: | mROR | αCD63 V_H | 15 GS linker | αCD63 V_K | 10 GS linker | αTfR V_H | 15 GS linker | αTfR V_K | 10 GS linker | Δ42 GAA | SV40 polyA |
| C4M2: | mROR | αCD63 V_H | 15 GS linker | αCD63 V_K | 10 GS linker | Mut αTfR V_H | 15 GS linker | αTfR V_K | 10 GS linker | Δ42 GAA | SV40 polyA |
| C4W3: | mROR | αCD63 V_H | 15 GS linker | αCD63 V_K | 15 GS linker | αTfR V_H | 15 GS linker | αTfR V_K | 15 GS linker | Δ42 GAA | SV40 polyA |
| C4M3: | mROR | αCD63 V_H | 15 GS linker | αCD63 V_K | 15 GS linker | Mut αTfR V_H | 15 GS linker | αTfR V_K | 15 GS linker | Δ42 GAA | SV40 polyA |

Construct 4: 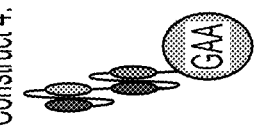

FIGURE 1G

| | | | | | | | |
|---|---|---|---|---|---|---|---|
| C6W1: | mROR | αTfR V$_H$ | 15 GS linker | αTfR V$_K$ | 5 GS linker | Δ42 GAA | SV40 polyA |
| C6M1: | mROR | Mut αTfR V$_H$ | 15 GS linker | αTfR V$_K$ | 5 GS linker | Δ42 GAA | SV40 polyA |
| C6W2: | mROR | αTfR V$_H$ | 15 GS linker | αTfR V$_K$ | 10 GS linker | Δ42 GAA | SV40 polyA |
| C6M2: | mROR | Mut αTfR V$_H$ | 15 GS linker | αTfR V$_K$ | 10 GS linker | Δ42 GAA | SV40 polyA |
| C6W3: | mROR | αTfR V$_H$ | 15 GS linker | αTfR V$_K$ | 15 GS linker | Δ42 GAA | SV40 polyA |
| C6M3: | mROR | Mut αTfR V$_H$ | 15 GS linker | αTfR V$_K$ | 15 GS linker | Δ42 GAA | SV40 polyA |

Construct 6: 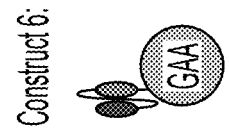

SEQUENCE LISTING

<160> NUMBER OF SEQ ID NOS: 13

<210> SEQ ID NO 1
<211> LENGTH: 952
<212> TYPE: PRT
<213> ORGANISM: Homo sapiens

<400> SEQUENCE: 1

```
Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45
```

```
Leu Glu Glu Thr His Pro Ala His Gln Gln Gly Ala Ser Arg Pro Gly
 50                  55                  60

Pro Arg Asp Ala Gln Ala His Pro Gly Arg Pro Arg Ala Val Pro Thr
 65                  70                  75                  80

Gln Cys Asp Val Pro Asn Ser Arg Phe Asp Cys Ala Pro Asp Lys
                 85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
            115                 120                 125

Phe Pro Pro Ser Tyr Pro Ser Tyr Lys Leu Glu Asn Leu Ser Ser Ser
130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
            195                 200                 205

Tyr Ser Val Glu Phe Ser Glu Glu Pro Phe Gly Val Ile Val Arg Arg
210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
            275                 280                 285

Ala Asn Leu Tyr Gly Ser His Pro Phe Tyr Leu Ala Leu Glu Asp Gly
290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
            355                 360                 365

Leu Gly Phe His Leu Cys Arg Trp Gly Tyr Ser Ser Thr Ala Ile Thr
370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
            435                 440                 445

Ser Gly Pro Ala Gly Ser Tyr Arg Pro Tyr Asp Glu Gly Leu Arg Arg
450                 455                 460

Gly Val Phe Ile Thr Asn Glu Thr Gly Gln Pro Leu Ile Gly Lys Val
```

-continued

```
                465                 470                 475                 480
        Trp Pro Gly Ser Thr Ala Phe Pro Asp Phe Thr Asn Pro Thr Ala Leu
                            485                 490                 495

Ala Trp Trp Glu Asp Met Val Ala Glu Phe His Asp Gln Val Pro Phe
                            500                 505                 510

Asp Gly Met Trp Ile Asp Met Asn Glu Pro Ser Asn Phe Ile Arg Gly
                            515                 520                 525

Ser Glu Asp Gly Cys Pro Asn Asn Glu Leu Glu Asn Pro Pro Tyr Val
                            530                 535                 540

Pro Gly Val Val Gly Gly Thr Leu Gln Ala Ala Thr Ile Cys Ala Ser
        545                 550                 555                 560

Ser His Gln Phe Leu Ser Thr His Tyr Asn Leu His Asn Leu Tyr Gly
                            565                 570                 575

Leu Thr Glu Ala Ile Ala Ser His Arg Ala Leu Val Lys Ala Arg Gly
                            580                 585                 590

Thr Arg Pro Phe Val Ile Ser Arg Ser Thr Phe Ala Gly His Gly Arg
                            595                 600                 605

Tyr Ala Gly His Trp Thr Gly Asp Val Trp Ser Ser Trp Glu Gln Leu
                            610                 615                 620

Ala Ser Ser Val Pro Glu Ile Leu Gln Phe Asn Leu Leu Gly Val Pro
        625                 630                 635                 640

Leu Val Gly Ala Asp Val Cys Gly Phe Leu Gly Asn Thr Ser Glu Glu
                            645                 650                 655

Leu Cys Val Arg Trp Thr Gln Leu Gly Ala Phe Tyr Pro Phe Met Arg
                            660                 665                 670

Asn His Asn Ser Leu Leu Ser Leu Pro Gln Glu Pro Tyr Ser Phe Ser
                            675                 680                 685

Glu Pro Ala Gln Gln Ala Met Arg Lys Ala Leu Thr Leu Arg Tyr Ala
                            690                 695                 700

Leu Leu Pro His Leu Tyr Thr Leu Phe His Gln Ala His Val Ala Gly
        705                 710                 715                 720

Glu Thr Val Ala Arg Pro Leu Phe Leu Glu Phe Pro Lys Asp Ser Ser
                            725                 730                 735

Thr Trp Thr Val Asp His Gln Leu Leu Trp Gly Glu Ala Leu Leu Ile
                            740                 745                 750

Thr Pro Val Leu Gln Ala Gly Lys Ala Glu Val Thr Gly Tyr Phe Pro
                            755                 760                 765

Leu Gly Thr Trp Tyr Asp Leu Gln Thr Val Pro Val Glu Ala Leu Gly
        770                 775                 780

Ser Leu Pro Pro Pro Ala Ala Pro Arg Glu Pro Ala Ile His Ser
        785                 790                 795                 800

Glu Gly Gln Trp Val Thr Leu Pro Ala Pro Leu Asp Thr Ile Asn Val
                            805                 810                 815

His Leu Arg Ala Gly Tyr Ile Ile Pro Leu Gln Gly Pro Gly Leu Thr
                            820                 825                 830

Thr Thr Glu Ser Arg Gln Gln Pro Met Ala Leu Ala Val Ala Leu Thr
                            835                 840                 845

Lys Gly Gly Glu Ala Arg Gly Glu Leu Phe Trp Asp Asp Gly Glu Ser
                            850                 855                 860

Leu Glu Val Leu Glu Arg Gly Ala Tyr Thr Gln Val Ile Phe Leu Ala
        865                 870                 875                 880

Arg Asn Asn Thr Ile Val Asn Glu Leu Val Arg Val Thr Ser Glu Gly
                            885                 890                 895
```

```
Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
            915                 920                 925

Ser Pro Asp Thr Lys Val Leu Asp Ile Cys Val Ser Leu Leu Met Gly
            930                 935                 940

Glu Gln Phe Leu Val Ser Trp Cys
945                 950

<210> SEQ ID NO 2
<211> LENGTH: 245
<212> TYPE: PRT
<213> ORGANISM: Artificial
<220> FEATURE:
<223> OTHER INFORMATION: synthetic

<400> SEQUENCE: 2

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Ser Trp Val Arg Gln Thr Pro Glu Lys Arg Leu Glu Trp Val
        35                  40                  45

Ala Tyr Ile Ser Ser Ser Gly Ser Thr Tyr Tyr Ser Asp Thr Val
    50                  55                  60

Lys Gly Gln Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Arg Glu Asp Tyr Asp Gly Arg Leu Thr Tyr Trp Gly Gln Gly
            100                 105                 110

Thr Leu Val Thr Ile Ser Ala Gly Gly Ser Gly Gly Gly Ser Gly
            115                 120                 125

Gly Gly Ser Gly Gly Asp Ile Val Leu Thr Gln Ser Pro Ala Ser
    130                 135                 140

Leu Ala Val Ser Leu Gly Gln Arg Ala Thr Ile Ser Cys Arg Ala Ser
145                 150                 155                 160

Lys Ser Val Ser Thr Ser Gly Tyr Ser Tyr Met Asn Trp Tyr Gln Gln
                165                 170                 175

Lys Pro Gly Gln Pro Pro Lys Val Leu Ile Tyr Leu Ala Ser Lys Leu
            180                 185                 190

Glu Ser Gly Val Pro Ala Arg Phe Ser Gly Ser Gly Ser Gly Thr Asp
        195                 200                 205

Phe Thr Leu Asn Ile His Pro Val Glu Glu Asp Ala Ala Thr Tyr
    210                 215                 220

Tyr Cys Gln His Ser Arg Glu Leu Pro Tyr Thr Phe Gly Gly Gly Thr
225                 230                 235                 240

Lys Leu Glu Ile Lys
                245

<210> SEQ ID NO 3
<211> LENGTH: 21
<212> TYPE: DNA
<213> ORGANISM: Artificial
<220> FEATURE:
<223> OTHER INFORMATION: synthetic
```

```
<400> SEQUENCE: 3 ggaacccta gtgatggagt t                                                      21

<210> SEQ ID NO 4
<211> LENGTH: 16
<212> TYPE: DNA
<213> ORGANISM: Artificial
<220> FEATURE:
<223> OTHER INFORMATION: synthetic

<400> SEQUENCE: 4
cggcctcagt gagcga                                                           16

<210> SEQ ID NO 5
<211> LENGTH: 21
<212> TYPE: DNA
<213> ORGANISM: Artificial
<220> FEATURE:
<223> OTHER INFORMATION: synthetic

<400> SEQUENCE: 5
cactccctct ctgcgcgctc g                                                     21

<210> SEQ ID NO 6
<211> LENGTH: 141
<212> TYPE: DNA
<213> ORGANISM: Artificial
<220> FEATURE:
<223> OTHER INFORMATION: synthetic

<400> SEQUENCE: 6
cctgcaggca gctgcgcgct cgctcgctca ctgaggccgc ccgggcaaag cccgggcgtc           60
gggcgacctt tggtcgcccg gcctcagtga gcgagcgagc gcgcagagag ggagtggcca          120
actccatcac tagggggttcc t                                                   141

<210> SEQ ID NO 7
<211> LENGTH: 141
<212> TYPE: DNA
<213> ORGANISM: Artificial
<220> FEATURE:
<223> OTHER INFORMATION: synthetic

<400> SEQUENCE: 7
aggaacccct agtgatggag ttggccactc cctctctgcg cgctcgctcg ctcactgagg           60
ccgggcgacc aaaggtcgcc cgacgcccgg gctttgcccg gcggcctca gtgagcgagc           120 gagcgcgcag ctgcctgcag g                                                    141

<210> SEQ ID NO 8
<211> LENGTH: 224
<212> TYPE: DNA
<213> ORGANISM: Artificial
<220> FEATURE:
<223> OTHER INFORMATION: synthetic

<400> SEQUENCE: 8
gtctgtctgc acatttcgta gagcgagtgt tccgatactc taatctccct aggcaaggtt           60
catatttgtg taggttactt attctccttt tgttgactaa gtcaataatc agaatcagca          120
ggtttggagt cagcttggca gggatcagca gcctgggttg aaggaggggg gtataaaagc          180 ccttcacca ggagaagccg tcacacagat ccacaagctc ctga                            224
```

-continued

```
<210> SEQ ID NO 9
<211> LENGTH: 72
<212> TYPE: DNA
<213> ORGANISM: Artificial
<220> FEATURE:
<223> OTHER INFORMATION: synthetic

<400> SEQUENCE: 9
gggggaggct gctggtgaat attaaccaag gtcaccccag ttatcggagg agcaaacagg    60
ggctaagtcc ac                                                       72

<210> SEQ ID NO 10
<211> LENGTH: 1133
<212> TYPE: PRT
<213> ORGANISM: Artificial
<220> FEATURE:
<223> OTHER INFORMATION: synthetic

<400> SEQUENCE: 10
```

| | | | | | | | | | | | | | | |
|---|---|---|---|---|---|---|---|---|---|---|---|---|---|---|
| Glu | Val | Lys | Leu | Val | Glu | Ser | Gly | Gly | Gly | Leu | Val | Gln | Pro | Gly |
| 1 | | | | 5 | | | | | 10 | | | | | 15 |
| Ser | Leu | Lys | Leu | Ser | Cys | Ala | Thr | Ser | Gly | Phe | Thr | Phe | Ser | Asp | Tyr |
| | | | 20 | | | | | 25 | | | | | 30 | | |
| Tyr | Met | Ser | Trp | Val | Arg | Gln | Thr | Pro | Glu | Lys | Arg | Leu | Glu | Trp | Val |
| | | 35 | | | | | 40 | | | | | 45 | | | |
| Ala | Tyr | Ile | Ser | Ser | Ser | Gly | Gly | Ser | Thr | Tyr | Tyr | Ser | Asp | Thr | Val |
| 50 | | | | | 55 | | | | | 60 | | | | | |
| Lys | Gly | Gln | Phe | Thr | Ile | Ser | Arg | Asp | Asn | Ala | Lys | Asn | Thr | Leu | Tyr |
| 65 | | | | | 70 | | | | | 75 | | | | | 80 |
| Leu | Gln | Met | Ser | Arg | Leu | Lys | Ser | Glu | Asp | Thr | Ala | Met | Tyr | Tyr | Cys |
| | | | | 85 | | | | | 90 | | | | | 95 | |
| Ala | Arg | Arg | Glu | Asp | Tyr | Asp | Gly | Arg | Leu | Thr | Tyr | Trp | Gly | Gln | Gly |
| | | | 100 | | | | | 105 | | | | | 110 | | |
| Thr | Leu | Val | Thr | Ile | Ser | Ala | Gly | Gly | Ser | Gly | Gly | Gly | Ser | Gly |
| | | | 115 | | | | | 120 | | | | | 125 | | |
| Gly | Gly | Gly | Ser | Gly | Gly | Asp | Ile | Val | Leu | Thr | Gln | Ser | Pro | Ala | Ser |
| | 130 | | | | | 135 | | | | | 140 | | | | |
| Leu | Ala | Val | Ser | Leu | Gly | Gln | Arg | Ala | Thr | Ile | Ser | Cys | Arg | Ala | Ser |
| 145 | | | | | 150 | | | | | 155 | | | | | 160 |
| Lys | Ser | Val | Ser | Thr | Ser | Gly | Tyr | Ser | Tyr | Met | Asn | Trp | Tyr | Gln | Gln |
| | | | | 165 | | | | | 170 | | | | | 175 | |
| Lys | Pro | Gly | Gln | Pro | Pro | Lys | Val | Leu | Ile | Tyr | Leu | Ala | Ser | Lys | Leu |
| | | | 180 | | | | | 185 | | | | | 190 | | |
| Glu | Ser | Gly | Val | Pro | Ala | Arg | Phe | Ser | Gly | Ser | Gly | Ser | Gly | Thr | Asp |
| | | | 195 | | | | | 200 | | | | | 205 | | |
| Phe | Thr | Leu | Asn | Ile | His | Pro | Val | Glu | Glu | Glu | Asp | Ala | Ala | Thr | Tyr |
| | 210 | | | | | 215 | | | | | 220 | | | | |
| Tyr | Cys | Gln | His | Ser | Arg | Glu | Leu | Pro | Tyr | Thr | Phe | Gly | Gly | Gly | Thr |
| 225 | | | | | 230 | | | | | 235 | | | | | 240 |
| Lys | Leu | Glu | Ile | Lys | Gly | Gly | Gly | Gly | Ser | Ala | His | Pro | Gly | Arg | Pro |
| | | | | 245 | | | | | 250 | | | | | 255 | |
| Arg | Ala | Val | Pro | Thr | Gln | Cys | Asp | Val | Pro | Asn | Ser | Arg | Phe | Asp |
| | | | 260 | | | | | 265 | | | | | 270 | | |
| Cys | Ala | Pro | Asp | Lys | Ala | Ile | Thr | Gln | Glu | Gln | Cys | Glu | Ala | Arg | Gly |
| | | | 275 | | | | | 280 | | | | | 285 | | |
| Cys | Cys | Tyr | Ile | Pro | Ala | Lys | Gln | Gly | Leu | Gln | Gly | Ala | Gln | Met | Gly |
| | 290 | | | | | 295 | | | | | 300 | | | | |

-continued

```
Gln Pro Trp Cys Phe Phe Pro Pro Ser Tyr Pro Ser Tyr Lys Leu Glu
305                 310                 315                 320

Asn Leu Ser Ser Ser Glu Met Gly Tyr Thr Ala Thr Leu Thr Arg Thr
            325                 330                 335

Thr Pro Thr Phe Phe Pro Lys Asp Ile Leu Thr Leu Arg Leu Asp Val
            340                 345                 350

Met Met Glu Thr Glu Asn Arg Leu His Phe Thr Ile Lys Asp Pro Ala
            355                 360                 365

Asn Arg Arg Tyr Glu Val Pro Leu Glu Thr Pro His Val His Ser Arg
            370                 375                 380

Ala Pro Ser Pro Leu Tyr Ser Val Glu Phe Ser Glu Glu Pro Phe Gly
385                 390                 395                 400

Val Ile Val Arg Arg Gln Leu Asp Gly Arg Val Leu Leu Asn Thr Thr
                405                 410                 415

Val Ala Pro Leu Phe Phe Ala Asp Gln Phe Leu Gln Leu Ser Thr Ser
            420                 425                 430

Leu Pro Ser Gln Tyr Ile Thr Gly Leu Ala Glu His Leu Ser Pro Leu
        435                 440                 445

Met Leu Ser Thr Ser Trp Thr Arg Ile Thr Leu Trp Asn Arg Asp Leu
450                 455                 460

Ala Pro Thr Pro Gly Ala Asn Leu Tyr Gly Ser His Pro Phe Tyr Leu
465                 470                 475                 480

Ala Leu Glu Asp Gly Gly Ser Ala His Gly Val Phe Leu Leu Asn Ser
                485                 490                 495

Asn Ala Met Asp Val Val Leu Gln Pro Ser Pro Ala Leu Ser Trp Arg
            500                 505                 510

Ser Thr Gly Gly Ile Leu Asp Val Tyr Ile Phe Leu Gly Pro Glu Pro
        515                 520                 525

Lys Ser Val Val Gln Gln Tyr Leu Asp Val Val Gly Tyr Pro Phe Met
530                 535                 540

Pro Pro Tyr Trp Gly Leu Gly Phe His Leu Cys Arg Trp Gly Tyr Ser
545                 550                 555                 560

Ser Thr Ala Ile Thr Arg Gln Val Val Glu Asn Met Thr Arg Ala His
                565                 570                 575

Phe Pro Leu Asp Val Gln Trp Asn Asp Leu Asp Tyr Met Asp Ser Arg
            580                 585                 590

Arg Asp Phe Thr Phe Asn Lys Asp Gly Phe Arg Asp Phe Pro Ala Met
            595                 600                 605

Val Gln Glu Leu His Gln Gly Gly Arg Arg Tyr Met Met Ile Val Asp
            610                 615                 620

Pro Ala Ile Ser Ser Ser Gly Pro Ala Gly Ser Tyr Arg Pro Tyr Asp
625                 630                 635                 640

Glu Gly Leu Arg Arg Gly Val Phe Ile Thr Asn Glu Thr Gly Gln Pro
                645                 650                 655

Leu Ile Gly Lys Val Trp Pro Gly Ser Thr Ala Phe Pro Asp Phe Thr
            660                 665                 670

Asn Pro Thr Ala Leu Ala Trp Trp Glu Asp Met Val Ala Glu Phe His
            675                 680                 685

Asp Gln Val Pro Phe Asp Gly Met Trp Ile Asp Met Asn Glu Pro Ser
            690                 695                 700

Asn Phe Ile Arg Gly Ser Glu Asp Gly Cys Pro Asn Asn Glu Leu Glu
705                 710                 715                 720
```

```
Asn Pro Pro Tyr Val Pro Gly Val Val Gly Thr Leu Gln Ala Ala
            725             730                 735

Thr Ile Cys Ala Ser Ser His Gln Phe Leu Ser Thr His Tyr Asn Leu
            740                 745                 750

His Asn Leu Tyr Gly Leu Thr Glu Ala Ile Ala Ser His Arg Ala Leu
            755                 760                 765

Val Lys Ala Arg Gly Thr Arg Pro Phe Val Ile Ser Arg Ser Thr Phe
        770                 775                 780

Ala Gly His Gly Arg Tyr Ala Gly His Trp Thr Gly Asp Val Trp Ser
785                 790                 795                 800

Ser Trp Glu Gln Leu Ala Ser Ser Val Pro Glu Ile Leu Gln Phe Asn
                805                 810                 815

Leu Leu Gly Val Pro Leu Val Gly Ala Asp Val Cys Gly Phe Leu Gly
                820                 825                 830

Asn Thr Ser Glu Glu Leu Cys Val Arg Trp Thr Gln Leu Gly Ala Phe
                835                 840                 845

Tyr Pro Phe Met Arg Asn His Asn Ser Leu Leu Ser Leu Pro Gln Glu
        850                 855                 860

Pro Tyr Ser Phe Ser Glu Pro Ala Gln Gln Ala Met Arg Lys Ala Leu
865                 870                 875                 880

Thr Leu Arg Tyr Ala Leu Leu Pro His Leu Tyr Thr Leu Phe His Gln
                885                 890                 895

Ala His Val Ala Gly Glu Thr Val Ala Arg Pro Leu Phe Leu Glu Phe
                900                 905                 910

Pro Lys Asp Ser Ser Thr Trp Thr Val Asp His Gln Leu Leu Trp Gly
        915                 920                 925

Glu Ala Leu Leu Ile Thr Pro Val Leu Gln Ala Gly Lys Ala Glu Val
        930                 935                 940

Thr Gly Tyr Phe Pro Leu Gly Thr Trp Tyr Asp Leu Gln Thr Val Pro
945                 950                 955                 960

Val Glu Ala Leu Gly Ser Leu Pro Pro Pro Ala Ala Pro Arg Glu
                965                 970                 975

Pro Ala Ile His Ser Glu Gly Gln Trp Val Thr Leu Pro Ala Pro Leu
                980                 985                 990

Asp Thr Ile Asn Val His Leu Arg  Ala Gly Tyr Ile Ile  Pro Leu Gln
        995                  1000                1005

Gly Pro  Gly Leu Thr Thr Thr  Glu Ser Arg Gln Gln  Pro Met Ala
    1010                 1015                 1020

Leu Ala  Val Ala Leu Thr Lys  Gly Gly Glu Ala Arg  Gly Glu Leu
    1025                 1030                 1035

Phe Trp  Asp Asp Gly Glu Ser  Leu Glu Val Leu Glu  Arg Gly Ala
    1040                 1045                 1050

Tyr Thr  Gln Val Ile Phe Leu  Ala Arg Asn Asn Thr  Ile Val Asn
    1055                 1060                 1065

Glu Leu  Val Arg Val Thr Ser  Glu Gly Ala Gly Leu  Gln Leu Gln
    1070                 1075                 1080

Lys Val  Thr Val Leu Gly Val  Ala Thr Ala Pro Gln  Gln Val Leu
    1085                 1090                 1095

Ser Asn  Gly Val Pro Val Ser  Asn Phe Thr Tyr Ser  Pro Asp Thr
    1100                 1105                 1110

Lys Val  Leu Asp Ile Cys Val  Ser Leu Leu Met Gly  Glu Gln Phe
    1115                 1120                 1125

Leu Val  Ser Trp Cys
```

<210> SEQ ID NO 11
<211> LENGTH: 3489
<212> TYPE: DNA
<213> ORGANISM: Artificial
<220> FEATURE:
<223> OTHER INFORMATION: synthetic

<400> SEQUENCE: 11

| | | | | | |
|---|---|---|---|---|---|
| atgcacagac | ctagacgtcg | tggaactcgt | ccacctccac | tggcactgct | cgctgctctc | 60 |
| ctcctggctg | cacgtggtgc | tgatgcagaa | gtgaagctgg | tggagtctgg | ggaggctta | 120 |
| gtgcagcctg | agggtccct | gaaactctcc | tgtgcaacct | ctggattcac | tttcagtgac | 180 |
| tattacatgt | cttgggttcg | ccagactcca | gagaagaggc | tggagtgggt | cgcatatatt | 240 |
| agtagtagtg | gtggtagcac | ctattattca | gacactgtaa | agggccaatt | caccatctcc | 300 |
| agagacaatg | ccaagaacac | cctgtacctg | caaatgagcc | gtctgaagtc | tgaggacaca | 360 |
| gccatgtatt | actgtgcaag | acgagaagat | tacgacggaa | gacttactta | ctggggccaa | 420 |
| gggactctgg | tcaccatctc | tgcaggagga | agtggtggag | cgggtcagg | aggtggcggg | 480 |
| agcggcggtg | acattgtgct | gacacagtct | cctgcttcct | tagctgtatc | tctggggcag | 540 |
| agggccacca | tctcctgcag | ggccagcaaa | agtgtcagta | catctggtta | tagttatatg | 600 |
| aactggtacc | aacagaaacc | aggacagcca | cccaaagtcc | tcatctatct | tgcatccaaa | 660 |
| ctagaatctg | gggtccctgc | caggttcagt | ggcagtgggt | cagggacaga | cttcaccctc | 720 |
| aacatccatc | ctgtggagga | ggaggatgct | gcaacctatt | actgtcagca | cagtagggag | 780 |
| cttccgtaca | cgttcggagg | ggggaccaaa | ctggaaataa | aggtggtgg | cggttcagca | 840 |
| cacccccggcc | gtcccagagc | agtgcccaca | cagtgcgacg | tcccccccaa | cagccgcttc | 900 |
| gattgcgccc | ctgacaaggc | catcacccag | gaacagtgcg | aggcccgcgg | ctgttgctac | 960 |
| atccctgcaa | gcagggggct | gcagggagcc | cagatggggc | agcccctggtg | cttcttccca | 1020 |
| cccagctacc | ccagctacaa | gctggagaac | ctgagctcct | ctgaaatggg | ctacacggcc | 1080 |
| accctgaccc | gtaccacccc | caccttcttc | cccaaggaca | tcctgacccct | gcggctggac | 1140 |
| gtgatgatgg | agactgagaa | ccgcctccac | ttcacgatca | agatccagc | taacaggcgc | 1200 |
| tacgaggtgc | ccttggagac | cccgcatgtc | cacagccggg | caccgtcccc | actctacagc | 1260 |
| gtggagttct | ccgaggagcc | cttcggggtg | atcgtgcgcc | ggcagctgga | cggccgcgtg | 1320 |
| ctgctgaaca | cgacggtggc | gcccctgttc | tttgcggacc | agttccttca | gctgtccacc | 1380 |
| tcgctgccct | cgcagtatat | cacaggcctc | gccgagcacc | tcagtcccct | gatgctcagc | 1440 |
| accagctgga | ccaggatcac | cctgtggaac | cgggaccttg | cgcccacgcc | cggtgcgaac | 1500 |
| ctctacgggt | ctcacccttt | ctacctggcg | ctggaggacg | gcgggtcggc | acacgggtg | 1560 |
| ttcctgctaa | acagcaatgc | catggatgtg | gtcctgcagc | cgagccctgc | ccttagctgg | 1620 |
| aggtcgacag | gtgggatcct | ggatgtctac | atcttcctgg | gcccagagcc | caagagcgtg | 1680 |
| gtgcagcagt | acctggacgt | tgtgggatac | ccgttcatgc | cgccatactg | gggcctgggc | 1740 |
| ttccacctgt | gccgctgggg | ctactcctcc | accgctatca | cccgccaggt | ggtggagaac | 1800 |
| atgaccaggg | cccacttccc | cctggacgtc | cagtggaacg | acctggacta | catggactcc | 1860 |
| cggagggact | tcacgttcaa | caaggatggc | ttcgggact | tcccggccat | ggtgcaggag | 1920 |
| ctgcaccagg | gcggccggcg | ctacatgatg | atcgtggatc | ctgccatcag | cagctcgggc | 1980 |
| cctgccggga | gctacaggcc | ctacgacgag | ggtctgcgga | gggggttt | catcaccaac | 2040 |

```
gagaccggcc agccgctgat tgggaaggta tggcccgggt ccactgcctt ccccgacttc   2100
accaacccca cagccctggc ctggtgggag gacatggtgg ctgagttcca tgaccaggtg   2160
cccttcgacg gcatgtggat tgacatgaac gagccttcca acttcatcag gggctctgag   2220
gacggctgcc ccaacaatga gctggagaac ccacctacg tgcctggggt ggttgggggg   2280
accctccagg cggccaccat ctgtgcctcc agccaccagt ttctctccac acactacaac   2340
ctgcacaacc tctacggcct gaccgaagcc atcgcctccc acagggcgct ggtgaaggct   2400
cgggggacac gcccatttgt gatctcccgc tcgacctttg ctggccacgg ccgatacgcc   2460
ggccactgga cggggacgt gtggagctcc tgggagcagc tcgcctcctc cgtgccagaa   2520
atcctgcagt ttaacctgct gggggtgcct ctggtcgggg ccgacgtctg cggcttcctg   2580
ggcaacacct cagaggagct gtgtgtgcgc tggacccagc tgggggcctt ctaccccttc   2640
atgcggaacc acaacagcct gctcagtctg ccccaggagc cgtacagctt cagcgagccg   2700
gcccagcagg ccatgaggaa ggccctcacc ctgcgctacg cactcctccc ccacctctac   2760
acactgttcc accaggccca cgtcgcgggg gagaccgtgg cccggcccct cttcctggag   2820
ttccccaagg actctagcac ctggactgtg gaccaccagc cctgtgggg ggaggccctg   2880 ctcatcaccc cagtgctcca ggccgggaag gccgaagtga ctggctactt ccccttgggc   2940
acatggtacg acctgcagac ggtgccagta gaggcccttg gcagcctccc accccacct   3000 gcagctcccc gtgagccagc catccacagc gaggggcagt gggtgacgct gccggccccc   3060
ctggacacca tcaacgtcca cctccgggct gggtacatca tccccctgca gggccctggc   3120
ctcacaacca cagagtcccg ccagcagccc atggccctgg ctgtggccct gaccaagggt   3180
ggggaggccc gaggggagct gttctgggac gatggagaga gcctggaagt gctggagcga   3240
ggggcctaca cacaggtcat cttcctggcc aggaataaca cgatcgtgaa tgagctggta   3300
cgtgtgacca gtgagggagc tggcctgcag ctgcagaagg tgactgtcct gggcgtggcc   3360
acggcgcccc agcaggtcct ctccaacggt gtccctgtct ccaacttcac ctacagcccc   3420
gacaccaagg tcctggacat ctgtgtctcg ctgttgatgg gagagcagtt tctcgtcagc   3480
tggtgttag                                                          3489

<210> SEQ ID NO 12
<211> LENGTH: 2859
<212> TYPE: DNA
<213> ORGANISM: Homo sapiens

<400> SEQUENCE: 12
atgggagtga ggcacccgcc ctgctcccac cggctcctgg ccgtctgcgc cctcgtgtcc     60
ttggcaaccg ctgcactcct ggggcacatc ctactccatg atttcctgct ggttccccga    120
gagctgagtg gctcctcccc agtcctggag gagactcacc cagctcacca gcagggagcc    180
agcagaccag gccccgggga tgcccaggca caccccggcc gtcccagagc agtgcccaca    240
cagtgcgacg tcccccccaa cagccgcttc gattgcgccc ctgacaaggc catcacccag    300
gaacagtgcg aggcccgcgg ctgttgctac atccctgcaa agcagggggct gcagggagcc    360 cagatggggc agccctggtg cttcttccca cccagctacc ccagctacaa gctggagaac    420
ctgagctcct ctgaaatggg ctacacggcc accctgaccc gtaccacccc caccttcttc    480
cccaaggaca tcctgacccct gcggctggac gtgatgatgg agactgagaa ccgcctccac    540
ttcacgatca aagatccagc taacaggcgc tacgaggtgc ccttggagac cccgcatgtc    600
```

| | |
|---|---|
| cacagccggg caccgtcccc actctacagc gtggagttct ccgaggagcc cttcggggtg | 660 |
| atcgtgcgcc ggcagctgga cggccgcgtg ctgctgaaca cgacggtggc gcccctgttc | 720 |
| tttgcggacc agttccttca gctgtccacc tcgctgccct cgcagtatat cacaggcctc | 780 |
| gccgagcacc tcagtcccct gatgctcagc accagctgga ccaggatcac cctgtggaac | 840 |
| cgggaccttg cgcccacgcc cggtgcgaac ctctacgggt ctcacccttt ctacctggcg | 900 |
| ctggaggacg gcgggtcggc acacggggtg ttcctgctaa acagcaatgc catggatgtg | 960 |
| gtcctgcagc cgagccctgc ccttagctgg aggtcgacag gtgggatcct ggatgtctac | 1020 |
| atcttcctgg gcccagagcc caagagcgtg gtgcagcagt acctggacgt tgtgggatac | 1080 |
| ccgttcatgc cgccatactg gggcctgggc ttccacctgt gccgctgggg ctactcctcc | 1140 |
| accgctatca cccgccaggt ggtggagaac atgaccaggg cccacttccc cctggacgtc | 1200 |
| cagtggaacg acctggacta catggactcc cggagggact tcacgttcaa caaggatggc | 1260 |
| ttccgggact ccccgccat ggtgcaggag ctgcaccagg cggccggcg ctacatgatg | 1320 |
| atcgtggatc ctgccatcag cagctcgggc cctgccggga gctacaggcc ctacgacgag | 1380 |
| ggtctgcgga gggggttttt catcaccaac gagaccggcc agccgctgat tgggaaggta | 1440 |
| tggcccgggt ccactgcctt ccccgacttc accaacccca cagccctggc ctggtgggag | 1500 |
| gacatggtgg ctgagttcca tgaccaggtg cccttcgacg gcatgtggat tgacatgaac | 1560 |
| gagccttcca acttcatcag gggctctgag gacggctgcc ccaacaatga gctggagaac | 1620 |
| ccaccctacg tgcctggggt ggttgggggg accctccagg cggccaccat ctgtgcctcc | 1680 |
| agccaccagt ttctctccac acactacaac ctgcacaacc tctacggcct gaccgaagcc | 1740 |
| atcgcctccc acagggcgct ggtgaaggct cggggggacac gcccatttgt gatctcccgc | 1800 |
| tcgacctttg ctgccacgg ccgatacgcc ggccactgga cggggacgt gtggagctcc | 1860 |
| tgggagcagc tcgcctcctc cgtgccagaa atcctgcagt ttaacctgct gggggtgcct | 1920 |
| ctggtcgggg ccgacgtctg cggcttcctg ggcaacacct cagaggagct gtgtgtgcgc | 1980 |
| tggacccagc tgggggcctt ctaccccttc atgcggaacc acaacagcct gctcagtctg | 2040 |
| ccccaggagc cgtacagctt cagcgagccg gcccagcagg ccatgaggaa ggccctcacc | 2100 |
| ctgcgctacg cactcctccc ccacctctac acactgttcc accaggccca cgtcgcgggg | 2160 |
| gagaccgtgg cccggcccct cttcctggag ttccccaagg actctagcac ctggactgtg | 2220 |
| gaccaccagc tcctgtgggg ggaggccctg ctcatcaccc cagtgctcca ggccgggaag | 2280 |
| gccgaagtga ctggctactt ccccttgggc acatggtacg acctgcagac ggtgccagta | 2340 |
| gaggcccttg gcagcctccc accccacct gcagctcccc gtgagccagc catccacagc | 2400 |
| gaggggcagt gggtgacgct gccggccccc ctggacacca tcaacgtcca cctccgggct | 2460 |
| gggtacatca tcccctgca gggccctggc ctcacaacca cagagtcccg ccagcagccc | 2520 |
| atggccctgg ctgtggccct gaccaagggt gggaggccc gagggagct gttctgggac | 2580 |
| gatggagaga gcctggaagt gctggagcga ggggcctaca caggtcat cttcctggcc | 2640 |
| aggaataaca cgatcgtgaa tgagctggta cgtgtgacca gtgagggagc tggcctgcag | 2700 |
| ctgcagaagg tgactgtcct gggcgtggcc acggcgcccc agcaggtcct ctccaacggt | 2760 |
| gtccctgtct ccaacttcac ctacagcccc gacaccaagg tcctggacat ctgtgtctcg | 2820 |
| ctgttgatgg gagagcagtt tctcgtcagc tggtgttag | 2859 |

<210> SEQ ID NO 13
<211> LENGTH: 398

```
<212> TYPE: PRT
<213> ORGANISM: Homo sapiens

<400> SEQUENCE: 13

Leu Asp Asn Gly Leu Ala Arg Thr Pro Thr Met Gly Trp Leu His Trp
1               5                   10                  15

Glu Arg Phe Met Cys Asn Leu Asp Cys Gln Glu Glu Pro Asp Ser Cys
            20                  25                  30

Ile Ser Glu Lys Leu Phe Met Glu Met Ala Glu Leu Met Val Ser Glu
            35                  40                  45

Gly Trp Lys Asp Ala Gly Tyr Glu Tyr Leu Cys Ile Asp Asp Cys Trp
50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
                85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
            115                 120                 125

Ala Asp Trp Gly Val Asp Leu Leu Lys Phe Asp Gly Cys Tyr Cys Asp
130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
            195                 200                 205

Lys Ser Ile Leu Asp Trp Thr Ser Phe Asn Gln Glu Arg Ile Val Asp
210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
            275                 280                 285

Asn Gln Asp Pro Leu Gly Lys Gln Gly Tyr Gln Leu Arg Gln Gly Asp
290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
            355                 360                 365
```

```
Thr Ser Arg Leu Arg Ser His Ile Asn Pro Thr Gly Thr Val Leu Leu
    370                 375                 380

Gln Leu Glu Asn Thr Met Gln Met Ser Leu Lys Asp Leu Leu
385                 390                 395
```

METHODS AND COMPOSITIONS FOR THERAPEUTIC PROTEIN DELIVERY

This application is a U.S. National Phase Application filed under 35 U.S.C. § 371 of PCT Application No. PCT/US2019/017116, filed Feb. 7, 2019, which claims priority to U.S. Provisional Application Ser. No. 62/777,683, filed Dec. 10, 2018, and U.S. Provisional Application Ser. No. 62/627,721, filed Feb. 7, 2018, each of the applications of which are incorporated by reference in their entireties.

REFERENCE TO A SEQUENCE LISTING SUBMITTED AS A TEXT FILE VIA EFS-WEB

The Sequence Listing written in file 10457WO01_ST25.txt is 33.5 kilobytes, was created on Jan. 29, 2019, and is hereby incorporated by reference.

FIELD

This application is generally directed to compositions and methods for delivering a therapeutic protein to the central nervous system (CNS), in order to treat diseases and disorders that impair the CNS, such as treating lysosomal storage diseases. This application is directed to providing a therapeutically effective amount of a nucleotide composition encoding a therapeutic protein conjugated to one or more delivery domains that crosses the blood brain barrier (BBB).

BACKGROUND

Drug delivery approaches have been developed to overcome the blood brain barrier (BBB), such as nanocarriers, however have shortcomings. Carriers have exhibited instability in blood circulation and undesirable bio-distribution profile (Gelperina S, et al., 2005, *Am J Respir Crit Care Med.* 172(12):1487-90; which reference is incorporated herein in its entirety by reference). Targeting efficiencies have also been compromised depending on the trafficking mechanisms at the BBB and whether a CNS disease state has altered the integrity of the barrier. Proper selection of the targeting moiety or carrier must take into account neuroinflammatory conditions that effect these trafficking mechanisms.

Delivery of therapeutic proteins via DNA expression in the liver or other tissues has provided a convenient approach eliminating the need for bolus injection of protein and therefore lessening immunogenicity concerns. Therapeutic protein conjugated to a receptor binding protein, especially a cell specific receptor, solves the problem of targeting therapeutics to specific tissues. However, there is still a need to provide methods that efficiently provide therapeutics to the CNS.

SUMMARY

Applicants have discovered that therapeutic proteins, especially replacement enzymes, can be effectively delivered into the central nervous system when associated with a receptor binding protein and provided that the circulating blood levels achieve consistent levels over time. The multidomain therapeutic protein can be delivered to the liver via a gene therapy vector harboring the coding sequence of the therapeutic protein and binding protein complex.

In one aspect, the invention provides a method of delivering a therapeutic protein to the central nervous system (CNS) of a subject, comprising administering to the subject a nucleotide composition encoding the therapeutic protein conjugated to a cell surface receptor (CSR)-binding protein (CSR-BP) (tpCSR-BP) via a liver-targeted delivery method sufficient to provide a therapeutically effective amount of the tpCSR-BP in the CNS.

In one embodiment the CSR-BP is an antibody or antigen-binding fragment thereof that binds specifically to the CSR. In another embodiment, the therapeutic protein is a lysosomal enzyme.

In one embodiment, the enzyme has hydrolase activity, such as a glycosylase, such as a glycosidase, such as an alpha-glucosidase or alpha-galacosidase A. In one embodiment, the cell surface receptor (CSR)-binding protein (CSR-BP) is an antigen-binding protein that binds to an internalization receptor. In one embodiment, the internalization receptor is a cell-surface molecule that is endocytosed and trafficked to the lysosome. In a specific embodiment, the internalization receptor is a CD63 molecule. In one embodiment, the internalization receptor is a ITGA7 molecule. In a specific embodiment, the CSR-BP is an antibody, an antibody fragment, or a single-chain variable fragment (scFv), such as an scFv that binds CD63 or ITGA7.

In some embodiments, a multidomain therapeutic protein described herein comprises one or more delivery domain(s) and an enzyme domain, wherein the one or more delivery domain(s) binds human transferrin receptor (hTfR). In some embodiments, the multidomain therapeutic protein further comprises a second delivery domain that binds to an internalizing effector. In some embodiments, the second delivery domain binds to (i) an internalizing effector selected from the group consisting of CD63, Integrin alpha-7 (ITGA7), MHC-I, Kremen-1, Kremen-2, LRP5, LRP6, LRP8, transferrin receptor, LDL-receptor, LDL-related protein 1 receptor, ASGR1, ASGR2, amyloid precursor protein-like protein-2 (APLP2), apelin receptor (APLNR), myelin and lymphocyte protein (MAL), IGF2R, vacuolar-type H+ ATPase, diphtheria toxin receptor, folate receptor, glutamate receptors, glutathione receptor, leptin receptors, scavenger receptor A1-5 (SCARA1-5), SCARB1-3, and CD36; (ii) an internalizing effector expressed in several tissue types, optionally selected from the group consisting of CD63, MHC-I, vacuolar-type H+ ATPase, IGF2R, Integrin alpha-7 (ITGA7), LRP5, LRP6, LRP8, Kremen-2, LDL-receptor, LDL-related protein 1 receptor, amyloid precursor protein-like protein-2 (APLP2), apelin receptor (APLNR), PRLR, MAL (myelin and lymphocyte protein (MAL), diphtheria toxin receptors, HBEGF (heparin binding EGF like growth factor), glutathione receptors, glutamate receptors, leptin receptors, and folate receptors; (iii) an internalizing effector preferentially expressed by bone and/or cartilage, optionally selected from the group consisting of Collagen X, Integrin alpha 10 (ITGA10), Fibroblast growth factor receptor 3 (FGFR3), Fibroblast growth factor receptor isoform C (FGFR3C), Hyaluronan and proteoglycan link protein 1 (CRTL1), Aggrecan, Collagen II, and Kremen-1; (iv) an internalizing effector preferentially expressed by monocytes, macrophages, or microglia, optionally selected from the group consisting of scavenger receptor A1-5 (SCARA1-5), SCARB1-3, CD36, MSR1 (macrophage scavenger receptor 1), MRC1 (macrophage mannose receptor 1), VSIG4 (V-set and immunoglobulin domain-containing protein 4), CD68 (Macrosialin), and CSF1R (Macrophage colony-stimulating factor 1 receptor); (v) an internalizing effector preferentially expressed by kidney cells, optionally selected from the group consisting of CDH16 (Cadheri-16), CLDN16 (Claudn-16), KL (Klotho), PTH1R (parathyroid hormone receptor), SLC22A13 (Solute carrier family 22 member 13), SLC5A2 (Sodium/glucose cotransporter 2), and UMOD (Uromodulin). In other certain embodiments, the internalization effector is a muscle specific internalizer, such as BMPR1A (Bone morphogenetic protein receptor 1A), m-cadherin, CD9, MuSK (muscle-specific kinase), LGR4/GPR48 (G protein-coupled receptor 48), cholinergic receptor (nicotinic) alpha 1, CDH15 (Cadheri-15), ITGA7 (Integrin alpha-7), CACNG1 (L-type calcium channel subunit gamma-1), CACNA1S (L-type calcium channel subunit alpha-1S), CACNG6 (L-type calcium channel subunit gamma-6), SCN1B (Sodium channel subunit beta-1), CHRNA1 (ACh receptor subunit alpha), CHRND (ACh receptor subunit delta), LRRC14B (Leucine-rich repeat-containing protein 14B), dystroglycan (DAG1), and POPDC3 (Popeye domain-containing protein 3); (vi) an internalizing effector preferentially expressed by liver cells, optionally ASGR1 or ASGR2; (vii) an internalizing effector preferentially expressed by muscle cells, optionally selected from the group consisting of BMPR1A (Bone morphogenetic protein receptor 1A), m-cadherin, CD9, MuSK (muscle-specific kinase), LGR4/GPR48 (G protein-coupled receptor 48), cholinergic receptor (nicotinic) alpha 1, CDH15 (Cadheri-15), ITGA7 (Integrin alpha-7), CACNG1 (L-type calcium channel subunit gamma-1), CACNA1S (L-type calcium channel subunit alpha-1S), CACNG6 (L-type calcium channel subunit gamma-6), SCN1B (Sodium channel subunit beta-1), CHRNA1 (ACh receptor subunit alpha), CHRND (ACh receptor subunit delta), LRRC14B (Leucine-rich repeat-containing protein 14B), dystroglycan (DAG1), and POPDC3 (Popeye domain-containing protein 3), and/or (viii) an internalizing effector protein selected from the group consisting of ITGA7, CD9, CD63, ALPL2, MSR1, ASGR1, ASGR2, or PRLR. In some embodiments, the second delivery domain binds to the internalizing effector CD63. In some embodiments, at least one of the one or more delivery domain(s) comprises an antigen-binding protein. In some embodiments, each of the one or more delivery domain(s) comprises an antigen-binding protein. In some embodiments, at least one of the one or more delivery domain(s) comprises a single-chain variable fragment (scFv). In some embodiments, at least one of the one or more delivery domain(s) comprises a half-body. In some embodiments, the delivery domain that binds hTfR is an scFv, wherein the half-body binds CD63, wherein the enzyme domain is GAA, and wherein GAA is conjugated to the carboxy terminus of the half-body that binds CD63. In some embodiments, each of the one or more delivery domain(s) comprises an scFv. In some embodiments, at least one scFv is fused to an Fc. In some embodiments, the Fc comprises a wildtype human IgG4 isotype, or derivative thereof. In some embodiments, GAA is conjugated to the carboxy terminus of the Fc. In some embodiments, the multidomain therapeutic protein comprises an anti-hTfR scFv and an anti hCD63 scFv. In some embodiments, the anti hTfR scFv and anti hCD63 scFv are both linked, at their carboxy termini, to a single GAA enzyme. In some embodiments, the delivery domain is an anti-hTfR scFv, and the enzyme domain is linked to carboxy terminus of the VL domain of the scFv. In some embodiments, the multidomain further comprises a second delivery domain linked to the N-terminus of the VH domain of the anti-hTfR scFv. In some embodiments, the second delivery domain is an anti-hCD63 scFV. In some embodiments, the enzyme domain comprises the amino acid sequence set forth as SEQ ID NO:1

Also provided are multidomain therapeutic proteins comprising at least two delivery domains and at least one enzyme domain, wherein each of the two delivery domains is independently selected from the group consisting of an antibody, a half-body, and an scFv, and wherein at least one or more of the delivery domains is associated the at least one enzyme domain, preferably wherein the one or more delivery domains is covalently linked to the at least one enzyme domain. In some embodiments, the multidomain therapeutic protein comprises no more than two delivery domains. In some embodiments, only one of the delivery domains is associated with the at least one enzyme domain. In some embodiments, each of the at least two delivery domains is covalently linked to an enzyme domain. In some embodiments, each of the at least two delivery domains is covalently linked to the same enzyme domain. In some embodiments, each of the at least two delivery domains is covalently linked to a different enzyme domain. In some embodiments, the multidomain therapeutic protein comprises no more than two delivery domains, wherein the first delivery domain comprises a half-body, and wherein the second delivery domain comprises an scFv. In some embodiments, the scFv is fused to an Fc. In some embodiments, the half-body is covalently linked at its carboxy terminus to a first enzyme domain and/or wherein the scFv is covalently linked at its carboxy terminus to an Fc, and optionally, a second enzyme domain. In some embodiments, the multidomain therapeutic protein comprises no more than two delivery domains, wherein the first and second delivery domains each comprise an scFv. In some embodiments, both the first and second scFv are covalently linked to an enzyme domain. In some embodiments, the multidomain therapeutic protein comprises from N-terminus to C-terminus: the first scFv, the second scFv, and the enzyme domain. In some embodiments, at least one delivery domain binds a lysosomal trafficking molecule and at least one delivery domain binds a transcytosis effector. In some embodiments, the lysosomal trafficking molecule is selected from the group consisting of CD63, ITGA7, CD9, CD63, CD81, CD82, or CD151, and wherein the transcytosis effector is selected from the group consisting of an LDL receptor, an IgA receptor, a transferrin receptor, a neonatal Fc receptor, insulin receptor, CD98, and Basigin. In some embodiments, the multidomain therapeutic protein comprises a structure as depicted in FIG. 1C, FIG. 1D, FIG. 1E, or FIG. 1F.

Also provided herein are polynucleotides that encode the multidomain therapeutic proteins described herein. In some embodiments, a polynucleotide provided herein further comprising a virus nucleic acid sequence and a locus-targeting nucleic acid sequence. In some embodiments, the polynucleotide further comprises a virus nucleic acid sequence and a locus-targeting nucleic acid sequence, wherein the virus nucleic acid sequence is an adeno-associated virus (AAV) nucleic acid sequence. In some embodiments, the polynucleotide further comprises a virus nucleic acid sequence and a locus-targeting nucleic acid sequence, wherein the virus nucleic acid sequence is an adeno-associated virus (AAV) nucleic acid sequence, and wherein the AAV nucleic acid sequence comprises an internal terminal repeat sequence, and optionally, a tissue specific regulatory element such as a liver specific promoter or a neuronal specific promoter. In some embodiments, the polynucleotide further comprises a virus nucleic acid sequence and a locus-targeting nucleic acid sequence, wherein the virus nucleic acid sequence is an adeno-associated virus (AAV) nucleic acid sequence comprising an internal terminal repeat sequence that comprises SEQ ID NO:6, SEQ ID NO:7, or both, and optionally, a tissue specific regulatory element such as a liver specific promoter or a neuronal specific promoter. In some embodiments, the polynucleotide further comprises a tissue specific regulatory element comprising the sequence set forth as SEQ ID NO:8 and/or SEQ ID NO:9.

In one aspect, the invention provides a gene therapy vector, such as an AAV vector, that contains a nucleic acid sequence encoding a therapeutic protein conjugated to or fused to a CSR-BP, e.g., a polynucleotide as described herein. In some embodiments, the gene therapy vector is selected from the group consisting of a viral vector, optionally wherein the viral vector is a natural virus, an engineered virus, or a chimeric virus, and a naked polynucleotide comprising a polynucleotide described herein, a polynucleotide complex, optionally wherein the polynucleotide complex is a lipid nanoparticle comprising the polynucleotide and lipids, and any combination thereof. In some embodiments, the gene therapy vector is a viral vector selected from the group consisting of a retrovirus, adenovirus, herpes simplex virus, pox virus, vaccinia virus, lentivirus, or an adeno-associated virus. In some embodiments, the gene therapy vector is AAV9, Anc80, an AAV2/8 chimera and/or an AAV pseudotyped to a specific tissue, e.g., the liver or neuronal tissue.

In one embodiment, a therapeutic protein, nucleotide encoding same, and/or gene therapy vectors comprising the nucleotide encoding same is used to treat a subject in need of enzyme replacement therapy, e.g., in a method of delivering a therapeutic protein to the central nervous system (CNS) of a subject, comprising administering to the subject a nucleotide composition encoding a multidomain therapeutic protein via a liver-targeted delivery method sufficient to provide a therapeutically effective amount of the multidomain therapeutic protein in the CNS, wherein the multidomain therapeutic protein comprises a delivery domain and an enzyme domain. In some embodiments, the subject is an animal. In some embodiments, the subject is a human.

In one aspect, an AAV vector containing a polynucleotide encoding an scFv-hydrolase fusion protein is administered to a human or non-human subject. The polynucleotide subsequently integrates at a genomic locus in the liver and the encoded fusion protein is produced. In another embodiment, the polynucleotide is transcribed episomally in the liver and the encoded fusion protein is produced. In a specific embodiment, the fusion protein is an anti-CD63scFv-GAA fusion protein or an anti-ITGA7scFv-GAA fusion protein, the human or non-human subject lacks endogenous GAA activity, and the GAA activity is effectively restored in the subject.

In one aspect, the invention provides a method of treating a subject (human or non-human) with an enzyme deficiency by administering to the patient a gene therapy vector containing a gene encoding a therapeutic protein conjugated to or fused to a CSR-BP.

Described herein are methods of delivering a therapeutic protein to the central nervous system (CNS) of a subject, comprising administering to the subject a nucleotide composition encoding a multidomain therapeutic protein via a liver-targeted delivery method sufficient to provide a therapeutically effective amount of the multidomain therapeutic protein in the CNS, wherein the multidomain therapeutic protein comprises a delivery domain and an enzyme domain. In some embodiments, the delivery domain is an antibody or antigen-binding fragment thereof that binds specifically to an internalizing effector. In some embodiments, the therapeutic protein is a lysosomal enzyme. In some embodiments, the lysosomal enzyme is GAA. In some embodiments, the nucleotide composition is administered via a viral vector. In some embodiments, the viral vector is an AAV vector. In some embodiments, the nucleotide composition is administered at a dose of at least 2×1012 viral genomes per kilogram (vg/kg). In some embodiments, the internalizing effector is expressed on the surface of cells selected from the group consisting of: cells in the CNS, epithelial cells, and cells that cross the blood brain barrier. In some embodiments, the delivery domain binds an internalizing effector. In some embodiments, the internalizing effector is (i) selected from the group consisting of CD63, Integrin alpha-7 (ITGA7), MHC-I, Kremen-1, Kremen-2, LRP5, LRP6, LRP8, transferrin receptor, LDL-receptor, LDL-related protein 1 receptor, ASGR1, ASGR2, amyloid precursor protein-like protein-2 (APLP2), apelin receptor (APLNR), myelin and lymphocyte protein (MAL), IGF2R, vacuolar-type H+ ATPase, diphtheria toxin receptor, folate receptor, glutamate receptors, glutathione receptor, leptin receptors, scavenger receptor A1-5 (SCARA1-5), SCARB1-3, and CD36; (ii) expressed in several tissue types, e.g., CD63, MHC-I, vacuolar-type H+ ATPase, IGF2R, Integrin alpha-7 (ITGA7), LRP5, LRP6, LRP8, Kremen-2, LDL-receptor, LDL-related protein 1 receptor, amyloid precursor protein-like protein-2 (APLP2), apelin receptor (APLNR), PRLR, MAL (myelin and lymphocyte protein (MAL), diphtheria toxin receptors, HBEGF (heparin binding EGF like growth factor), glutathione receptors, glutamate receptors, leptin receptors, and folate receptors, optionally wherein the subject exhibits one or more symptoms of a disease selected from the group consisting of Fabry disease, Gaucher disease, MPS I, MPS II, MPS IIIA, MPS IIIB, MPS IIID, MPS IVB, MPS VI, MPS VII, MPS IX, Pompe disease, Lysosomal acid lipase deficiency, Metachromatic leukodystrophy, Niemann-Pick diseases types A, B, and C2, Alpha mannosidosis, Neuraminidase deficiency, Sialidosis, Aspartylglycosaminuria, Combined saposin deficiency, Atypical Gaucher disease, Farber lipogranulomatosis, Fucosidosis, and Beta mannosidosis; (iii) preferentially expressed by bone and/or cartilage, e.g., Collagen X, Integrin alpha 10 (ITGA10), Fibroblast growth factor receptor 3 (FGFR3), Fibroblast growth factor receptor isoform C (FGFR3C), Hyaluronan and proteoglycan link protein 1 (CRTL1), Aggrecan, Collagen II, and Kremen-1, optionally wherein the subject exhibits one or more symptoms of a disease selected from the group consisting of MPS I, MPS II, MPS IIIA, MPS IIIB, MPS IIID, MPS IVA, MPS IVB, MPS VI, MPS VII, MPS IX, Beta mannosidosis, Gaucher disease, atypical Gaucher disease, combined Saposin deficiency, Aspartylglycosaminuria, Farber lipogranulomatosis, Sialidosis, Neuraminidase deficiency, and Alpha mannosidosis; (iv) preferentially expressed by monocytes, macrophages, or microglia, e.g., scavenger receptor A1-5 (SCARA1-5), SCARB1-3, CD36, MSR1 (macrophage scavenger receptor 1), MRC1 (macrophage mannose receptor 1), VSIG4 (V-set and immunoglobulin domain-containing protein 4), CD68 (Macrosialin), and CSF1R (Macrophage colony-stimulating factor 1 receptor), optionally wherein the subject exhibits one or more symptoms of a disease selected from the group consisting of lysosomal acid lipase deficiency, Gaucher disease, Atypical Gaucher disease, combined Saposin deficiency, and Farber lipogranulomatosis; (v) preferentially expressed by kidney cells, e.g., CDH16 (Cadheri-16), CLDN16 (Claudn-16), KL (Klotho), PTH1R (parathyroid hormone receptor), SLC22A13 (Solute carrier family 22 member 13), SLC5A2 (Sodium/glucose cotransporter 2), and UMOD (Uromodulin), optionally wherein the subject exhibits one or more symptoms or is diagnosed with a disease selected from the group consisting of Fabry disease, Alport syndrome, polycystic kidney disease, and Thrombotic Thrombocytopenic Purpura; (vi) preferentially expressed by liver cells, e.g., ASGR1 or ASGR2, optionally wherein the subject exhibits one or more symptoms or is diagnosed with a disease selected from the group consisting of as lysosomal acid lipase deficiency, Gaucher disease, MPS VI, MPS VII, MPS II, Niemann-Pick diseases types A, B, and C2, Sialidosis, Neuraminidase deficiency, atypical Gaucher disease, combined Saposin deficiency, Farber lipogranulomatosis; (vii) preferentially expressed by muscle cells, e.g., BMPR1A (Bone morphogenetic protein receptor 1A), m-cadherin, CD9, MuSK (muscle-specific kinase), LGR4/GPR48 (G protein-coupled receptor 48), cholinergic receptor (nicotinic) alpha 1, CDH15 (Cadheri-15), ITGA7 (Integrin alpha-7), CACNG1 (L-type calcium channel subunit gamma-1), CACNA1S (L-type calcium channel subunit alpha-15), CACNG6 (L-type calcium channel subunit gamma-6), SCN1B (Sodium channel subunit beta-1), CHRNA1 (ACh receptor subunit alpha), CHRND (ACh receptor subunit delta), LRRC14B (Leucine-rich repeat-containing protein 14B), dystroglycan (DAG1), and POPDC3 (Popeye domain-containing protein 3), optionally wherein the subject exhibits one or more symptoms or is diagnosed with Pompe disease; (viii) selected from the group consisting of ITGA7, CD9, CD63, ALPL2, MSR1, ASGR1, ASGR2, or PRLR; and/or (ix) is CD63. In some embodiments, the delivery domain is a single-chain variable fragment (scFv). In some embodiments, the cell surface receptor (CSR)-binding protein (CSR-BP) comprises an amino acid sequence of SEQ ID NO:2. In some embodiments, the therapeutic protein comprises a hydrolase. In some embodiments, the therapeutic protein comprises a glycosylase. In some embodiments, the therapeutic protein comprises a glycosidase. In some embodiments, the therapeutic protein comprises an alpha-glucosidase. In some embodiments, the therapeutic protein comprises an amino acid sequence of SEQ ID NO:1 or SEQ ID NO:13, or a fragment thereof. In some embodiments, the therapeutic protein comprises an anti-ABeta, or an anti-Tau antibody. In some embodiments, the polynucleotide comprises a nucleic acid sequence of SEQ ID NO:11. In some embodiments, the enzyme domain comprises an alpha-glucosidase, and wherein the glycogen levels in any CNS tissue in the subject is reduced for at least nine months post-treatment. In some embodiments, the subject has Pompe disease. In some embodiments, the administered nucleotide composition provides a multidomain therapeutic protein serum level of at least 1 µg/mL. In some embodiments, the therapeutic protein comprises a glycosidase, such as GAA (e.g., SEQ ID NO:1) or GLA (e.g., UniProtKB No. P06280, aa32-429, SEQ ID NO:13), and the patient has Pompe disease or Fabry disease. In some embodiments, the CSR-BP is an antigen-binding protein that binds to an internalization receptor, such as CD63 or ITGA7. In some embodiments, the CSR-BP is an scFv molecule that binds CD63. In some embodiments, the CSR-BP is an scFv molecule that binds ITGA7. In some embodiments, the gene therapy vector is an AAV vector comprising a polynucleotide that encodes an anti-CD63-GAA fusion therapeutic protein. In some embodiments, the gene therapy vector is an AAV vector comprising a polynucleotide that encodes an anti-ITGA7-GAA fusion therapeutic protein.

In one embodiment, the therapeutic protein comprises a GAA enzyme domain, and high serum levels of GAA are maintained in the serum of the patient for at least 12 weeks after administering the gene therapy vector. In some embodiments, the therapeutic protein comprises a GAA enzyme, and glycogen levels in CNS tissue in the patient are significantly reduced. In some embodiments, the therapeutic protein comprises a GAA enzyme, and glycogen levels are maintained at wildtype levels 3 months, 6 months, or 9 months after administration of the gene therapy vector. In some embodiments, the therapeutic protein comprises a GAA enzyme, and the muscle strength of the patient after treatment is restored to wildtype levels.

In one aspect, the invention provides a method of reducing glycogen accumulation in a tissue, particularly a CNS tissue, in a human or non-human subject by administering a gene therapy vector containing a polynucleotide that encodes a therapeutic protein fused to a CSR-BP. In some embodiments, the gene therapy vector is administered at a dose sufficient to provide a threshold serum level of the therapeutic protein fused to a CSR-BP. In some embodiments, the threshold level is at least 1 µg/mL. In some embodiments, the threshold level is at least 2 µg/mL. In some embodiments, the threshold level is at least 3 µg/mL. In some embodiments, the threshold level is at least 4 µg/mL. In some embodiments, the threshold level is at least 5 µg/mL. In some embodiments, the threshold level is at least 6 µg/mL. In some embodiments, the threshold level is at least 7 µg/mL. In some embodiments, the threshold level is at least 8 µg/mL. In some embodiments, the threshold level is at least 9 µg/mL. In some embodiments, the threshold level is at least 10 µg/mL. In some embodiments, the threshold level is at least 11 µg/mL. In some embodiments, the threshold level is at least 12 µg/mL. In some embodiments, the threshold level is at least 13 µg/mL. In some embodiments, the threshold level is at least 14 µg/mL. In some embodiments, the threshold level is at least 15 µg/mL. In one embodiment, the tissue is cerebellum, spinal cord or hippocampus. In one embodiment, the human or non-human subject has Pompe disease. In one embodiment, the therapeutic protein comprises an anti-CD63 scFv-GAA fusion protein. In another embodiment, the therapeutic protein comprises an anti-ITGA7 scFv-GAA fusion protein.

DRAWINGS

FIG. 1A schematically represents multidomain therapeutic proteins. Panel A depicts a multidomain therapeutic protein comprising a bispecific antibody (ii) and a replacement enzyme (i). Panel B depicts an enzyme-Fc fusion polypeptide (i) associating with an internalizing effector-specific half-body (ii) to form the multidomain therapeutic protein. Panel C depicts a replacement enzyme (hexagon) covalently linked to the C-terminus of the heavy chain of an anti-internalizing effector antibody. Panel D depicts a replacement enzyme (hexagon) covalently linked to the N-terminus of the heavy chain of an anti-internalizing effector antibody. Panel E depicts a replacement enzyme (hexagon) covalently linked to the C-terminus of the light chain of an anti-internalizing effector antibody. Panel F depicts a replacement enzyme (hexagon) covalently linked to the N-terminus of the light chain of an anti-internalizing effector antibody. Panel G depicts a replacement enzyme (hexagon) covalently linked to the C-terminus of a single-chain variable fragment (scFv) containing a VH region (shaded bar) and a VL region (open bar). Panel H depicts a replacement enzyme (hexagon) covalently linked to two scFv domains, the first scFv (i) which serves as a first delivery domain, and the second scFv (ii) which serves as a second delivery domain. Additional multidomain therapeutic proteins not depicted in FIG. 1A include, but are not limited to, multidomain therapeutic proteins comprising two or more delivery domains and at least one enzyme domain. As non-limiting examples, the antibodies, half-bodies and scFv domains depicted in panels A-H of this figure may represent any type of delivery domain, and additional delivery domains or replacement enzymes can be also associated to make a multidomain therapeutic protein. Non-limiting examples of multidomain therapeutic proteins comprising two or more delivery domains are further depicted in FIGS. 1C, 1D, and 1F, which include a replacement enzyme (depicted as, but not limited to, GAA) covalently linked to a first internalizing effector-specific half-body, which associates with a second internalizing effector-specific scFv-Fc fusion, which may or may not also be covalently linked to a replacement enzyme (depicted as, but not limited to, GAA), to form the multidomain therapeutic protein (FIGS. 1C and 1D), a replacement enzyme (depicted as, but not limited to, GAA) covalently linked to the C-terminus of each of an anti-internalizing effector-specific half-body, which serves as a first delivery domain, and an internalizing effector-specific scFv-Fc fusion, which serves as a second delivery domain, where both the anti-internalizing effector-specific half-body and associate together to form the multidomain therapeutic protein (FIG. 1D), and a replacement enzyme covalently linked to a first scFv, which is linked, e.g., via a linker, to a second scFv (FIG. 1F).

Figure 1B:
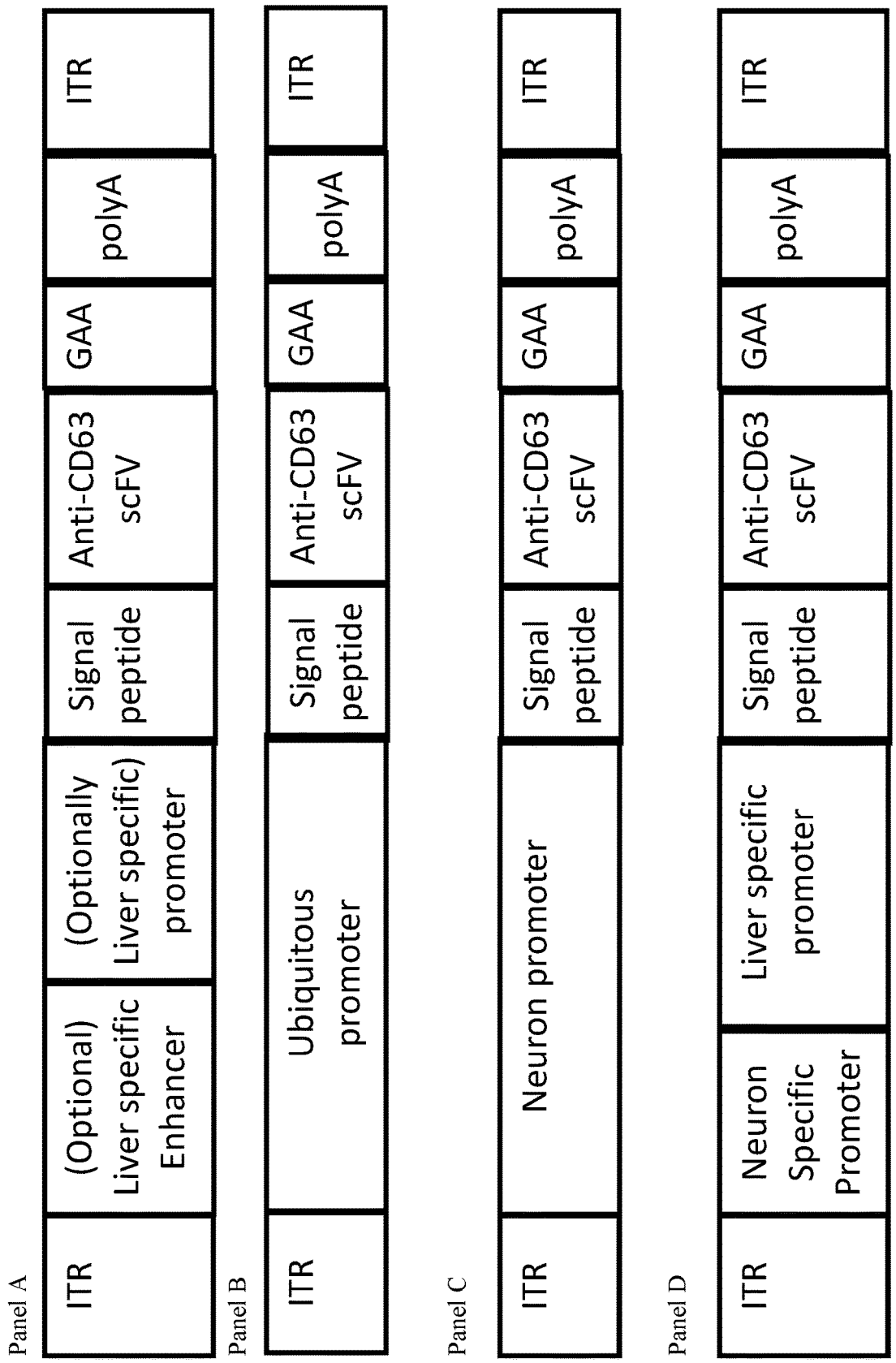

FIG. 1B provides non-limiting exemplary illustrations of AAV gene therapy vectors that each encode a multidomain therapeutic protein represented in panel G of FIG. 1A, wherein the scFv is an anti-human CD63 scFv and the replacement enzyme is GAA (e.g., anti-hCD63scFv::hGAA; see, e.g., the amino acid sequence set forth as SEQ ID NO:10). Amino acids 1-117 of SEQ ID NO:10 provide the amino acid sequence of the heavy chain variable domain (VH) of the H4H12450N antibody; amino acids 118-132 of SEQ ID NO:10 provide an amino acid linker sequence between the heavy and light chain variable domains of H4H12450N; amino acids 133-240 of SEQ ID NO:364 provide the amino acid sequence of the light chain variable domain ($V_L$) of the H4H12450N antibody; amino acids 241-245 of SEQ ID NO:10 provides an amino acid linker sequence between the anti-hCD63scFv and GAA; and amino acids 246-1128 of SEQ ID NO:10 provides the amino acid sequence of the replacement enzyme GAA, or biologically active portion thereof. Exemplary 5' ITR and 3' ITR sequences are respectively set forth as SEQ ID NO:6 and SEQ ID NO:7. Panel A of this Figure provides an exemplary vector for liver specific expression comprising an exemplary liver specific enhancer (e.g., but not limited to, Serpinal; set forth as SEQ ID NO:9), an exemplary liver specific promoter (e.g., but not limited to, TTR; set forth as SEQ ID NO:8), an exemplary signal peptide; a nucleic acid sequence encoding the anti-hCD63scFv::hGAA multitherapeutic domain (SEQ ID NO:10), and a poly-A tail. Panel B of this figure provides an exemplary vector similar to that shown in Panel A with an exemplary ubiquitous promoter in place of the liver specific enhancer and liver specific promoter sequences. Panel C of this figure provides an exemplary vector similar to that shown in Panel A with an exemplary neuron specific promoter in place of the liver specific enhancer (e.g., SerpinA1) and promoter (e.g., TTR). Panel D of this figure provides an exemplary vector similar to that shown in Panel A with an exemplary neuron specific promoter in combination with a liver specific (e.g., SerpinA1) enhancer and promoter (e.g., TTR).

FIG. 1C provides non-limiting exemplary illustrations of expression vectors that each encode a multidomain therapeutic protein as depicted, wherein the half-body is an anti-CD63 antibody, the scFv is an anti-human transferrin receptor scFv, and wherein the replacement enzyme is GAA (e.g., anti-hTfRscFv::hGAA).

Figure 1D:
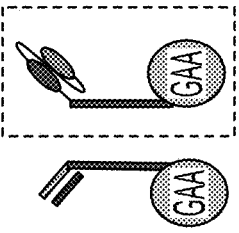

FIG. 1D provides non-limiting exemplary illustrations of expression vectors that each encode a multidomain therapeutic protein as depicted, wherein the half-body is an anti-CD63 antibody, wherein the scFv is an anti-human transferrin receptor (TfR) scFv and the Fc domain is a human IgG4 Fc, and wherein the replacement enzyme is GAA (e.g., anti-hTfRscFv::hGAA).

Figure 1E:

FIG. 1E provides non-limiting exemplary illustrations of expression vectors that each encode a multidomain therapeutic protein represented in Panel H of FIG. 1A, wherein one of the two scFv is an anti-human CD63 scFv, the other of the two scFv is an anti-human transferrin receptor (TfR) scFv, and the replacement enzyme is GAA (e.g., anti-hCD63 scFv::hGAA::anti-TfRscFV), FIG. 1F provides non-limiting exemplary illustrations of expression vectors that each encode a multidomain therapeutic protein as depicted, wherein one of the two scFv is an anti-human CD63 scFv, the other of the two scFv is an anti-human transferrin receptor (TfR) scFv, and the replacement enzyme is GAA (e.g., anti-hCD63scFv::anti-TfRscFV::GAA or anti-TfRscFV::anti-hCD63scFv::GAA).

FIG. 1G provides non-limiting exemplary illustrations of expression vectors that each encode a multidomain therapeutic protein as depicted in panel G of FIG. 1A, wherein the scFv is an anti-human transferrin receptor (TfR) scFv and the replacement enzyme is GAA (e.g., anti-TfRscFV::GAA).

Figure 2:
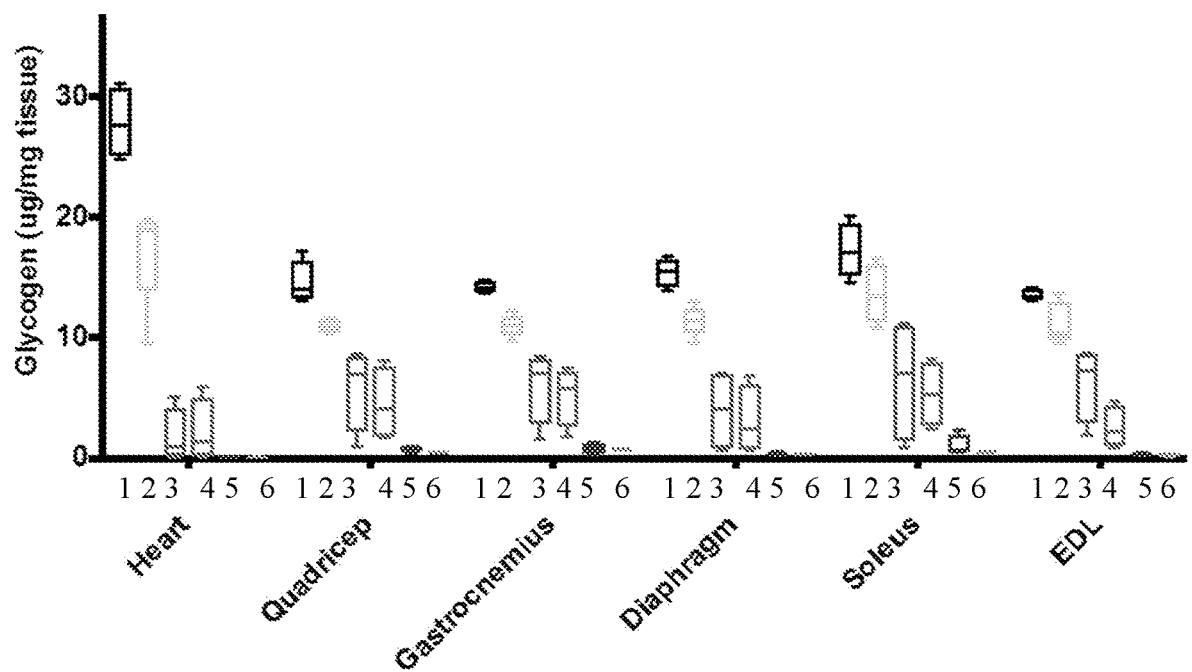

FIG. 2 is a bar graph depicting the amount of stored glycogen in micrograms per milligram of tissue as a function of delivered enzyme. The X-axis depicts tissues from a $CD63^{hu/hu}$; $GAA^{-/-}$ mouse from left to right: heart, quadriceps, gastrocnemius, diaphragm, soleus, and extensor digitorum longus (EDL) muscle. Lane 1 boxes depict the amount of stored glycogen in an untreated mouse Pompe disease model. Lane 6 boxes depict the amount of stored glycogen in an untreated wildtype mouse model. Lane 2 boxes depict the amount of stored glycogen in a mouse Pompe disease model treated with AAV-hGAA (adeno-associated virus vector containing gene encoding human GAA) at a dose of $10^{10}$ vg. Lane 3 boxes depict the amount of stored glycogen in a mouse Pompe disease model treated with AAV-hGAA at a dose of $10^{11}$ vg. Lane 4 boxes depict the amount of stored glycogen in a mouse Pompe disease model treated with AAV-anti-hCD63scFv::hGAA (adeno-associated virus vector containing gene encoding an anti-human CD63 scFv domain linked to human GAA) at a dose of $10^{10}$ vg. Lane 5 boxes depict the amount of stored glycogen in a mouse Pompe disease model treated with AAV-anti-hCD63scFv::hGAA at a dose of $10^{11}$ vg.

Figure 3:
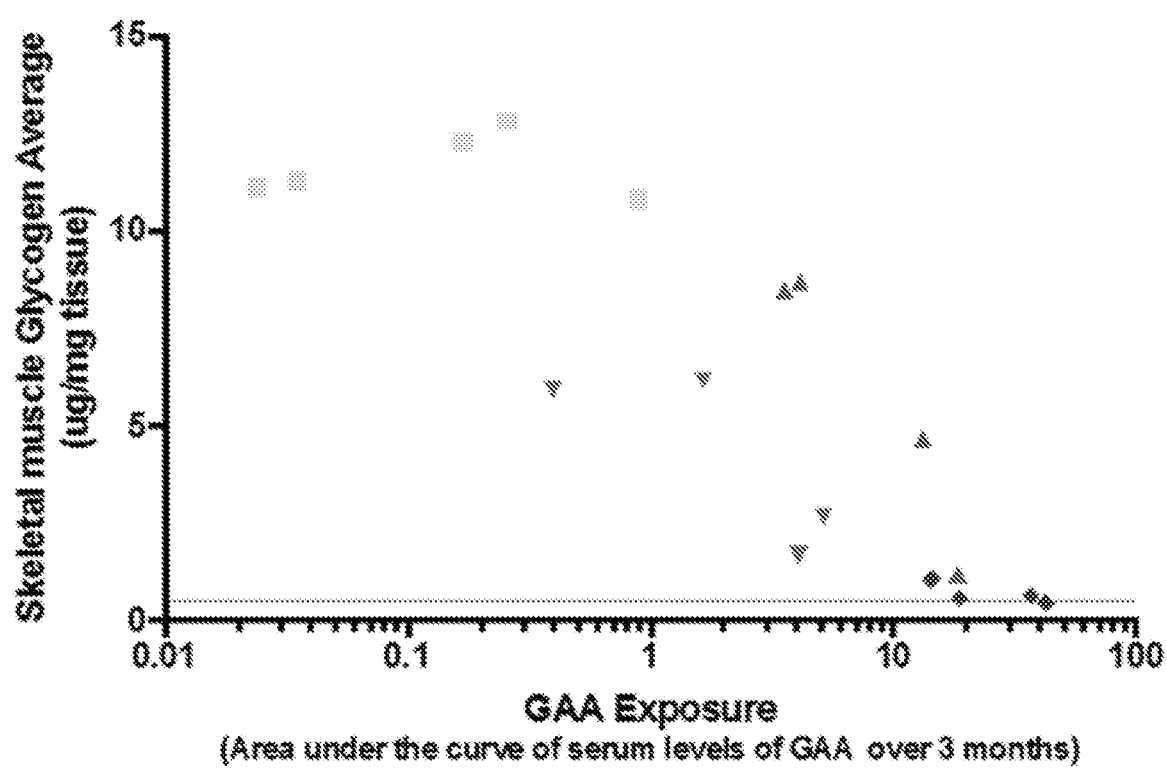

FIG. 3 is a graph depicting the average glycogen measured (μg/mg) in skeletal muscle tissue in each mouse at 3 months post-AAV injection. Each measurement is plotted as a function of GAA exposure (i.e., serum levels) per mouse treated with a particular enzyme construct at a particular dosage. Filled squares represent AAV-hGAA at a dose of $10^{10}$ vg. Filled pyramids represent AAV-hGAA at a dose of $10^{11}$ vg. Filled inverse pyramids represent AAV-anti-hCD63scFv::hGAA at a dose of $10^{10}$ vg. Filled diamonds represent AAV-anti-hCD63scFv::hGAA at a dose of $10^{11}$ vg.

Figure 4:
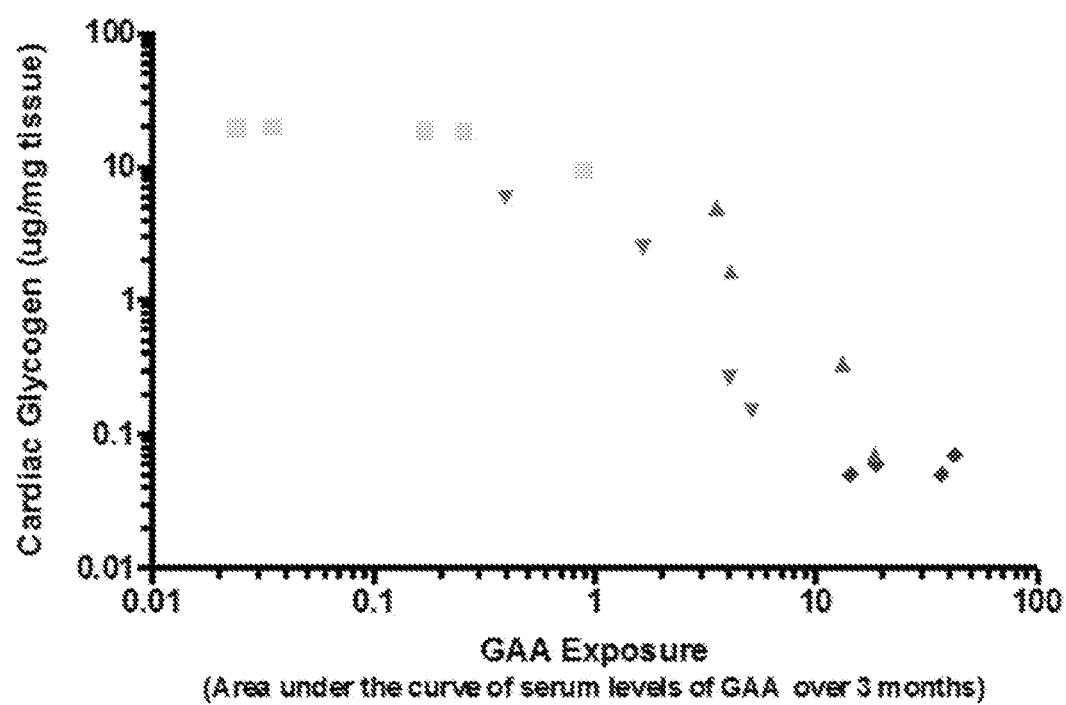

FIG. 4 is a dot plot depicting the average cardiac muscle glycogen measured (μg/mg) in heart tissue at 3 months post-AAV injection as a function of GAA exposure (i.e., serum levels), per mouse treated with a particular enzyme construct at a particular dosage. Filled squares represent AAV-hGAA at a dose of $10^{10}$ vg. Filled pyramids represent AAV-hGAA at a dose of $10^{11}$ vg. Filled inverse pyramids represent AAV-anti-hCD63scFv::hGAA at a dose of $10^{10}$ vg. Filled diamonds represent AAV-anti-hCD63scFv::hGAA at a dose of $10^{11}$ vg.

Figure 5:
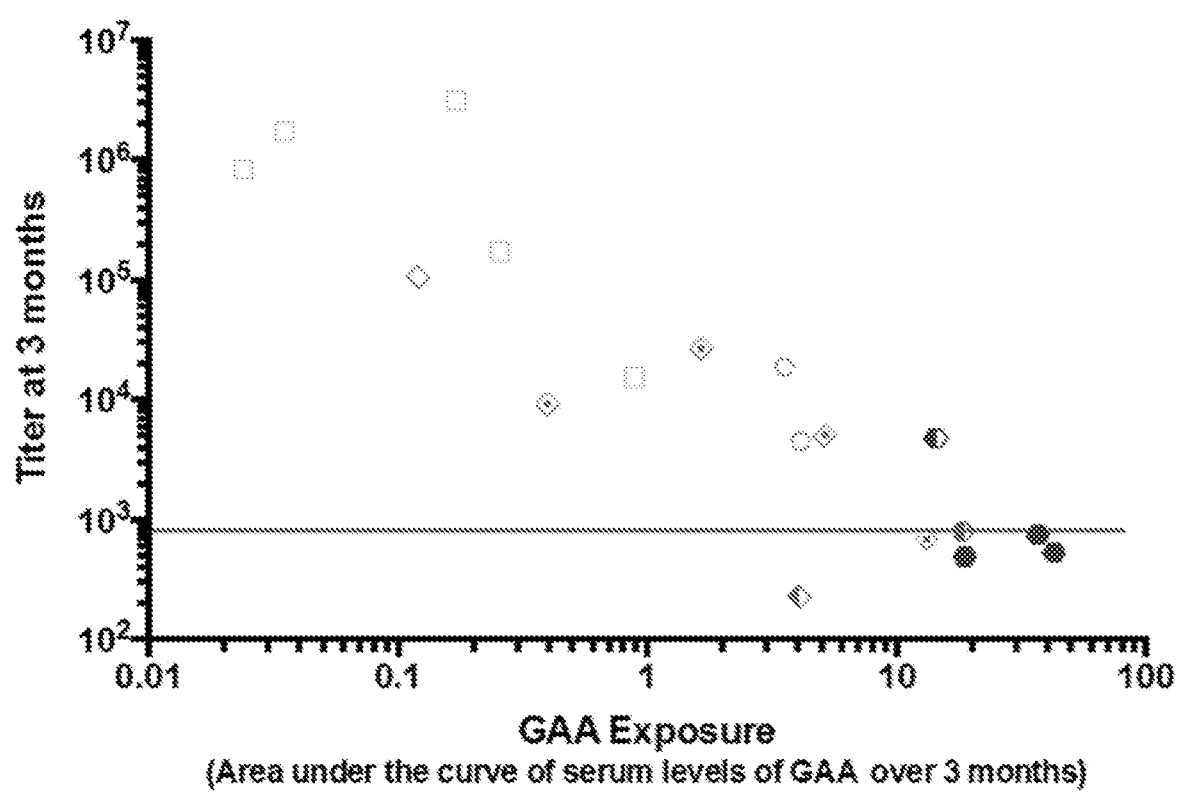

FIG. 5 is a dot plot depicting anti-GAA antibody titers at 3 months post-AAV injection as a function of GAA exposure (i.e. serum levels), per mouse treated with a particular enzyme construct at a particular dosage. Open squares represent AAV-hGAA at a dose of $10^{10}$ vg. Open circles represent AAV-hGAA at a dose of $10^{11}$ vg. Open diamonds represent AAV-anti-hCD63scFv::hGAA at a dose of $10^{10}$ vg. Hexagons represent AAV-anti-hCD63scFv::hGAA at a dose of $10^{11}$ vg.

Figure 6:
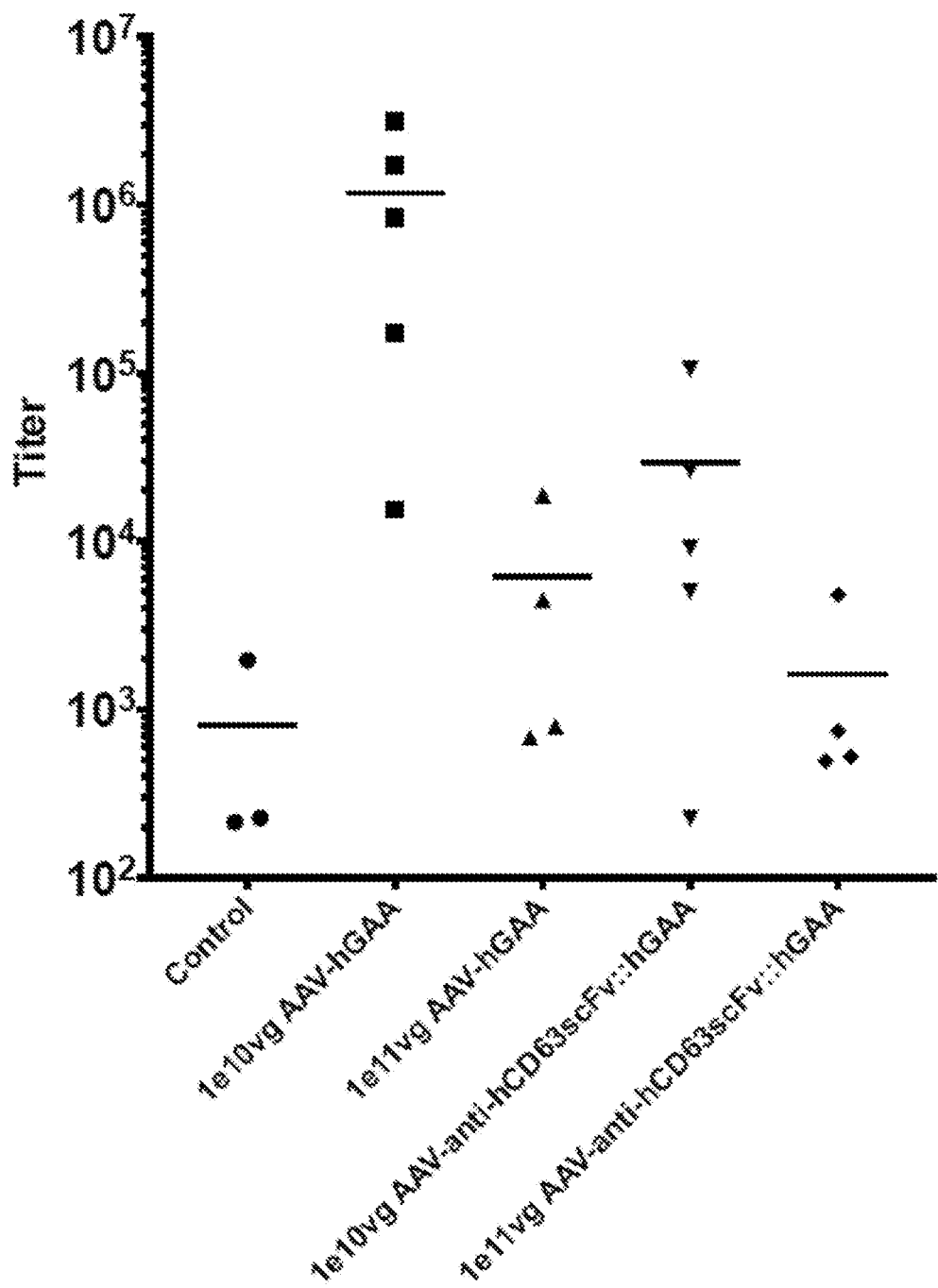

FIG. 6 is a dot plot depicting anti-GAA antibody titers at 3 months post-AAV injection as a function of enzyme construct and dose. Circles represent control mice receiving empty AAV vector. Squares represent AAV-hGAA at a dose of $10^{10}$ vg. Pyramids represent AAV-hGAA at a dose of $10^{11}$ vg. Inverse pyramids represent AAV-anti-hCD63scFv::hGAA at a dose of $10^{10}$ vg. Diamonds represent AAV-anti-hCD63scFv::hGAA at a dose of $10^{11}$ vg.

Figure 7A:
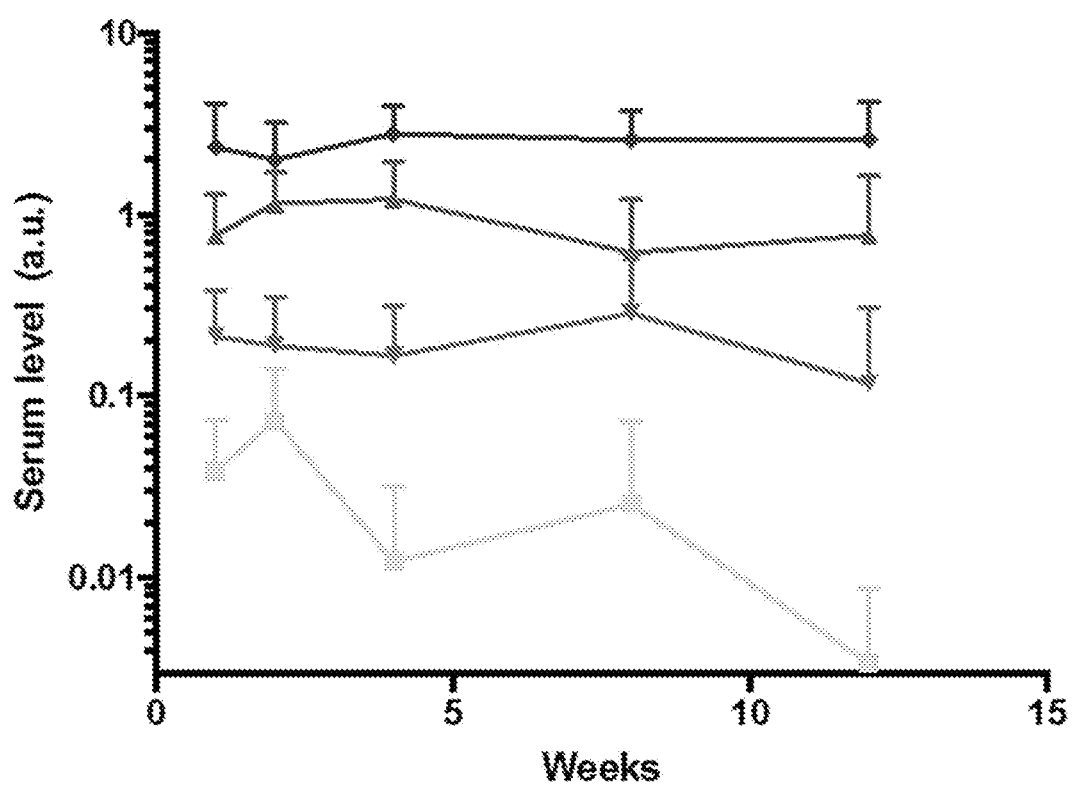

FIG. 7A is a line graph depicting serum levels of GAA (arbitrary units "au."; y-axis) as a function of time in weeks after gene therapy vector injection. Squares (bottom line) represent AAV-hGAA at a dose of $10^{10}$ vg. Pyramids (second from the top line) represent AAV-hGAA at a dose of $10^{11}$ vg. Inverse pyramids (third from the top line) represent AAV-anti-hCD63scFv::hGAA at a dose of $10^{10}$ vg. Diamonds (top line) represent AAV-anti-hCD63scFv::hGAA at a dose of $10^{11}$ vg.

Figure 7B:
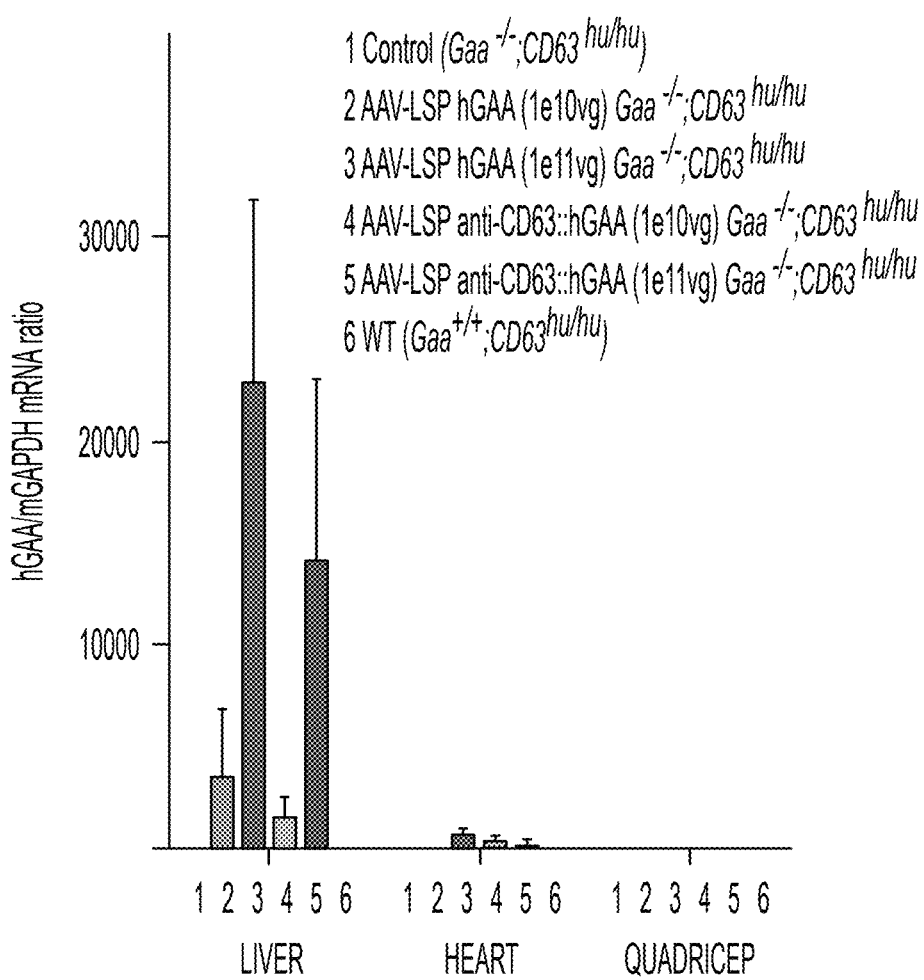

FIG. 7B is a bar graph depicting mRNA ratios (hGAA mRNA relative to mGADPH mRNA) following administration of AAV constructs in CD63 Humin GAA KO mice (GAA−/−,CD63hu/hu mice) or GAA+/+,CD63hu/hu mice, as such: (1) untreated control, (2) AAV-liver-specific promoter-hGAA (1e10 vg), (3) AAV-liver-specific promoter-hGAA (1e11 vg), (4) AAV-liver-specific promoter-anti-hCD63::hGAA (1e10 vg), (5) AAV-liver-specific promoter-anti-hCD63::hGAA (1e11 vg), or (6) untreated control (GAA+/+,CD63hu/hu). Liver expression of GAA was detected for all injections of AAV construct.

Figure 7C:
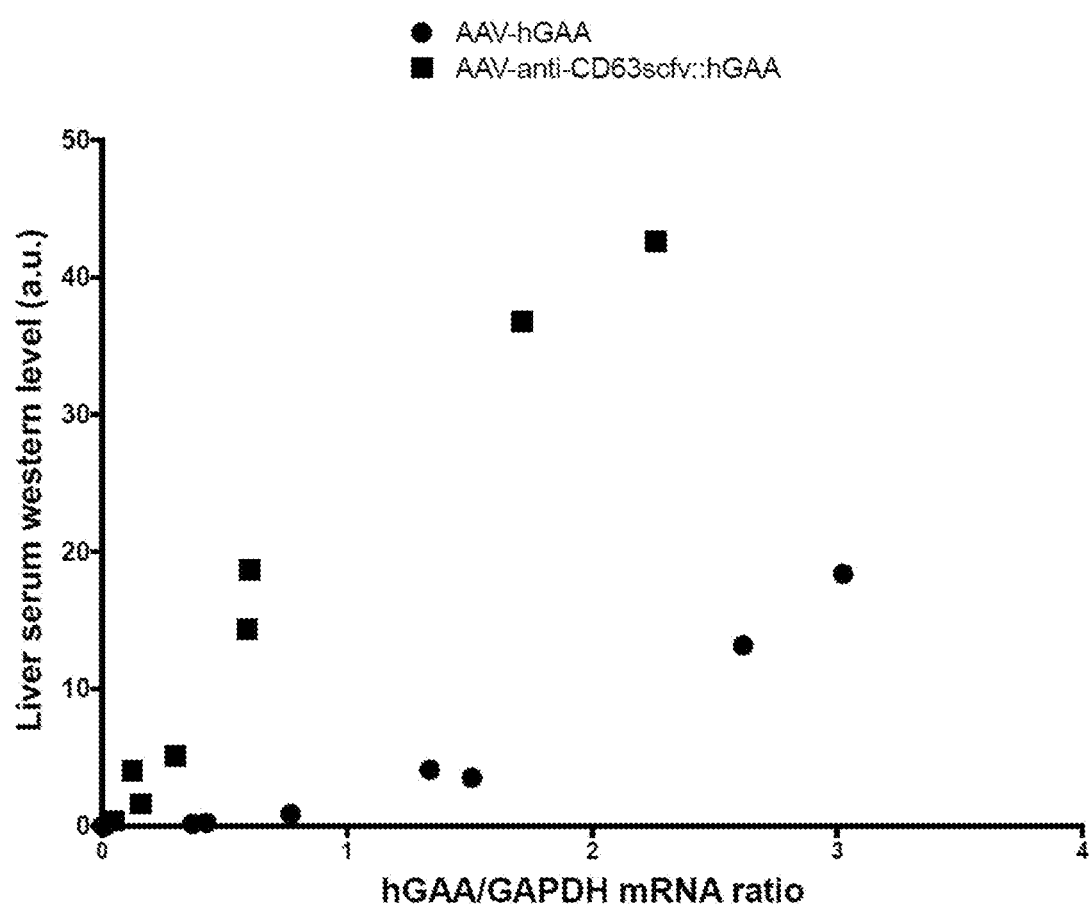

FIG. 7C is a plot graph comparing serum GAA level to RNA expression level of GAA for mice receiving the AAV encoding the fusion protein (squares) and mice receiving the AAV encoding GAA (both constructs provided a liver-specific promoter (LSP) to drive expression).

Figure 7D:
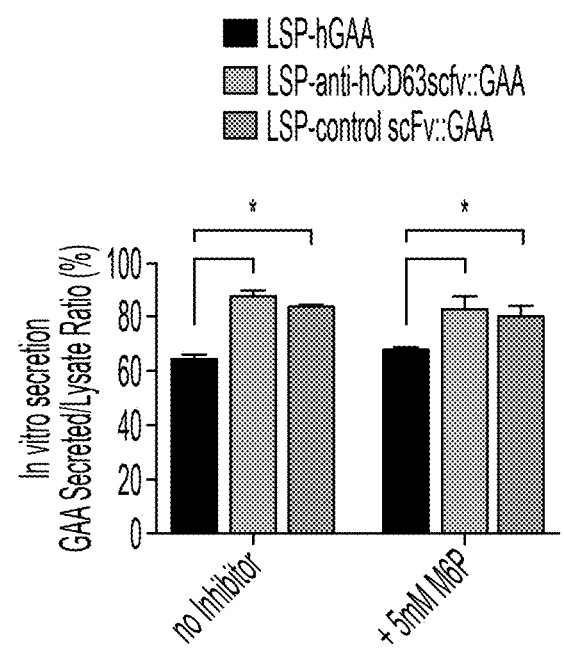

FIG. 7D is a bar graph showing Huh-7 human hepatocytes transiently transfected with liver-specific promoter driven constructs encoding for hGAA, anti-hCD63 scFv::GAA (fusion construct), or a non-binding fusion construct scFv::GAA control. Both scFv::GAA fusion constructs had a higher ratio of protein in the secreted supernatant than hGAA alone 3 days after transfection. Addition of M6P into the supernatant during the experimental period to mitigate CI-MPR-mediated uptake did not affect the ratio. (*=p<0.05, n=3).

Figure 7E:
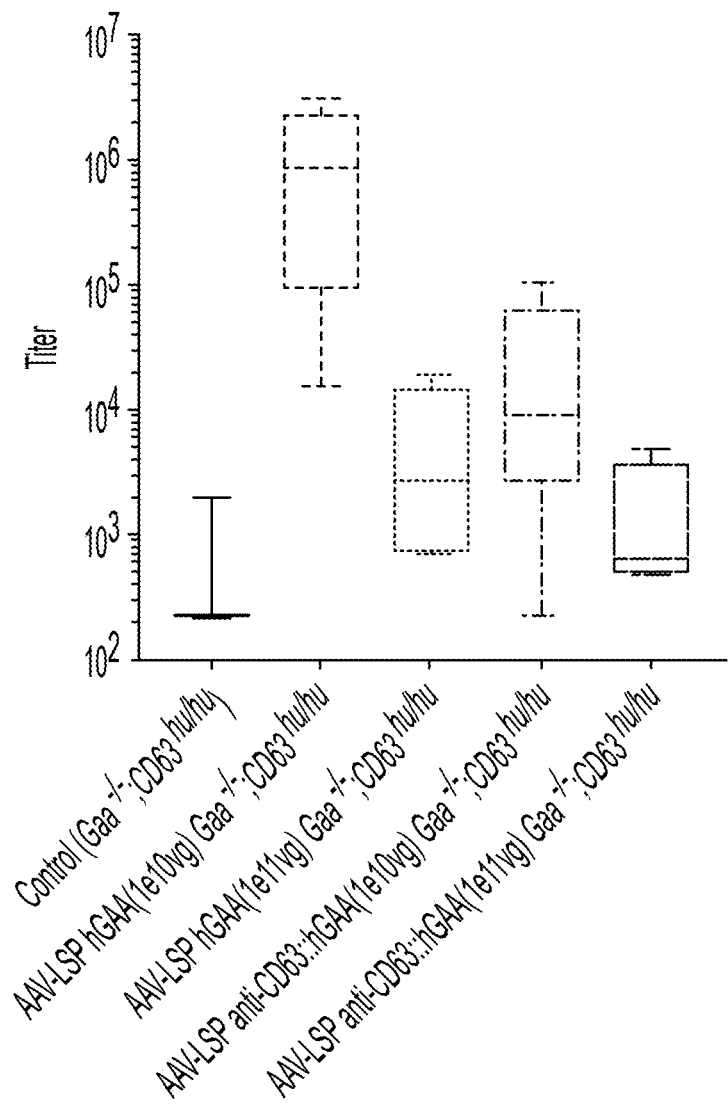

FIG. 7E is a bar graph depicting the amount of serum titer of GAA as a function of delivered vector. The X-axis depicts serum from KO mice humanized for CD63 (GAA−/−; CD63hu/hu) that were given plasmids encoding GAA or ScFv-GAA fusion from left to right: 1) Control (no treatment); 2) AAV-LSP-hGAA treatment (1e10 vg/mouse); 3) AAV-LSP-hGAA treatment (1e11 vg/mouse); 4) AAV-LSP-anti-CD63:: hGAA treatment (1e10 vg/mouse); and 5) AAV-LSP-anti-CD63:: hGAA treatment (1e11 vg/mouse).

Figure 8:
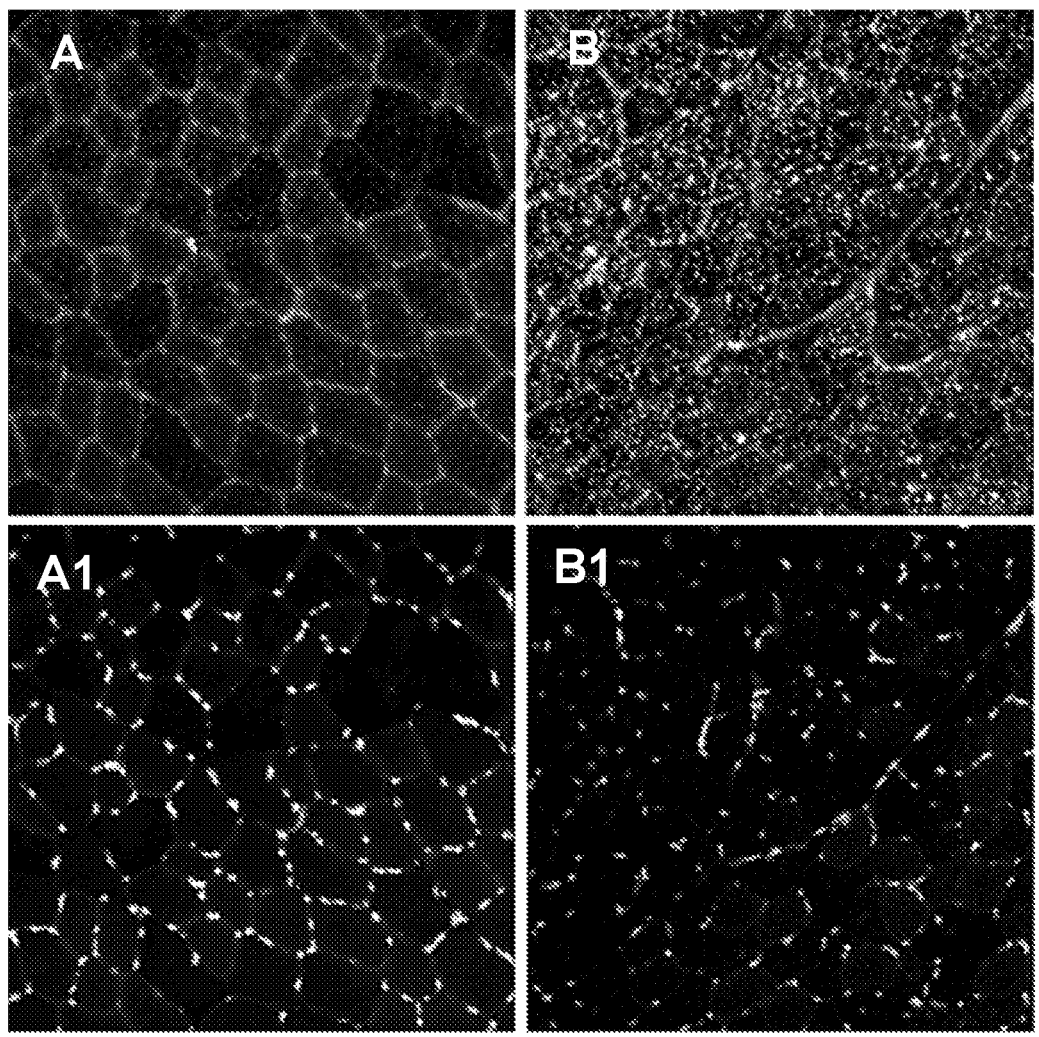
Figure 8:
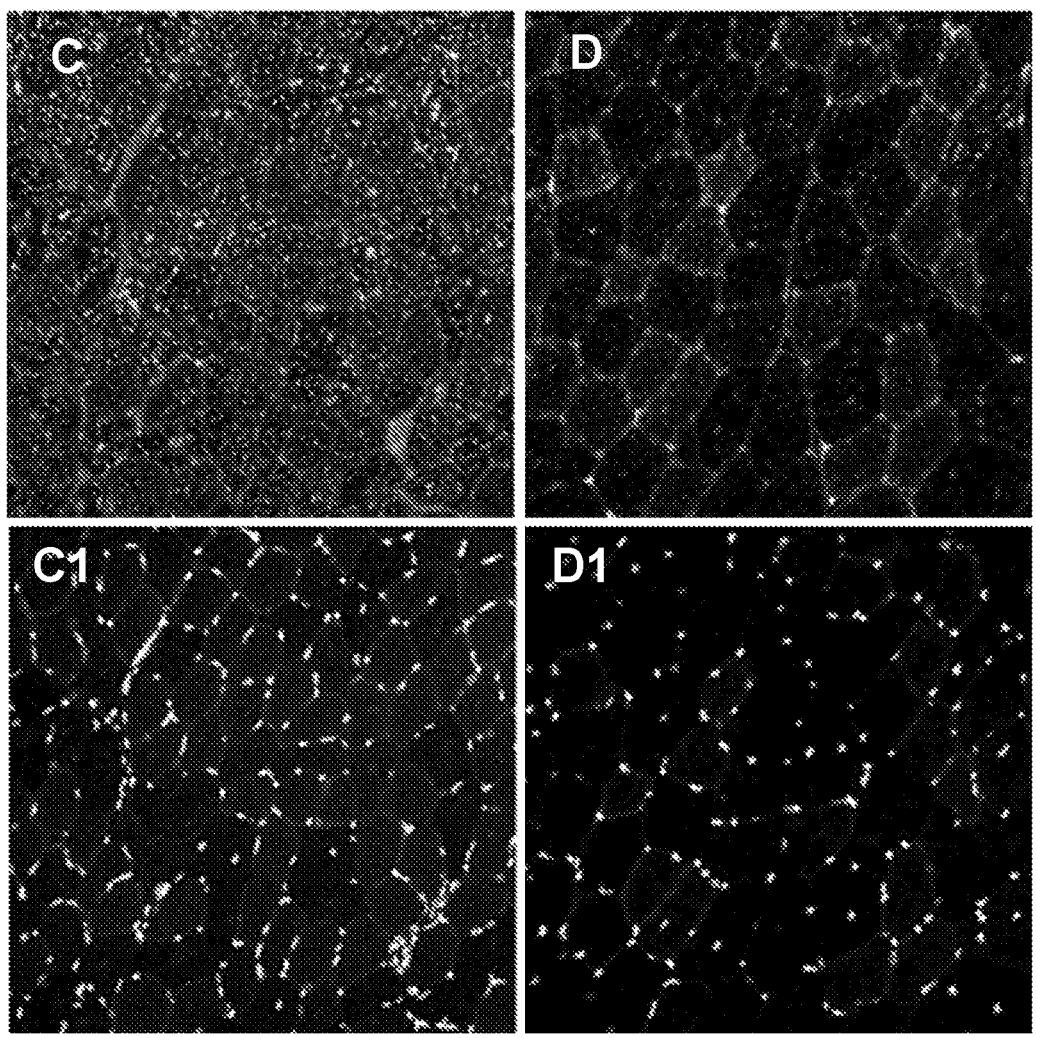

FIG. 8 are fluorescent micrographs depicting the lamp1-stained lysosomes in mouse muscle fibers counter-stained with DAPI to reveal nuclei. Panels A and A1 depict quadriceps cells derived from an untreated wildtype (GAA+/+) mouse and stained for lamp1 (panel A), and nuclei (panel A1). Panels B and B1 depict quadriceps cells derived from an untreated GAA null (GAA−/−) mouse and stained for lamp1 (panel B), and nuclei (panel B1). Panels C and C1 depict quadriceps cells derived from a GAA−/− mouse treated with an AAV-hGAA construct and stained for lamp1 (panel C), and nuclei (panel C1). Panels D and D1 depict quadriceps cells derived from a GAA−/− mouse treated with an AAV-hCD63scFv::hGAA construct and stained for lamp1 (panel D), and nuclei (panel D1).

Figure 9:
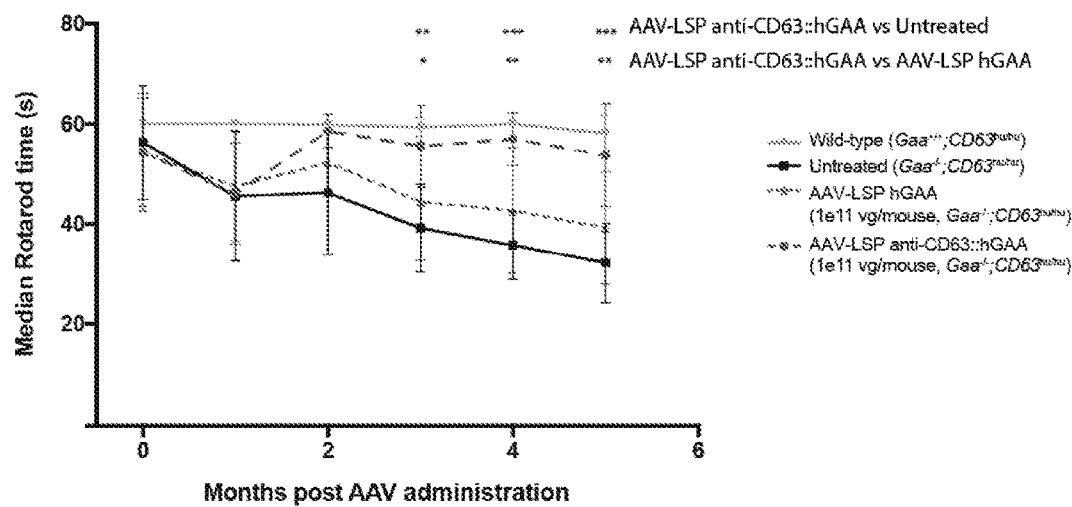
Figure 9:
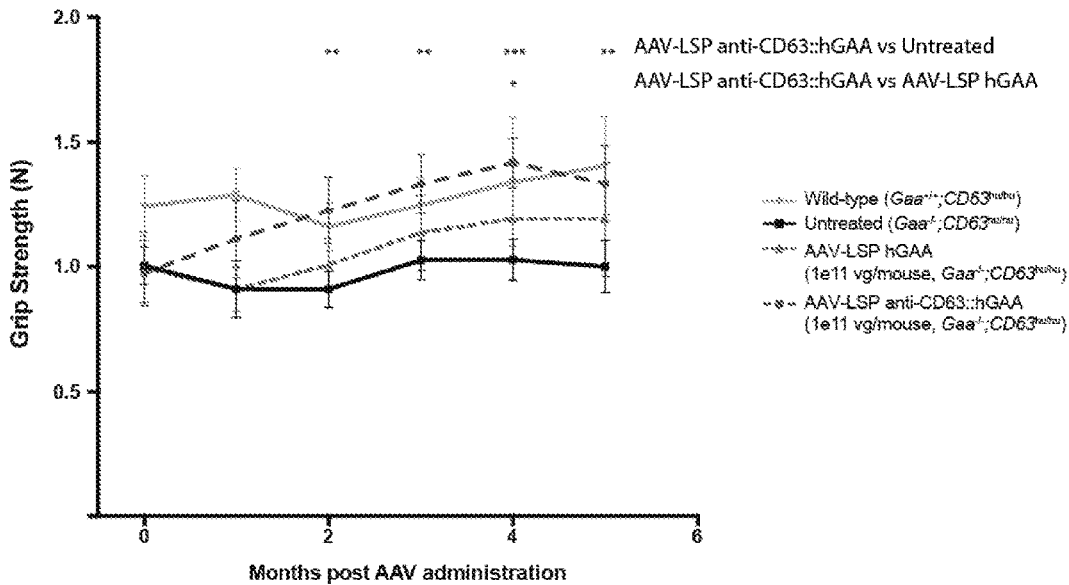

FIG. 9 depicts line graphs showing grip strength and Rotarod test performance of mice treated with either AAV-LSP hGAA or AAV-LSP anti-hCD63::hGAA. Accelerating Rotarod measurements (A) and forelimb grip strength measurements (B) of wild-type GAA mice (inverted triangle), untreated control (square), AAV-LSP-hGAA treatment (1e11 vg/mouse) (triangle) or AAV-LSP-anti-hCD63::hGAA treatment (1e11 vg/mouse) (circle) were taken at monthly intervals for 6 months. Error bars are +/−SD. N=8-10 for all groups.

Figure 10A:
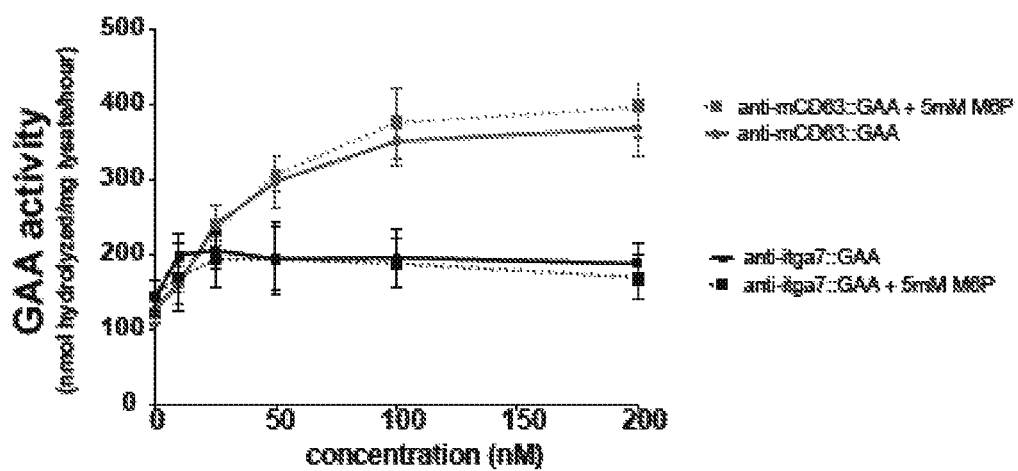
Figure 10B:
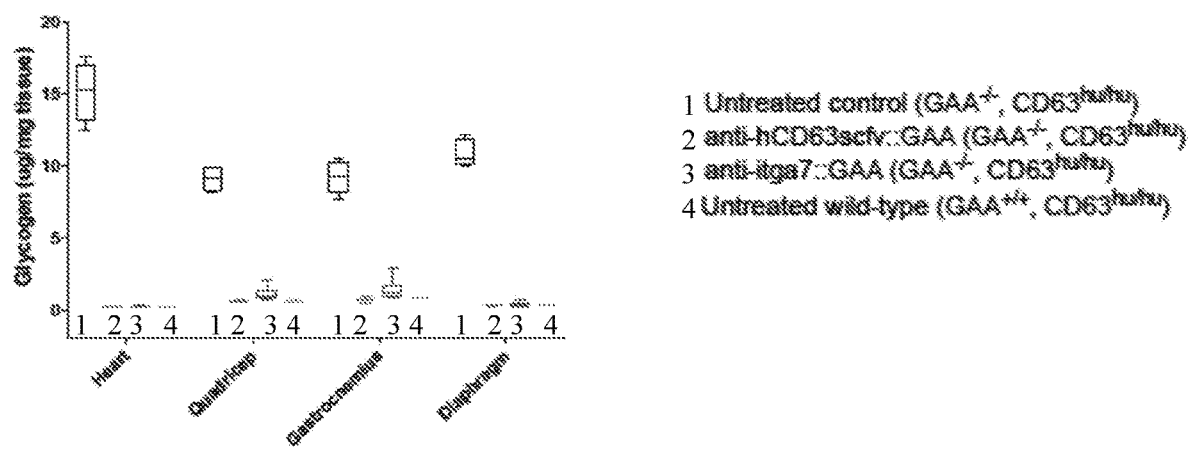

FIG. 10A and FIG. 10B depict the use of other membrane proteins as guides, such as anti-ITGA7 (Integrin alpha-7) scFv fusion proteins to guide GAA. FIG. 10A shows GAA activity (y-axis) of C2C12 mouse myoblasts incubated overnight with anti-mouse CD63-GAA or anti-moue ITGA7-GAA with or without the presence of 5 mM M6P. FIG. 10B shows GAA KO mice humanized for CD63 (GAA−/−; CD63hu/hu) that were given plasmids encoding an scFv:: GAA format of anti-hCD63::GAA (2) or a full-length IgG4:: GAA format of anti-mouse integrin alpha-7 (3) by hydrodynamic delivery (HDD), then tissue glycogen levels were measured 3 weeks post-HDD. Untreated control mice, GAA−/−;CD63hu/hu (1) and untreated wild-type GAA control mice, GAA+/+;CD63hu/hu (4) were also tested for glycogen levels in the same tissues.

Figure 11:
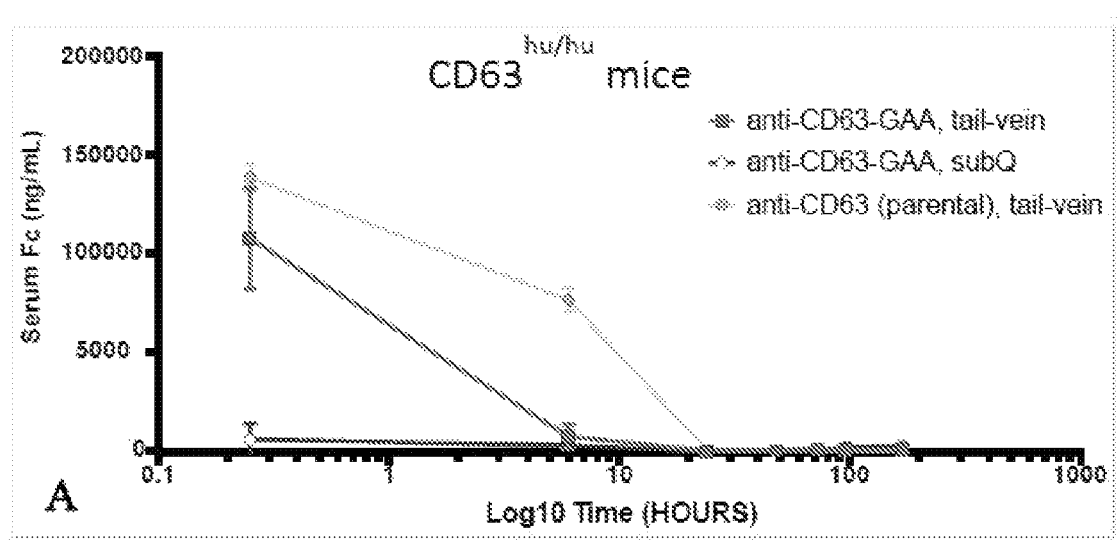
Figure 11:
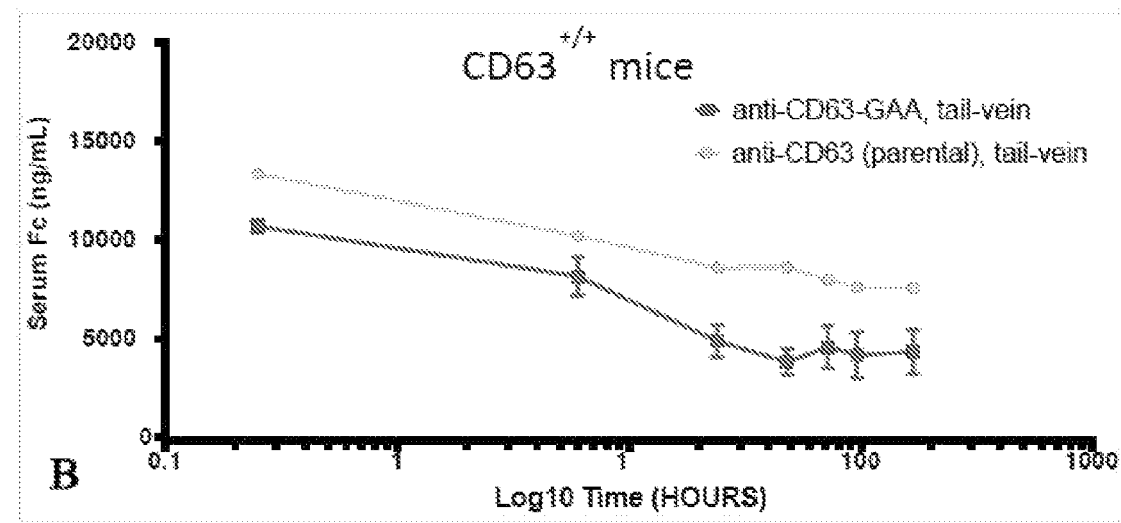

FIG. 11 illustrates serum clearance of a full-length anti-CD63 antibody fused to GAA (i.e. full-length IgG4 antibody) in CD63hu/hu mice compared to WT CD63+/+ mice. Plasmids expressing the heavy and light chain of an anti-CD63 antibody fused to GAA were injected via the tail vein of each mouse. The serum pK of anti-CD63(full length IgG4)::GAA was observed to clear from serum within 24 hours.

Figure 12A:
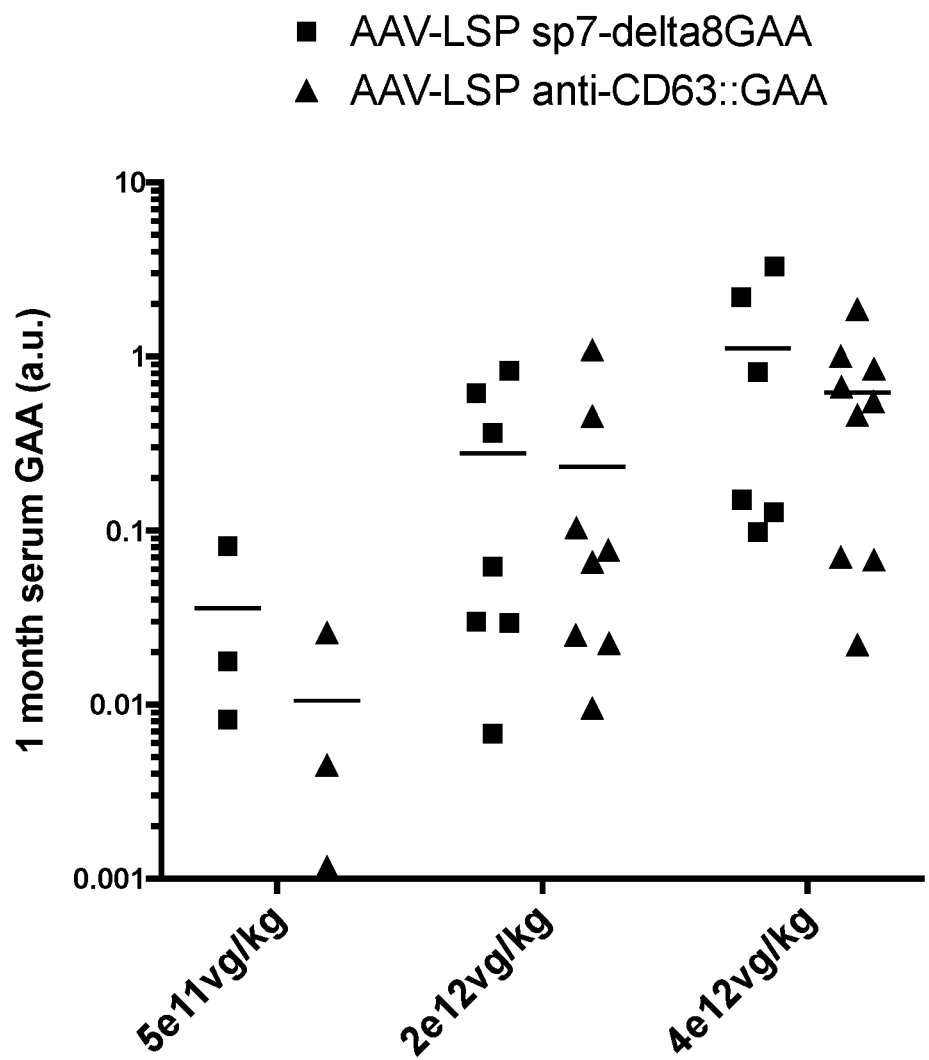

FIG. 12A is a dot plot depicting serum levels of GAA (arbitrary units "a.u."; y-axis) at one-month post-AAV injection as a function of as a function of enzyme construct and dose. Squares represent AAV-LSP-Δ8GAA. Pyramids represent AAV-anti-hCD63scFv::GAA. Both constructs provided a liver-specific promoter (LSP) to drive expression). Dose is provided as viral genome (vg) per kilogram (kg) of the mouse.

Figure 12B:
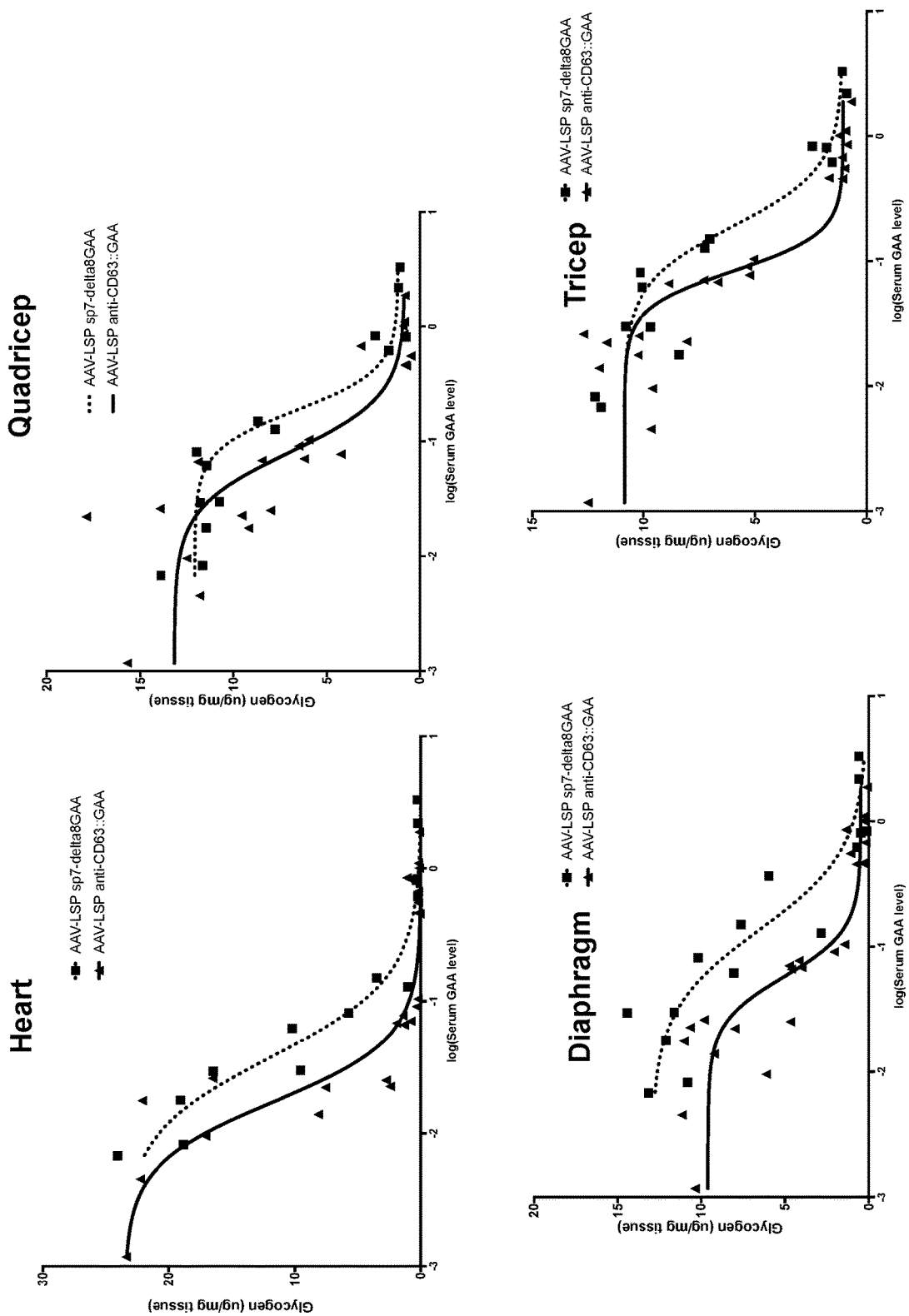

FIG. 12B provides dot blots depicting the levels of glycogen in micrograms per milligram of tissue (heart, quadricep, diaphragm, or tricep) as a function of GAA serum levels. Squares represent AAV-LSP-Δ8GAA. Pyramids represent AAV-anti-hCD63scFv::GAA. Both constructs provided a liver-specific promoter (LSP) to drive expression).

Figure 13:
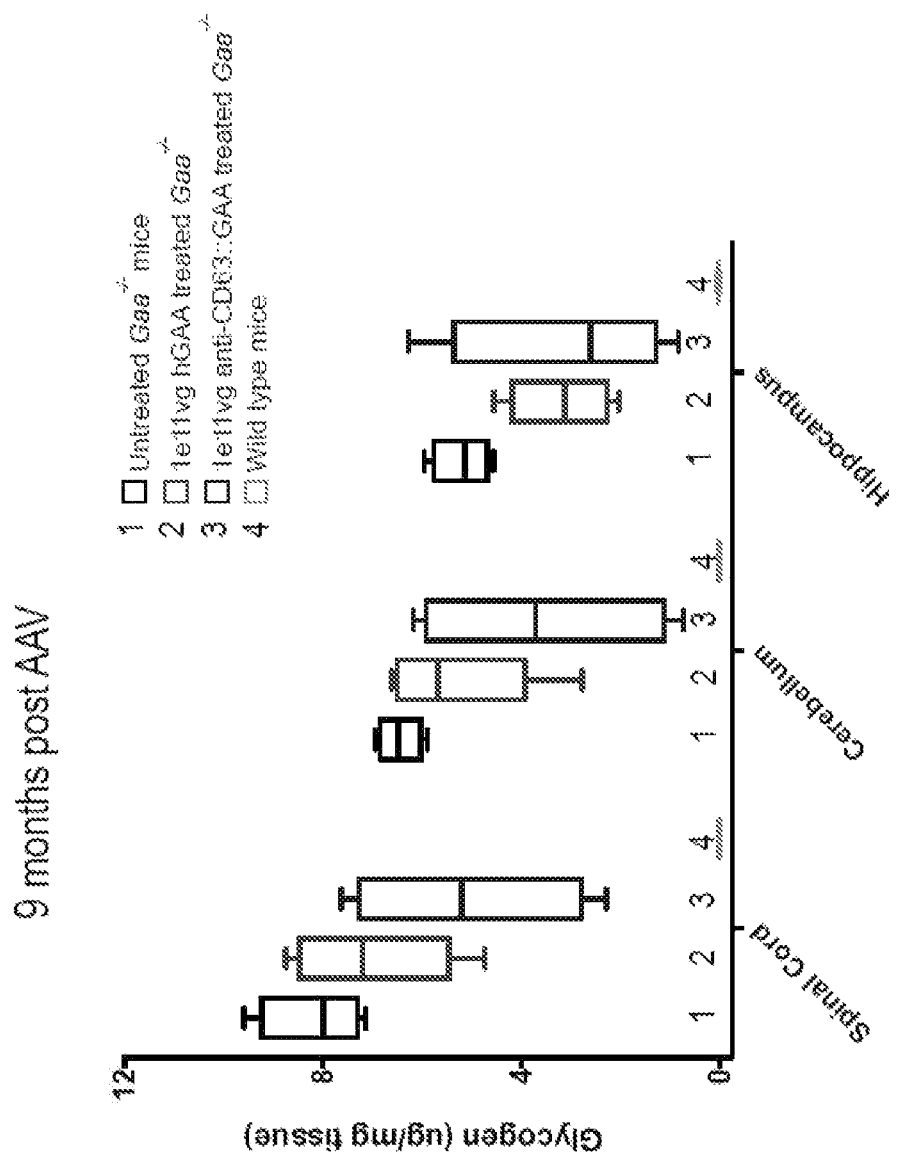

FIG. 13 is a bar graph depicting the amount of stored glycogen in micrograms per milligram of CNS tissue as a function of delivered enzyme/vector (9 month study). The X-axis depicts each CNS tissue (spinal cord, cerebellum or hippocampus) sampled from wild-type mice comparators (each Lane 4) or KO mice (GAA−/−) that were untreated (each Lane 1), or given plasmids encoding GAA (each Lane 2) or ScFv-GAA fusion (each Lane 3). It was an unexpected finding that the mice treated with fusion protein exhibited a more robust decrease is glycogen stores in CNS tissue compared to delivery of vector encoding GAA without any fused binding domain.

Figure 14A:
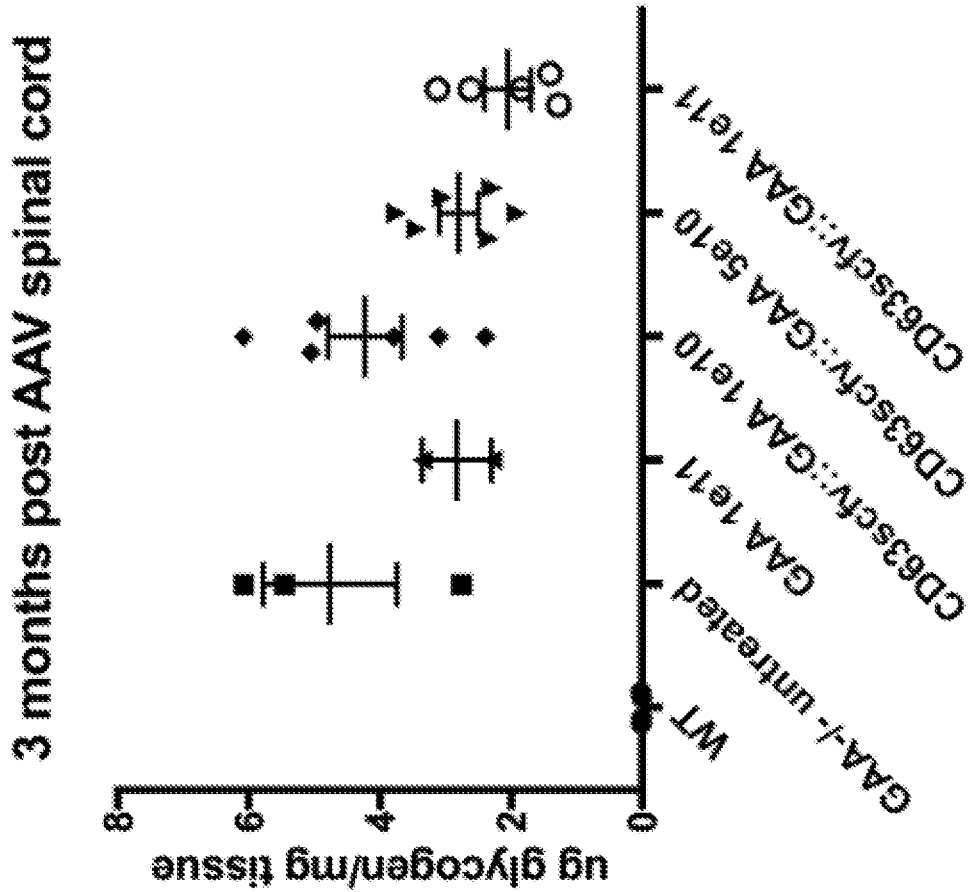

FIG. 14A is a graph depicting the amount of stored glycogen per mg of spinal cord tissue (ug glycogen/mg tissue; y-axis) 3 months after AAV delivery of GAA in a specific vector construct at a specific dose (vg=viral genomes). Glycogen levels are provided for wild-type mice (Lane 1; x-axis) compared to KO mice (GAA−/−) that were untreated (Lane 2; x-axis), or given plasmids encoding GAA (each Lane 3; x-axis) or varying doses of anti-CD63ScFv-GAA fusion (Lanes 4-6; x-axis). Stored glycogen levels in spinal cord decrease with increasing dose of ScFv-GAA fusion, with the 1e11 vg dose providing greater benefit to the subject than an equivalent dose of GAA alone (no fusion).

Figure 14B:
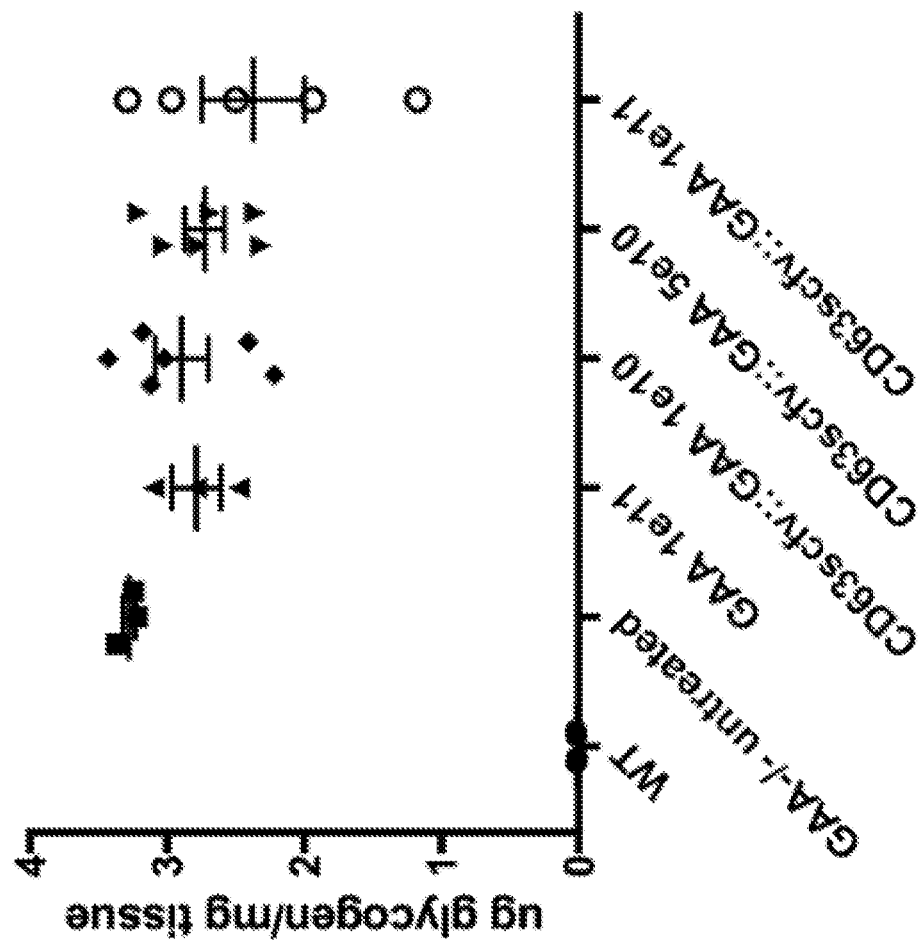

FIG. 14B is a graph depicting the amount of stored glycogen per mg of brain tissue (ug glycogen/mg tissue; y-axis) 3 months after AAV delivery of GAA in a specific vector constructs at a specific dose (vg=viral genomes). Glycogen levels are provided for wild-type mice (Lane 1; x-axis) compared to KO mice (GAA−/−) that were untreated (Lane 2; x-axis), or given plasmids encoding GAA (each Lane 3; x-axis) or varying doses of anti-CD63ScFv-GAA fusion (Lanes 4-6; x-axis). Stored glycogen levels in brain decrease with increasing dose of ScFv-GAA fusion, with the 1e11 vg dose providing greater benefit to the subject than an equivalent dose of GAA alone (no fusion).

DESCRIPTION

This invention is not limited to particular embodiments, compositions, methods and experimental conditions described, as such embodiments, compositions, methods and conditions may vary. The terminology used herein is for the purpose of describing particular embodiments only, and is not intended to be limiting, since the scope of the present invention will be limited only by the appended claims.

Although any methods and materials similar or equivalent to those described herein can be used in the practice or testing of the present invention, some preferred methods and materials are now described. All publications cited herein are incorporated herein by reference to describe in their entirety. Unless defined otherwise, all technical and scientific terms used herein have the same meaning as commonly understood by one of ordinary skill in the art to which this invention belongs.

"Blood Brain Barrier" refers to the semipermeable membrane barrier that separates the blood from the brain and extracellular fluid in the central nervous system. The barrier blocking the passage of, or selectively transports, certain substances to the brain and spinal cord. The blood-brain barrier is formed by brain endothelial cells.

"Therapeutically effective amount" refers to an amount or dosage of the vector delivered to a subject such that the subject achieves a consistent blood level (serum/plasma level) of the encoded therapeutic protein. Generally, concentrations of from about $1\times10^9$ to about $1\times10^{16}$ genomes vector may be utilized in the method. The dosage for delivery to liver may be about $1\times10^{10}$ to $5\times10^{13}$ AAV genomes per 1 kg. The dosage will be adjusted to balance the therapeutic benefit of crossing the blood brain barrier to achieve the desired effect of the molecule against any side effects and such dosages may vary depending upon the recombinant vector that is employed. The levels of expression of the transgene can be monitored in the blood circulation by extraction of serum or plasma to determine the frequency of dosage of vectors that will achieve a steady state of circulating protein. One skilled in the art can determine specific values for an effective amount by, for example, performing experiments to determine consistent blood levels of therapeutic protein over consecutive days, weeks or months following vector delivery. Suitable experiments to test for circulating therapeutic protein are known in the art, including but not limited to western blot, ELISA, LC-MS, etc. In one example, a therapeutically effective amount of scFv-GAA fusion protein in the CNS is an amount of viral vector that produces sufficient amounts of scFv-GAA fusion protein to reduce stored glycogen in CNS tissue, for example in spinal cord, cerebellum or hippocampus tissue.

CNS Disorders

Various brain disorders may benefit from the mode of delivery of therapeutic proteins described herein. CNS disorders and disorders with neurological symptoms amenable to protein therapies include, but are not limited to: Alzheimer's, brain cancer, Behcet's Disease, cerebral Lupus, Creutzfeldt-Jakob Disease, dementia, epilepsy, encephalitis, Friedreich's Ataxia, Guillain-Barre Syndrome, Gaucher Disease, headache, hydrocephalus, Huntington's disease, intracranial hypertension, leukodystrophy, migraine, myasthenia gravis, muscular dystrophy, multiple sclerosis, narcolepsy, neuropathy, Prader-Willi Syndrome, Parkinson's disease, Rett Syndrome, restless leg syndrome, sleep disorders, subarachnoid haemorrhage, stroke, traumatic brain injury, trigeminal neuralgia, transient ischaemic attack, and Von Hippel-Lindau Syndrome (angiomatosis).

Anti-CD63-fusion delivery of a therapeutic protein to the CNS may be particularly beneficial due to its ubiquitous expression, its role as a membrane protein of extracellular vesicles (EVs; e.g. exosomes) and association with integrins. Other cell-surface receptors with similar properties as internalizing effectors include: ITGA7, CD9, CD63, CD81, CD82, and CD151, and may be tissue or cell-type specific in order to enhance the desired location of the uptake, as discussed throughout the specification.

Anti-transferrin-fusion delivery of a therapeutic protein to the CNS has also been shown to be particularly beneficial. Trafficking and delivery of therapeutic proteins therefore will be enhanced by the use of delivery mechanisms, such as anti-receptor fusion to particular blood-brain-barrier (BBB) targets. Some BBB targets have been shown as beneficial for CNS uptake (Zuchero, et al., 6 Jan. 2016, Neuron, 89(1): 70-82; Boado, R J et al, Mol Pharm. 2014 Aug. 4; 11(8): 2928-2934; each of which reference is incorporated herein in its entirety by reference). Other cell-surface receptors with similar BBB uptake properties to transferrin receptors include, but are not limited to: insulin receptor, CD98, and Basigin (Bsg).

In some embodiments, the targeted delivery of the therapeutic protein to CNS tissue (e.g. brain) is employed by use of anti-transferrin receptor or anti-insulin receptor, or anti-CD98 or anti-Bsg. The therapeutic protein may also be fused to an internalizing effector antibody, as discussed herein throughout the specification. In some embodiments, the targeted delivery of the therapeutic protein to CNS and to peripheral tissues is employed by use of an anti-insulin receptor delivery domain, for example to enhance both brain uptake as well as peripheral uptake (Boado, R J et al, 2014, supra; Yu et al., 25 May 2011, Science Transl Med. 3:84ra44, each of which reference is incorporated herein in its entirety by reference).

Exemplary anti-transferrin receptor, anti-insulin receptor, anti-CD98, and anti-Bsg antibodies and portions thereof that may be useful as part of a multidomain therapeutic protein as described herein are well-known in the art (see, e.g., US20170174778; US20150196663; U.S. Pat. No. 9,629, 801; US20180002433; WO2016081643; US20180134797; WO2014189973; US20150110791; U.S. Pat. No. 9,708, 406; US20170260292; WO2016081640; US20180057604; U.S. Pat. No. 9,611,323; WO2012075037; WO2018210898, US20180344869, US20180282408, US20170051071, WO2016207240, WO2015101588, US20160324984; US20180222993; WO2017055542; US20180222992; WO2017055540; Cabezon, I., et al. Mol Pharm. 2015 Nov. 2; 12(11):4137-45; Yu Y J, et al. Sci Transl Med (2014) 6:261ra154; Couch, et al. Sci Transl Med. 2013 May 1; 5(183):183ra57, 1-12; and Yu et al., 2011, supra, for non-limiting exemplary anti-transferrin receptor antibodies; see, e.g., WO2017214456, WO2017214458, WO2017214462; WO2008017828; WO2015146132; WO2016094566; WO2013078377; WO2017026497; Hayes G M et al. Int. J. Cancer (2015) 137:710-20; and Bixby, et al. American Society Hematology 2015 Meeting, Abstract #3809 for non-limiting exemplary anti-CD98 antibodies; see, e.g., WO2011112566; US20110223176; US20140079711; WO2010036460; U.S. Pat. No. 8,618,264; WO2005092381; WO2018165619; and WO2017186182 for non-limiting exemplary anti-BSG antibodies; see, e.g., U.S. Pat. No. 8,974,791; WO2013081706; US20160152719; US20160208006; US20170114152; Pardridge, W M et al. BioDrugs. 2018 April; 32(2):169-176; Boado R J et al. Mol. Pharm. (2016) 13:3241-6; Cieniewicz A M, et al. Diabetes (2017) 66:206-217; Bexwada, P. et al. J Pharmacol Exp Ther. 2016 February; 356(2):466-73; and Bedinger, D H, et al. J Pharmacol Exp Ther. 2015 April; 353(1):35-43 for non-limiting exemplary anti-insulin receptor antibodies; each of which reference is incorporated in its entirety by reference). A skilled artisan could readily link these well-known antibodies, or antigen binding portions thereof (e.g., scFv derived therefrom) to a therapeutic protein as described herein to make and use a multidomain therapeutic protein as described herein.

Lysosomal Storage Diseases

"Enzyme-deficiency diseases" include non-lysosomal storage disease such as Krabbe disease (galactosylceramidase), phenylketonuria, galactosemia, maple syrup urine disease, mitochondrial disorders, Friedreich ataxia, Zellweger syndrome, adrenoleukodystrophy, Wilson disease, hemochromatosis, ornithine transcarbamylase deficiency, methylmalonic academia, propionic academia, and lysosomal storage diseases. "Lysosomal storage diseases" include any disorder resulting from a defect in lysosome function. Currently, approximately 50 lysosomal storage disorders have been identified, the most well-known of which include Tay-Sachs, Gaucher, and Niemann-Pick disease. The pathogeneses of the diseases are ascribed to the buildup of incomplete degradation products in the lysosome, usually due to loss of protein function. Lysosomal storage diseases are caused by loss-of-function or attenuating variants in the proteins whose normal function is to degrade or coordinate degradation of lysosomal contents. The proteins affiliated with lysosomal storage diseases include enzymes, receptors and other transmembrane proteins (e.g., NPC1), post-translational modifying proteins (e.g., sulfatase), membrane transport proteins, and non-enzymatic cofactors and other soluble proteins (e.g., GM2 ganglioside activator). Thus, lysosomal storage diseases encompass more than those disorders caused by defective enzymes per se, and include any disorder caused by any molecular defect. Thus, as used herein, the term "enzyme" is meant to encompass those other proteins associated with lysosomal storage diseases.

The nature of the molecular lesion affects the severity of the disease in many cases, i.e. complete loss-of-function tends to be associated with pre-natal or neo-natal onset, and involves severe symptoms; partial loss-of-function is associated with milder (relatively) and later-onset disease. Generally, only a small percentage of activity needs to be restored to have to correct metabolic defects in deficient cells. Table 1 lists some of the more common lysosomal storage diseases and their associated loss-of-function proteins. Lysosomal storage diseases are generally described in Desnick and Schuchman, 2012.

Lysosomal storage diseases are a class of rare diseases that affect the degradation of myriad substrates in the lysosome. Those substrates include sphingolipids, mucopolysaccharides, glycoproteins, glycogen, and oligosaccharides, which can accumulate in the cells of those with disease leading to cell death. Organs affected by lysosomal storage diseases include the central nervous system (CNS), the peripheral nervous system (PNS), lungs, liver, bone, skeletal and cardiac muscle, and the reticuloendothelial system.

Options for the treatment of lysosomal storage diseases include enzyme replacement therapy (ERT), substrate reduction therapy, pharmacological chaperone-mediated therapy, hematopoietic stem cell transplant therapy, and gene therapy. An example of substrate reduction therapy includes the use of Miglustat or Eliglustat to treat Gaucher Type 1. These drugs act by blocking synthase activity, which reduces subsequent substrate production. Hematopoietic stem cell therapy (HSCT), for example, is used to ameliorate and slow-down the negative central nervous system phenotype in patients with some forms of MPS. See R. M. Boustany, "Lysosomal storage diseases—the horizon expands," 9(10) Nat. Rev. Neurol. 583-98, October 2013; which reference is incorporated herein in its entirety by reference. Table 1 lists some lysosomal storage diseases and their associated enzymes or other proteins.

TABLE 1

Lysosomal Storage Diseases

| Class | Disease | Involved Enzyme/Protein |
|---|---|---|
| Sphingo-lipidoses | Fabry disease | α-Galactosidase A |
| | Farber lipogranulomatosis | Ceramidase |
| | Gaucher disease type I | β-Glucosidase |
| | Gaucher disease types II and III | Saposin-C activator |
| | Niemann-Pick diseases types A and B | Sphingomyelinase |
| | GM1-gangliosidosis | β-Galactosidase |
| | GM2-gangliosidosis (Sandhoff) | β-Hexosaminidase A and B |
| | GM2-gangliosidosis (Tay-Sachs) | β-Hexosaminidase A |
| | GM2-gangliosidosis (GM2-activator deficiency) | GM2-activator protein |
| | GM3-gangliosidosis | GM3 synthase |
| | Metachromatic leukodystrophy | Arylsulfatase A |
| | Sphingolipid-activator deficiency | Sphingolipid activator |
| Mucopoly-saccharidoses | MPS I (Scheie, Hurler-Scheie, and Hurler disease) | α-Iduronidase |
| | MPS II (Hunter) | Iduronidase-2-sulphatase |
| | MPS IIIA (Sanfilippo A) | Heparan N-sulphatase |
| | MPS IIIB (Sanfilippo B) | N-acetyl-α-glucosaminidase |

TABLE 1-continued

Lysosomal Storage Diseases

| Class | Disease | Involved Enzyme/Protein |
|---|---|---|
| | MPS IIIC (Sanfilippo C) | Acetyl-CoA; α-glucosamide N-acetyltransferase |
| | MPS IIID (Sanfilippo D) | N-acetylglucosamine-6-sulphatase |
| | MPS IVA (Morquio syndrome A) | N-acetylgalactosamine-6-sulphate sulphatase |
| | MPS IVB (Morquio syndrome B) | β-Galactosidase |
| | MPS VI (Maroteaux-Lamy) | N-acetylgalactosamine-4-sulphatase (arylsulphatase B) |
| | MPS VII (Sly disease) | β-Glucuronidase |
| | MPS IX | Hylauronidase |
| Glycogen storage disease | Pompe (glycogen storage disease type II) | α-Glucosidase 2 |
| Lipid metabolism | Lysosomal acid lipase deficiency (LAL-D; Wolman disease) | Lysosomal acid lipase |

Two of the most common LSDs are Pompe disease and Fabry disease. Pompe disease, which has an estimated incidence of 1 in 10,000, is caused by defective lysosomal enzyme alpha-glucosidase (GAA), which results in the deficient processing of lysosomal glycogen. Accumulation of lysosomal glycogen occurs predominantly in skeletal, cardiac, and hepatic tissues. Infantile onset Pompe causes cardiomegaly, hypotonia, hepatomegaly, and death due to cardiorespiratory failure, usually before 2 years of age. Adult onset Pompe occurs as late as the second to sixth decade and usually involves only skeletal muscle. Treatments currently available include Genzyme's MYOZYME®/LUMIZYME® (alglucosidase alfa), which is a recombinant human alpha-glucosidase produced in CHO cells and administered by intravenous infusion.

Fabry disease, which has including mild late onset cases an overall estimated incidence of 1 in 3,000, is caused by defective lysosomal enzyme alpha-galactosidase A (GLA), which results in the accumulation of globotriaosylceramide within the blood vessels and other tissues and organs. Symptoms associated with Fabry disease include pain from nerve damage and/or small vascular obstruction, renal insufficiency and eventual failure, cardiac complications such as high blood pressure and cardiomyopathy, dermatological symptoms such as formation of angiokeratomas, anhidrosis or hyperhidrosis, and ocular problems such as cornea verticillata, spoke-like cataract, and conjunctival and retinal vascular abnormalities. Treatments currently available include Genzyme's FABRAZYME® (agalsidase beta), which is a recombinant human alpha-galactosidase A produced in CHO cells and administered by intravenous infusion; Shire's REPLAGAL™ (agalsidase alfa), which is a recombinant human alpha-galactosidase A produced in human fibroblast cells and administered by intravenous infusion; and Amicus's GALAFOLD™ (migalastat or 1-deoxygalactonojirimycin) an orally administered small molecule chaperone that shifts the folding of abnormal alpha-galactosidase A to a functional conformation.

Current treatments for lysosomal storage diseases are less than optimal. For example, ERT generally must be administered at a high frequency and a high dose, such as biweekly and up to 40 mg/kg. Also, some replaced enzymes can be immunologically cross-reactive (CRIM), stimulating production of IgG in the subject and thus hindering delivery of the enzyme to the lysosome via the mannose-6-phosphate (M6P) receptor. The IgGs might shield the M6P residues of the replacement enzyme, and the antigen-IgG-antibody complex may be taken up into cellular lysosomes via the Fc receptor, thereby shunting the replacement enzyme preferentially to macrophages.

Delivery of replacement enzymes to the appropriate affected tissues is also inefficient (see Table 2 and Desnick & Schuchman, "Enzyme replacement therapy for lysosomal diseases: lessons from 20 years of experience and remaining challenges," 13 Annu. Rev. Genomics Hum. Genet. 307-35, 2012), which reference is incorporated herein in its entirety by reference. For example, patients undergoing long-term enzyme replacement therapy for Infantile Pompe can still suffer from hypernasal speech, residual muscle weakness, ptosis, ostepenia, hearing loss, risk for aspiration, dysphagia, cardiac arrhythmia, and difficulty swallowing. Doses of replacement enzyme oftentimes must be increased over time to 40 mg/kg weekly or biweekly.

TABLE 2

Inefficient tissue targeting of ERT

| Disease | Subtype(s) | Easy to reach tissue | Hard to reach tissue |
|---|---|---|---|
| Gaucher disease | Type 1 | Spleen, liver, bone marrow | Bone |
| | Types 2 and 3 | Spleen, liver, bone marrow | Bone, brain |
| Fabry disease | Classic and late onset | Vascular endothelium | Kidney, heart |
| Mucopolysaccharidoses | All | Spleen, liver, bone marrow | Bone, brain, cartilage |
| α-Mannosidosis | — | Spleen, liver, bone marrow | Bone, brain |
| Niemann-Pick disease | Type B | Spleen, liver, bone marrow | Alveolar macrophages |
| Pompe disease | Infantile | — | Heart, smooth and skeletal muscle |
| | Later onset | — | Smooth muscle and respiratory skeletal muscle |

Endogenous mannose-6 phosphate receptor (MPR) mediates the transport of most recombinant enzymes to the lysosome. Two complementary forms of MPR exist: cation-independent (CI-MPR), and cation dependent (CD-MPR). Knock-outs of either form have missorted lysosomal enzymes. Lysosomal hydrolases are synthesized in the endoplasmic reticulum and move to the cis-Golgi network, where they are covalently modified by the addition of mannose-6-phosphate (M6P) groups. The formation of this marker depends on the sequential effect of two lysosomal enzymes: UDP-N-acetylglucosamine-1-phosphotransferase (GlcNac-phosphotransferase) and N-acetylglucosamine-1-phosphodiester-α-N-acetyl-glucosaminidase (uncovering enzyme). GlcNac-phosphotransferase catalyzes the transfer of a GlcNAc-1-phosphate residue from UDP-GlcNAc to C6 positions of selected mannoses in high-mannose type oligosaccharides of the hydrolases. Then, the uncovering enzyme removes the terminal GlcNAc, exposing the M6P recognition signal. At the trans-Golgi network, the M6P signal allows the segregation of lysosomal hydrolases from all other types of proteins through selective binding to the M6P receptors. The clathrin-coated vesicles produced bud off from the trans-Golgi network and fuse with late endosomes. At the low pH of the late endosome, the hydrolases dissociate from the M6P receptors and the empty receptors are recycled to the Golgi apparatus for further rounds of transport.

With the exception of β-glucocerebrosidase, which is delivered via the mannose receptor, recombinant lysosomal enzymes comprise M6P glycosylation and are delivered to the lysosome primarily via CI-MPR/IGF2R. Glycosylation/CI-MPR-mediated enzyme replacement delivery however does not reach all clinically relevant tissues (Table 2). Improvement to enzyme replacement therapy have centered on improving CI-MPR delivery by (i) increasing surface expression of CI-MPR using the β2-agonist clenbuterol (Koeberl et al., "Enhanced efficacy of enzyme replacement therapy in Pompe disease through mannose-6-phosphate receptor expression in skeletal muscle," 103(2) Mol. Genet. Metab. 107-12, 2011, which reference is incorporated herein in its entirety by reference), (ii) increasing the amount of M6P residues on enzyme (Zhu et al., "Conjugation of mannose-6-phosphate-containing oligosaccharides to acid alpha-glucosidase improves the clearance of glycogen in Pompe mice," 279(48) J. Biol. Chem. 50336-41, 2004, which reference is incorporated herein in its entirety by reference), or (iii) fusing an IGF-II domain to the enzyme (Maga et al., "Glycosylation-independent lysosomal targeting of acid alpha-glucosidase enhances muscle glycogen clearance in Pompe mice," 288(3) J. Biol. Chem. 1428-38, 2013, which reference is incorporated herein in its entirety by reference).

A large number of lysosomal storage diseases are inadequately treated by enzyme replacement therapy or gene therapy mainly due to poor targeting of the replacement enzyme to the relevant tissue or organ, negative immunological reactions in the recipient host, and low serum half-life. A need exists for improved enzyme replacement therapies that enhance and promote better tissue biodistribution and lysosomal uptake of the enzyme, especially in the brain and spinal cord without undesirable intrathecal injections. Applicants have developed an improved enzyme replacement therapy using CI-MPR independent binding protein-guided delivery of enzymes and liver expression to provide enzyme to the lysosome of target affected tissues, particularly CNS tissues.

Lysosomal storage diseases can be categorized according to the type of product that accumulates within the defective lysosome. Sphingolipidoses are a class of diseases that affect the metabolism of sphingolipids, which are lipids containing fatty acids linked to aliphatic amino alcohols (reviewed in S. Hakomori, "Glycosphingolipids in Cellular Interaction, Differentiation, and Oncogenesis," 50 Annual Review of Biochemistry 733-764, July 1981; which reference is incorporated herein in its entirety by reference). The accumulated products of sphingolipidoses include gangliosides (e.g., Tay-Sachs disease), glycolipids (e.g., Fabry's disease), and glucocerebrosides (e.g., Gaucher's disease).

Mucopolysaccharidoses are a group of diseases that affect the metabolism of glycosaminoglycans (GAGS or mucopolysaccharides), which are long unbranched chains of repeating disaccharides that help build bone, cartilage, tendons, corneas, skin and connective tissue (reviewed in J. Muenzer, "Early initiation of enzyme replacement therapy for the mucopolysaccharidoses," 111(2) Mol. Genet. Metab. 63-72 (February 2014); Sasisekharan et al., "Glycomics approach to structure-function relationships of glycosaminoglycans," 8(1) Ann. Rev. Biomed. Eng. 181-231 (December 2014); each of which reference is incorporated herein in its entirety by reference). The accumulated products of mucopolysaccharidoses include heparan sulfate, dermatan sulfate, keratin sulfate, various forms of chondroitin sulfate, and hyaluronic acid. For example, Morquio syndrome A is due to a defect in the lysosomal enzyme galactose-6-sulfate sulfatase, which results in the lysosomal accumulation of keratin sulfate and chondroitin 6-sulfate.

Glycogen storage diseases (a.k.a., glycogenosis) result from a cell's inability to metabolize (make or break-down) glycogen. Glycogen metabolism is moderated by various enzymes or other proteins including glucose-6-phosphatase, acid alpha-glucosidase, glycogen de-branching enzyme, glycogen branching enzyme, muscle glycogen phosphorylase, liver glycogen phosphorylase, muscle phosphofructokinase, phosphorylase kinase, glucose transporter, aldolase A, beta-enolase, and glycogen synthase. An exemplar lysosomal storage/glycogen storage disease is Pompe's disease, in which defective acid alpha-glucosidase causes glycogen to accumulate in lysosomes. Symptoms include hepatomegaly, muscle weakness, heart failure, and in the case of the infantile variant, death by age 2 (see DiMauro and Spiegel, "Progress and problems in muscle glycogenosis," 30(2) Acta Myol. 96-102 (October 2011); which reference is incorporated herein in its entirety by reference).

"Multidomain therapeutic protein" includes (i) a single protein that contains more than one functional domain, (ii) a protein that contains more than one polypeptide chain, and (iii) a mixture of more than one protein or more than one polypeptide. The term polypeptide is generally taken to mean a single chain of amino acids linked together via peptide bonds. The term protein encompasses the term polypeptide, but also includes more complex structures. That is, a single polypeptide is a protein, and a protein can contain one or more polypeptides associated in a higher order structure. For example, hemoglobin is a protein containing four polypeptides: two alpha globin polypeptides and two beta globin polypeptides. Myoglobin is also a protein, but it contains only a single myoglobin polypeptide.

The multidomain therapeutic protein comprises one or more polypeptide(s) and at least two domains providing two functions. One of those domains is the "enzyme domain" which provides the replacement of a defective protein activity associated with an enzyme deficiency disease. The other of those domains is the "delivery domain" which provides binding to an internalizing effector. Thus, a single polypeptide that provides an enzyme replacement activity and the ability to bind to an internalizing effector (a.k.a. internalizing effector-binding protein (delivery domain activity) is a multidomain therapeutic protein. Also, a mixture of proteins, wherein one protein provides the enzyme function, and another protein provides the internalizing effector binding activity, is a multidomain therapeutic protein. FIG. 1A depicts various exemplars of multidomain therapeutic proteins. In one example (FIG. 1A, panel A), the multidomain therapeutic protein contains an enzyme (represented by the hexagon) and a bispecific antibody (the IE-BP) that binds the enzyme (hashed lines) and an internalizing effector (solid lines). Here, one arm of the bispecific antibody binds non-covalently to the enzyme, and the other arm binds non-covalently to the internalizing effector, thereby enabling the internalization of the replacement enzyme into the cell or subcellular compartment. In another example (panel B), the multidomain therapeutic protein comprises a single protein containing two polypeptides, one polypeptide having enzyme function and the other having delivery domain function. Here, the enzyme is fused to an immunoglobulin Fc domain or heavy chain constant region, which associates with the Fc domain of the enzyme half-antibody to form the bifunctional multidomain therapeutic protein. The embodiment depicted in panel B is similar to that in panel A, except that the enzyme is covalently attached to one of the half-antibodies, rather than through antigen-antibody interaction at the immunoglobulin variable domain of the half-antibody.

In other examples, the multidomain therapeutic protein consists of the enzyme covalently linked (directly or indirectly through a linker) to the delivery domain. In one embodiment, the enzyme is attached to the C-terminus of an immunoglobulin molecule (e.g., the heavy chain or alternatively the light chain). In another embodiment, the enzyme is attached to the N-terminus of the immunoglobulin molecule (e.g., the heavy chain or alternatively the light chain). In these exemplars, the immunoglobulin molecule is the delivery domain. In yet another embodiment, the enzyme is attached to the C-terminus of a scFv molecule that binds the internalizing effector.

In one embodiment, the multidomain therapeutic protein comprises at least two, and in some embodiments no more than two, delivery domains, each of which is directed toward a distinct epitope, either on the same antigen or on two different antigens. In one embodiment, the first delivery domain binds to a lysosomal trafficking molecule or other internalizing effector (e.g., CD63) or other similar cell-surface receptor, such as ITGA7, CD9, CD63, CD81, CD82, or CD151. In another embodiment, the second delivery domain binds to a transcytosis effector to facilitate transcellular transport of the multidomain therapeutic protein. In one embodiment, the transcytosis effector is inter alia an LDL receptor, an IgA receptor, a transferrin receptor, or a neonatal Fc receptor (FcRn). In a specific embodiment, the transcytosis delivery domain comprises a molecule that binds to a transferrin receptor, such as e.g., an anti-transferrin receptor antibody or an anti-transferrin receptor scFv molecule. Tuma and Hubbard, "Transcytosis: Crossing Cellular Barriers," Physiological Reviews, 83(3): 871-935 (1 Jul. 2003) is incorporated herein by reference for cell surface receptors that mediate transcytosis that are useful in the practice of the subject invention. In one embodiment, a second delivery domain binds to a transferrin receptor, or other similar cell-surface protein, such as an insulin receptor, CD98, or Basigin (Bsg). Each multidomain therapeutic protein comprising at least two delivery domains also comprises at least one enzyme domain, e.g., each of the at least two delivery domains may or may not be independently associated an enzyme domain in a manner described herein (e.g., via an antigen-antibody interaction, via a direct covalent link, via an indirect covalent link, etc.), wherein at least one of the at least two delivery domains is associated with the enzyme domain. Additionally, each of the at least two delivery domains may independently comprise an antibody, a half-body, or an scFv (e.g., an scFv fused with an Fc).

"Enzyme domain" or "enzyme" denotes any protein associated with the etiology or physiological effect of an enzyme deficiency disease. An enzyme includes the actual enzyme, transport protein, receptor, or other protein that is defective and which is attributed as the molecular lesion that caused the disease. An enzyme also includes any protein that can provide a similar or sufficient biochemical or physiological activity that replaces or circumvents the molecular lesion of the disease. For example, an "isozyme" may be used as an enzyme. Examples of lysosomal storage disease-related proteins include those listed in Table 1 as "Involved Enzyme/Protein" and any known or later discovered protein or other molecule that circumvents the molecular defect of the enzyme-deficiency disease.

In some embodiments, the enzyme is a hydrolase, including esterases, glycosylases, hydrolases that act on ether bonds, peptidases, linear amidases, diphosphatases, ketone hydrolases, halogenases, phosphoamidases, sulfohydrolases, sulfinases, desulfinases, and the like. In some embodiments, the enzyme is a glycosylase, including glycosidases and N-glycosylases. In some embodiments, the enzyme is a glycosidase, including alpha-amylase, beta-amylase, glucan 1,4-alpha-glucosidase, cellulose, endo-1,3(4)-beta-glucanase, inulinase, endo-1,4-beta-xylanase, endo-1,4-b-xylanase, dextranase, chitinase, polygalacturonidase, lysozyme, exo-alpha-sialidase, alpha-glucosidase, beta-glucosidase, alpha-galactosidase, beta-galactosidase, alpha-mannosidase, beta-mannosidase, beta-fructofuranosidase, alpha,alpha-trehalose, beta-glucuronidase, xylan endo-1,3-beta-xylosidase, amylo-alpha-1,6-glucosidase, hyaluronoglucosaminidase, hyaluronoglucuronidase, and the like.

In the case of Pompe disease, in which the molecular defect is a defect in α-glucosidase activity, enzymes include human alpha-glucosidase, and "isozymes" such as other alpha-glucosidases, engineered recombinant alpha-glucosidase, other glucosidases, recombinant glucosidases, any protein engineered to hydrolyze a terminal non-reducing 1-4 linked alpha-glucose residue to release a single alpha-glucose molecule, any EC 3.2.1.20 enzyme, natural or recombinant low pH carbohydrate hydrolases for glycogen or starches, and glucosyl hydrolases such as sucrase isomaltase, maltase glucoamylase, glucosidase II, and neutral alpha-glucosidase.

An "internalizing effector" includes a protein, in some cases a receptor protein, that is capable of being internalized into a cell or that otherwise participates in or contributes to retrograde membrane trafficking. Internalization effector, internalizing effector, internalization receptor, and internalizing receptor are used interchangeably herein. In some instances, the internalizing effector is a protein that undergoes transcytosis; that is, the protein is internalized on one side of a cell and transported to the other side of the cell (e.g., apical-to-basal). In many embodiments, the internalizing effector protein is a cell surface-expressed protein or a soluble extracellular protein. However, the present invention also contemplates embodiments in which the internalizing effector protein is expressed within an intracellular compartment such as the endosome, endoplasmic reticulum, Golgi, lysosome, etc. For example, proteins involved in retrograde membrane trafficking (e.g., pathways from early/recycling endosomes to the trans-Golgi network) may serve as internalizing effector proteins in various embodiments of the present invention. In any event, the binding of the delivery domain to an internalizing effector protein causes the entire multidomain therapeutic protein, and any molecules associated therewith (e.g., enzyme), to also become internalized into the cell. As explained below, internalizing effector proteins include proteins that are directly internalized into a cell, as well as proteins that are indirectly internalized into a cell.

Internalizing effector proteins that are directly internalized into a cell include membrane-associated molecules with at least one extracellular domain (e.g., transmembrane proteins, GPI-anchored proteins, etc.), which undergo cellular internalization, and are preferably processed via an intracellular degradative and/or recycling pathway. Specific non-limiting examples of internalizing effector proteins that are directly internalized into a cell include, e.g., CD63, MHC-I (e.g., HLA-B27), Kremen-1, Kremen-2, LRP5, LRP6, LRP8, transferrin receptor, LDL-receptor, LDL-related protein 1 receptor, ASGR1, ASGR2, amyloid precursor protein-like protein-2 (APLP2), apelin receptor (APLNR), MAL (Myelin And Lymphocyte protein, a.k.a. VIP17), IGF2R, vacuolar-type H+ ATPase, diphtheria toxin receptor, folate receptor, glutamate receptors, glutathione receptor, leptin receptors, scavenger receptors (e.g., SCARA1-5, SCARB1-3, CD36), and the like.

In one embodiment, the internalizing effector is expressed in several tissue types and is useful in treatment where targeting of both the CNS and a peripheral cell type is desired. Internalizing effectors useful in trafficking to both CNS and peripheral cell types include, but are not limited to CD63, MHC-I, vacuolar-type H+ ATPase, IGF2R, Integrin alpha-7 (ITGA7), LRP5, LRP6, LRP8, Kremen-2, LDL-receptor, LDL-related protein 1 receptor, amyloid precursor protein-like protein-2 (APLP2), apelin receptor (APLNR), PRLR, MAL (myelin and lymphocyte protein (MAL), diphtheria toxin receptors, HBEGF (heparin binding EGF like growth factor), glutathione receptors, glutamate receptors, leptin receptors, and folate receptors. In certain embodiments, the internalizing effector is prolactin receptor (PRLR). It was discovered that PRLR is, not only a target for certain therapeutic applications, but also an effective internalizing effector protein on the basis of its high rate of internalization and turn-over. The potential for PRLR as an internalizing effector protein, for example, is illustrated in WO2015/026907, where it is demonstrated, inter alia, that anti-PRLR antibodies are effectively internalized by PRLR-expressing cells in vitro.

Targeting internalizing effectors expressed by several cell types may be useful where targeting of both the CNS and a peripheral cell type is desired, e.g., in treating disease such as Fabry disease, Gaucher disease, MPS I, MPS II, MPS IIIA, MPS MB, MPS HID, MPS IVB, MPS VI, MPS VII, MPS IX, Pompe disease, Lysosomal acid lipase deficiency, Metachromatic leukodystrophy, Niemann-Pick diseases types A, B, and C2, Alpha mannosidosis, Neuraminidase deficiency, Sialidosis, Aspartylglycosaminuria, Combined saposin deficiency, Atypical Gaucher disease, Farber lipogranulomatosis, Fucosidosis, and Beta mannosidosis.

In another embodiment, the internalizing effector is expressed in a few tissue types. In one example, the internalizing effector may target bone and cartilage preferentially. Effectors useful in trafficking to CNS, and to either or both bone and cartilage include, but are not limited to Collagen X, Integrin alpha 10 (ITGA10), Fibroblast growth factor receptor 3 (FGFR3), Fibroblast growth factor receptor isoform C (FGFR3C), Hyaluronan and proteoglycan link protein 1 (CRTL1), Aggrecan, Collagen II, and Kremen-1. Such effectors are useful in treatment where targeting of both the CNS and the skeleton and cartilage is desired.

Targeting internalizing effectors preferentially expressed by bone and cartilage may be useful where targeting both the CNS and the skeleton and cartilage is desired, e.g., in treating disease such as MPS I, MPS II, MPS MA, MPS MB, MPS HID, MPS IVA, MPS IVB, MPS VI, MPS VII, MPS IX, Beta mannosidosis, Gaucher disease, atypical Gaucher disease, combined Saposin deficiency, Aspartylglycosaminuria, Farber lipogranulomatosis, Sialidosis, Neuraminidase deficiency, Mucopolysaccharidoses, and Alpha mannosidosis.

In yet another embodiment, the internalizing effector is expressed preferentially in a particular tissue or cell type, such as macrophages, monocytes, and microglia. Effectors useful in trafficking to CNS, and to macrophages include, but are not limited to scavenger receptor A1-5 (SCARA1-5), SCARB1-3, CD36, MSR1 (macrophage scavenger receptor 1), MRC1 (macrophage mannose receptor 1), VSIG4 (V-set and immunoglobulin domain-containing protein 4), CD68 (Macrosialin), and CSF1R (Macrophage colony-stimulating factor 1 receptor). Such effectors are useful in treatment where targeting of both the CNS and macrophages is desired. CNS macrophages may be referred to as microglia.

Targeting internalizing effectors expressed preferentially by macrophages (monocytes or microglia) may be useful where targeting both CNS and macrophages (or microglia) is desired, e.g., in treating disease such as lysosomal acid lipase deficiency, Gaucher disease, Atypical Gaucher disease, combined Saposin deficiency, and Farber lipogranulomatosis.

In certain embodiments, the internalizing effector is a kidney specific internalizing effector, such as CDH16 (Cadheri-16), CLDN16 (Claudn-16), KL (Klotho), PTH1R (parathyroid hormone receptor), SLC22A13 (Solute carrier family 22 member 13), SLC5A2 (Sodium/glucose cotransporter 2), and UMOD (Uromodulin).

Targeting internalizing effectors preferentially expressed in the kidney may be useful where targeting both the CNS and the kidney is desired, e.g., in treating disease such as Fabry disease, Alport syndrome, polycystic kidney disease, and Thrombotic Thrombocytopenic Purpura.

In yet another embodiment, the internalizing effector is expressed preferentially in a particular tissue or cell type, such as the liver. Effectors useful in trafficking to CNS, and to liver include, but are not limited to ASGR1 and ASGR2. Such effectors are useful in treatment where targeting of both the CNS and liver is desired.

Targeting internalizing effectors expressed preferentially in the liver may be useful where targeting both CNS and liver is desired, e.g., in treating disease such as lysosomal acid lipase deficiency, Gaucher disease, MPS VI, MPS VII, MPS II, Niemann-Pick diseases types A, B, and C2, Sialidosis, Neuraminidase deficiency, atypical Gaucher disease, combined Saposin deficiency, Farber lipogranulomatosis.

In some embodiments, the internalizing effector is a muscle specific internalizer, such as BMPR1A (Bone morphogenetic protein receptor 1A), m-cadherin, CD9, MuSK (muscle-specific kinase), LGR4/GPR48 (G protein-coupled receptor 48), cholinergic receptor (nicotinic) alpha 1, CDH15 (Cadheri-15), ITGA7 (Integrin alpha-7), CACNG1 (L-type calcium channel subunit gamma-1), CACNA1S (L-type calcium channel subunit alpha-15), CACNG6 (L-type calcium channel subunit gamma-6), SCN1B (Sodium channel subunit beta-1), CHRNA1 (ACh receptor subunit alpha), CHRND (ACh receptor subunit delta), LRRC14B (Leucine-rich repeat-containing protein 14B), dystroglycan (DAG1), and POPDC3 (Popeye domain-containing protein 3).

Targeting internalizing effectors expressed preferentially by muscle may be useful where targeting both the CNS and muscle tissue is desired, e.g., in treating disease such as Pompe disease.

In some embodiments, the internalizing effector is ITGA7, ITGA10, CD9, CD63, ALPL2, MSR1, ASGR1, ASGR2, or PRLR. Antibodies to ITGA7, ITGA10, CD9, CD63, APLP2, MSR1, ASGR1, ASGR2 or PRLR are well-known in the art (see, e.g., R & D Systems "Integrin alpha 7: Products" for exemplary non-limiting anti-IGTA7 antibodies; see, e.g., U.S. Pat. No. 8,048,991, US20120034625, U.S. Pat. No. 8,563,255, US20140099716, US20160319023, WO2018138322, and U.S. Pat. No. 10,087,253 for exemplary non-limiting examples of anti-ITGA10 antibodies; see, e.g., WO201102982; WO2014185908; US20160115229; WO2017134197; U.S. Pat. No. 9,738,717; and de Goeij B E et al. Mol. Cancer Ther. (2016) November; 15 (11): 2688-2697 for exemplary non-limiting anti-CD63 antibodies; see, e.g., U.S. Pat. No. 543,153A; U.S. Pat. Nos. 5,441,931A; 5,677,146A; and 5,935,854A for exemplary non-limiting anti-APLP2 antibodies; see, e.g., R&D Systems product sheet for MAB27081; R&D Systems product sheet for AF2708; AbCam Product Sheet ab 1515707; Yu X, et al., J. Biol. Chem., 2011; 286 (21): 18795-806; and N Nishijima, et al., Front Immunol, 2017; 8 (0): 379 for exemplary non-limiting examples of anti-MSR1 antibodies; see, e.g., WO2017058944 for exemplary non-limiting examples of anti-ASGR1 antibody; see, e.g., Origene Antibodies for ASGR2 available at origene.com for non-limiting exemplary anti-ASGR2 antibodies; see, e.g., U.S. Pat. Nos. 9,649,374; 9,302,015; US20130171147; U.S. Pat. No. 10,106,616; WO2015026907; U.S. Pat. No. 9,777,063; WO2011069795; US20130272968; US20140141003; WO2011069799; US20120315276; WO2012163932; U.S. Pat. No. 9,241,989; WO2012136519; WO2011069798; WO2019011719; U.S. Pat. No. 8,883,979; US20140065158; WO2015187596; U.S. Pat. No. 9,353, 186; WO2018102304; US20130022606; U.S. Pat. No. 9,688,764; US20130129739; US20160002342; US20150056222; US20150056221; US20170008965; US20150093393; WO2011069797; US20160251442; US20180094066; WO2014036076; US20180185504; US20140271659; WO2011069794; WO2014143909; US20160319029; U.S. Pat. Nos. 9,545,451; 9,023,357; US20150252116; WO2011069796 Kelly M P, et al., Mol. Cancer Ther. (2017) July; 16 (7): 1299-1311; Otto C. et al. Endocrinology (2015) 156:4365-73 2017 Jan. 20; and Andreev J et al., Mol. Cancer Ther. (2017) April; 16 (4): 681-693 for exemplary non-limiting anti-PRLR antibodies; each of which references is incorporated herein in its entirety by reference). A skilled artisan could readily link these well-known antibodies, or antigen binding portions thereof (e.g., scFv derived therefrom) to a therapeutic protein as described herein to make and use a multidomain therapeutic protein as described herein.

In those embodiments in which the internalizing effector (IE) is directly internalized into a cell, the delivery domain can be, e.g., an antibody or antigen-binding fragment of an antibody that specifically binds the IE, or a ligand or portion of a ligand that specifically interacts with the IE. For example, if the IE is Kremen-1 or Kremen-2, the delivery domain can comprise or consist of a Kremen ligand (e.g., DKK1) or Kremen-binding portion thereof. As another example, if the IE is a receptor molecule such as ASGR1, the delivery domain can comprise or consist of a ligand specific for the receptor (e.g., asialoorosomucoid [ASOR] or Beta-GalNAc) or a receptor-binding portion thereof.

Internalizing effector proteins that are indirectly internalized into a cell include proteins and polypeptides that do not internalize on their own but become internalized into a cell after binding to or otherwise associating with a second protein or polypeptide that is directly internalized into the cell. Proteins that are indirectly internalized into a cell include, e.g., soluble ligands that are capable of binding to an internalizing cell surface-expressed receptor molecule. A non-limiting example of a soluble ligand that is (indirectly) internalized into a cell via its interaction with an internalizing cell surface-expressed receptor molecule is transferrin. In embodiments, wherein the IE is transferrin (or another indirectly internalized protein), the binding of the delivery domain to the IE, and the interaction of IE with transferrin receptor (or another internalizing cell-surface expressed receptor molecule), causes the entire delivery domain, and any molecules associated therewith (e.g., the enzyme), to become internalized into the cell concurrent with the internalization of the IE and its binding partner.

In those embodiments in which the IE is indirectly internalized into a cell, the delivery domain can be, e.g., an antibody, antigen-binding fragment of an antibody, or an scFv that specifically binds IE, or a receptor or portion of a receptor that specifically interacts with the soluble effector protein. For example, if the IE is a cytokine, the delivery domain can comprise or consist of the corresponding cytokine receptor or ligand-binding portion thereof.

An exemplar IE is CD63, which is a member of the tetraspanin superfamily of cell surface proteins that span the cell membrane four times. CD63 is expressed in virtually all tissues and is thought to be involved in forming and stabilizing signaling complexes. CD63 localizes to the cell membrane, lysosomal membrane, and late endosomal membrane. CD63 is known to associate with integrins and may be involved in epithelial-mesenchymal transitioning. See H. Maecker et al., "The tetraspanin superfamily: molecular facilitators," 11(6) FASEB J. 428-42, May 1997; and M. Metzelaar et al., "CD63 antigen. A novel lysosomal membrane glycoprotein, cloned by a screening procedure for intracellular antigens in eukaryotic cells," 266 J. Biol. Chem. 3239-3245, 1991; each of which references is incorporated herein in its entirety by reference.

Another exemplar IE is amyloid beta (A4) precursor-like protein 2 ("APLP2"), a ubiquitously expressed member of the APP (amyloid precursor protein) family. APLP2 is a membrane-bound protein known to interact with major histocompatibility complex (MHC) class I molecules (e.g., Kd). It binds Kd at the cell surface and is internalized in a clathrin-dependent manner with Kd in tow. See Tuli et al., "Mechanism for amyloid precursor-like protein 2 enhancement of major histocompatibility complex class I molecule degradation," 284 The Journal of Biological Chemistry 34296-34307 (2009); which reference is incorporated herein in its entirety by reference.

Another IE exemplar is the prolactin receptor (PRLR). The prolactin receptor is a member of the type I cytokine receptor family and upon ligand binding and subsequent dimerization activates "the tyrosine kinases Jak2, Fyn and Tec, the phosphatase SHP-2, the guanine nucleotide exchange factor Vav, and the signaling suppressor SOCS," (see Clevenger and Kline, "Prolactin receptor signal transduction," 10(10) Lupus 706-18 (2001), abstract; each of which reference is incorporated herein in its entirety by reference). The prolactin receptor undergoes endocytotic recycling and can be found in lysosomal fractions. See Genty et al., "Endocytosis and degradation of prolactin and its receptor in Chinese hamster ovary cells stably transfected with prolactin receptor cDNA," 99(2) Mol. Cell Endocrinol. 221-8 (1994); and Ferland et al., "The effect of chloroquine on lysosomal prolactin receptors in rat liver," 115(5) Endocrinology 1842-9 (1984), which reference is incorporated herein in its entirety by reference.

As used herein, "immunological reaction" generally means a patient's immunological response to an outside or "non-self" protein. This immunological response includes an allergic reaction and the development of antibodies that interfere with the effectiveness of the replacement enzyme. Some patients may not produce any of the non-functioning protein, thus rendering the replacement enzyme a "foreign" protein. For example, repeated injection of recombinant GLA (rGLA) to those Fabry patients who lack GLA frequently results in an allergic reaction. In other patients, the production of antibodies against rGLA has been shown to decrease the effectiveness of the replacement enzyme in treating the disease. See for example Tajima et al. ("Use of a Modified α-N-Acetylgalactosaminidase (NAGA) in the Development of Enzyme Replacement Therapy for Fabry Disease," 85(5) Am. J. Hum. Genet. 569-580 (2009)), which reference is incorporated herein in its entirety by reference, which discusses the use of modified NAGA as the "isozyme" to replace GLA. The modified NAGA has no immunological cross-reactivity with GLA, and "did not react to serum from a patient with Fabry disease recurrently treated with a recombinant GLA." Id, abstract.

An "immunosuppressive agent" includes drugs and/or proteins that result in general immunosuppression and may be used to prevent cross-reactive immunological materials (CRIM) against replacement enzymes, e.g., GAA or GLA respectively in a patient with Pompe or Fabry's disease. Non-limiting examples of an immunosuppressive agent include methotrexate, mycophenolate mofetil, cyclophosphamide, rapamycin DNA alkylating agents, anti-CD20 antibody, anti-BAFF antibody, anti-CD3 antibody, anti-CD4 antibody, and any combination thereof.

Regulatory elements, e.g., promoters, that are specific to a tissue, e.g., liver, enhance expression of nucleic acid sequences, e.g., genes, under the control of such regulatory element in the tissue for which the regulatory element is specific. Non-limiting examples of a liver specific regulatory element, e.g., liver specific promoters, may be found in Chuah et al. (2014) *Mol. Ther.* 22:1605-13, which reference is incorporated herein in its entirety by reference.

The term "protein" means any amino acid polymer having more than about 20 amino acids covalently linked via amide bonds. Proteins contain one or more amino acid polymer chains, generally known in the art as "polypeptides". Thus, a polypeptide may be a protein, and a protein may contain multiple polypeptides to form a single functioning biomolecule. Disulfide bridges (i.e., between cysteine residues to form cystine) may be present in some proteins. These covalent links may be within a single polypeptide chain, or between two individual polypeptide chains. For example, disulfide bridges are essential to proper structure and function of insulin, immunoglobulins, protamine, and the like. For a recent review of disulfide bond formation, see Oka and Bulleid, "Forming disulfides in the endoplasmic reticulum," 1833(11) Biochim Biophys Acta 2425-9 (2013), which reference is incorporated herein in its entirety by reference.

As used herein, "protein" includes biotherapeutic proteins, recombinant proteins used in research or therapy, trap proteins and other Fc-fusion proteins, chimeric proteins, antibodies, monoclonal antibodies, human antibodies, bispecific antibodies, antibody fragments, nobodies, recombinant antibody chimeras, scFv fusion proteins, cytokines, chemokines, peptide hormones, and the like. Proteins may be produced using recombinant cell-based production systems, such as the insect bacculovirus system, yeast systems (e.g., *Pichia* sp.), mammalian systems (e.g., CHO cells and CHO derivatives like CHO-K1 cells). For a recent review discussing biotherapeutic proteins and their production, see Ghaderi et al., "Production platforms for biotherapeutic glycoproteins. Occurrence, impact, and challenges of non-human sialylation," 28 Biotechnol Genet Eng Rev. 147-75 (2012), which reference is incorporated herein in its entirety by reference.

The term "antibody", as used herein, includes immunoglobulin molecules comprising four polypeptide chains, two heavy (H) chains and two light (L) chains inter-connected by disulfide bonds. Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3. The term "high affinity" antibody refers to those antibodies having a binding affinity to their target of at least $10^{-9}$M, at least $10^{-10}$ M; at least $10^{-11}$ M; or at least $10^{-12}$ M, as measured by surface plasmon resonance, e.g., BIACORE™ or solution-affinity ELISA. The term "antibody" may encompass any type of antibody, such as e.g. monoclonal or polyclonal. Moreover, the antibody may be or any origin, such as e.g. mammalian or non-mammalian. In one embodiment, the antibody may be mammalian or avian. In a further embodiment, the antibody may be or human origin and may further be a human monoclonal antibody.

The phrase "bispecific antibody" includes an antibody capable of selectively binding two or more epitopes. Bispecific antibodies generally comprise two different heavy chains, with each heavy chain specifically binding a different epitope—either on two different molecules (e.g., antigens) or on the same molecule (e.g., on the same antigen). If a bispecific antibody is capable of selectively binding two different epitopes (a first epitope and a second epitope), the affinity of the first heavy chain for the first epitope will generally be at least one to two or three or four orders of magnitude lower than the affinity of the first heavy chain for the second epitope, and vice versa. The epitopes recognized by the bispecific antibody can be on the same or a different target (e.g., on the same or a different protein). Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions, and such sequences can be expressed in a cell that expresses an immunoglobulin light chain. A typical bispecific antibody has two heavy chains each having three heavy chain CDRs, followed by (N-terminal to C-terminal) a CH1 domain, a hinge, a CH2 domain, and a CH3 domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding or one or both of the heavy chains to one or both epitopes.

The phrase "heavy chain," or "immunoglobulin heavy chain" includes an immunoglobulin heavy chain constant region sequence from any organism, and unless otherwise specified includes a heavy chain variable domain. Heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a CH1 domain, a hinge, a CH2 domain, and a CH3 domain. A functional fragment of a heavy chain includes a fragment that is capable of specifically recognizing an antigen (e.g., recognizing the antigen with a KD in the micromolar, nanomolar, or picomolar range), that is capable of expressing and secreting from a cell, and that comprises at least one CDR.

The phrase "light chain" includes an immunoglobulin light chain constant region sequence from any organism, and unless otherwise specified includes human kappa and lambda light chains. Light chain variable (VL) domains typically include three light chain CDRs and four framework (FR) regions, unless otherwise specified. Generally, a full-length light chain includes, from amino terminus to carboxyl terminus, a VL domain that includes FR1-CDR1-FR2-CDR2-FR3-CDR3-FR4, and a light chain constant domain. Light chains that can be used with this invention include e.g., those, that do not selectively bind either the first or second antigen selectively bound by the antigen-binding protein. Suitable light chains include those that can be identified by screening for the most commonly employed light chains in existing antibody libraries (wet libraries or in silico), where the light chains do not substantially interfere with the affinity and/or selectivity of the antigen-binding domains of the antigen-binding proteins. Suitable light chains include those that can bind one or both epitopes that are bound by the antigen-binding regions of the antigen-binding protein.

The phrase "variable domain" includes an amino acid sequence of an immunoglobulin light or heavy chain (modified as desired) that comprises the following amino acid regions, in sequence from N-terminal to C-terminal (unless otherwise indicated): FR1, CDR1, FR2, CDR2, FR3, CDR3, FR4. A "variable domain" includes an amino acid sequence capable of folding into a canonical domain (VH or VL) having a dual beta sheet structure wherein the beta sheets are connected by a disulfide bond between a residue of a first beta sheet and a second beta sheet.

The phrase "complementarity determining region," or the term "CDR," includes an amino acid sequence encoded by a nucleic acid sequence of an organism's immunoglobulin genes that normally (i.e., in a wildtype animal) appears between two framework regions in a variable region of a light or a heavy chain of an immunoglobulin molecule (e.g., an antibody or a T cell receptor). A CDR can be encoded by, for example, a germline sequence or a rearranged or unrearranged sequence, and, for example, by a naive or a mature B cell or a T cell. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as the result of splicing or connecting the sequences (e.g., V-D-J recombination to form a heavy chain CDR3).

The term "antibody fragment", refers to one or more fragments of an antibody that retain the ability to specifically bind to an antigen. Examples of binding fragments encompassed within the term "antibody fragment" include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546, which reference is incorporated herein in its entirety by reference), which consists of a VH domain, (vi) an isolated CDR, and (vii) an scFv, which consists of the two domains of the Fv fragment, VL and VH, joined by a synthetic linker to form a single protein chain in which the VL and VH regions pair to form monovalent molecules. Other forms of single chain antibodies, such as diabodies are also encompassed under the term "antibody" (see e.g., Holliger et al. (1993) PNAS USA 90:6444-6448; Poljak et al. (1994) Structure 2:1121-1123, which reference is incorporated herein in its entirety by reference).

The phrase "Fc-containing protein" includes antibodies, bispecific antibodies, immunoadhesins, and other binding proteins that comprise at least a functional portion of an immunoglobulin CH2 and CH3 region. A "functional portion" refers to a CH2 and CH3 region that can bind a Fc receptor (e.g., an FcγR; or an FcRn, i.e., a neonatal Fc receptor), and/or that can participate in the activation of complement. If the CH2 and CH3 region contains deletions, substitutions, and/or insertions or other modifications that render it unable to bind any Fc receptor and also unable to activate complement, the CH2 and CH3 region is not functional.

Fc-containing proteins can comprise modifications in immunoglobulin domains, including where the modifications affect one or more effector function of the binding protein (e.g., modifications that affect FcγR binding, FcRn binding and thus half-life, and/or CDC activity). Such modifications include, but are not limited to, the following modifications and combinations thereof, with reference to EU numbering of an immunoglobulin constant region: 238, 239, 248, 249, 250, 252, 254, 255, 256, 258, 265, 267, 268, 269, 270, 272, 276, 278, 280, 283, 285, 286, 289, 290, 292, 293, 294, 295, 296, 297, 298, 301, 303, 305, 307, 308, 309, 311, 312, 315, 318, 320, 322, 324, 326, 327, 328, 329, 330, 331, 332, 333, 334, 335, 337, 338, 339, 340, 342, 344, 356, 358, 359, 360, 361, 362, 373, 375, 376, 378, 380, 382, 383, 384, 386, 388, 389, 398, 414, 416, 419, 428, 430, 433, 434, 435, 437, 438, and 439.

For example, and not by way of limitation, the binding protein is an Fc-containing protein and exhibits enhanced serum half-life (as compared with the same Fc-containing protein without the recited modification(s)) and have a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at 428 and/or 433 (e.g., L/R/SI/P/Q or K) and/or 434 (e.g., H/F or Y); or a modification at 250 and/or 428; or a modification at 307 or 308 (e.g., 308F, V308F), and 434. In another example, the modification can comprise a 428L (e.g., M428L) and 434S (e.g., N434S) modification; a 428L, 259I (e.g., V259I), and a 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); a 307 and/or 308 modification (e.g., 308F or 308P).

The term "antigen-binding protein," as used herein, refers to a polypeptide or protein (one or more polypeptides complexed in a functional unit) that specifically recognizes an epitope on an antigen, such as a cell-specific antigen and/or a target antigen of the present invention. An antigen-binding protein may be multi-specific. The term "multi-specific" with reference to an antigen-binding protein means that the protein recognizes different epitopes, either on the same antigen or on different antigens. A multi-specific antigen-binding protein of the present invention can be a single multifunctional polypeptide, or it can be a multimeric complex of two or more polypeptides that are covalently or non-covalently associated with one another. The term "antigen-binding protein" includes antibodies or fragments thereof of the present invention that may be linked to or co-expressed with another functional molecule, e.g., another peptide or protein. For example, an antibody or fragment thereof can be functionally linked (e.g., by chemical coupling, genetic fusion, non-covalent association or otherwise) to one or more other molecular entities, such as a protein or fragment thereof to produce a bispecific or a multi-specific antigen-binding molecule with a second binding specificity.

As used herein, the term "epitope" refers to the portion of the antigen which is recognized by the multi-specific antigen-binding polypeptide. A single antigen (such as an antigenic polypeptide) may have more than one epitope. Epitopes may be defined as structural or functional. Functional epitopes are generally a subset of structural epitopes and are defined as those residues that directly contribute to the affinity of the interaction between the antigen-binding polypeptide and the antigen. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. Epitopes formed from contiguous amino acids are typically retained on exposure to denaturing solvents, whereas epitopes formed by tertiary folding are typically lost on treatment with denaturing solvents.

The term "domain" refers to any part of a protein or polypeptide having a particular function or structure. Preferably, domains of the present invention bind to cell-specific or target antigens. Cell-specific antigen- or target antigen-binding domains, and the like, as used herein, include any naturally occurring, enzymatically obtainable, synthetic, or genetically engineered polypeptide or glycoprotein that specifically binds an antigen.

The term "half-body" or "half-antibody", which are used interchangeably, refers to half of an antibody, which essentially contains one heavy chain and one light chain. Antibody heavy chains can form dimers, thus the heavy chain of one half-body can associate with heavy chain associated with a different molecule (e.g., another half-body) or another Fc-containing polypeptide. Two slightly different Fc-domains may "heterodimerize" as in the formation of bispecific antibodies or other heterodimers, -trimers, -tetramers, and the like. See Vincent and Murini, "Current strategies in antibody engineering: Fc engineering and pH-dependent antigen binding, bispecific antibodies and antibody drug conjugates," 7 Biotechnol. J. 1444-1450 (20912); and Shimamoto et al., "Peptibodies: A flexible alternative format to antibodies," 4(5) MAbs 586-91 (2012), each of which references is incorporated herein in its entirety by reference.

In one embodiment, the half-body variable domain specifically recognizes the internalizing effector and the half body Fc-domain dimerizes with an Fc-fusion protein that comprises a replacement enzyme (e.g., a peptibody) Id, 586.

The term "single-chain variable fragment" or "scFv" includes a single chain fusion polypeptide containing an immunoglobulin heavy chain variable region (VH) and an immunoglobulin light chain variable region (VL). In some embodiments, the VH and VL are connect by a linker sequence of 10 to 25 amino acids. ScFv polypeptides may also include other amino acid sequences, such as CL or CH1 regions. ScFv molecules can be manufactured by phage display or made by directly subcloning the heavy and light chains from a hybridoma or B-cell. Ahmad et al., Clinical and Developmental Immunology, volume 2012, article ID 98025 is incorporated herein by reference for methods of making scFv fragments by phage display and antibody domain cloning.

"Alpha-glucosidase" (or "α-glucosidase"), "α-glucosidase activity", "GAA", and "GAA activity" are used interchangeably and refer to any protein that facilitates the hydrolysis of 1,4-alpha bonds of glycogen and starch into glucose. GAA is also known inter alia as EC 3.2.1.20, maltase, glucoinvertase, glucosidosucrase, maltase-glucoamylase, alpha-glucopyranosidase, glucosidoinvertase, alpha-D-glucosidase, alpha-glucoside hydrolase, alpha-1,4-glucosidase, and alpha-D-glucoside glucohydrolase. GAA can be found in the lysosome and at the brush border of the small intestine. Patients who suffer from Pompe disease lack functioning lysosomal α-glucosidase. See S. Chiba, "Molecular mechanism in alpha-glucosidase and glucoamylase," 61(8) Biosci. Biotechnol. Biochem. 1233-9 (1997); and Hesselink et al., "Lysosomal dysfunction in muscle with special reference to glycogen storage disease type II," 1637 (2) Biochim. Biophys. Acta. 164-70 (2003), which reference is incorporated herein in its entirety by reference.

"Alpha-galactosidase A" (or "α-galactosidase A"), "α-galactosidase A activity", "α-galactosidase", "α-galactosidase activity", "GLA", and "GLA activity" are used interchangeably and refer to any protein that facilitates the hydrolysis of terminal α-galactosyl moieties from glycolipids and glycoproteins, and also hydrolyses α-D-fucosides. GLA is also known inter alia as EC 3.2.1.22, melibiase, α-D-galactosidase, α-galactosidase A, α-galactoside galactohydrolase, α-D-galactoside galactohydrolase. GLA is a lysosomal enzyme encoded by the X-linked GLA gene. Defects in GLA can lead to Fabry Disease, in which the glycolipid known as globotriaosylceramide (a.k.a. Gb3, GL-3, or ceramide trihexoside) accumulates within blood vessels (i.e., prominent vasculopathy), resulting in pain and impairment in the function of kidney, heart, skin, and/or cerebrovascular tissues. and other tissues, and organs. See for example Prabakaran et al. "Mannose 6-phosphate receptor and sortilin mediated endocytosis of α-galactosidase A in kidney endothelial cells," 7(6) PLoS One e39975 pp. 1-9 (2012), which reference is incorporated herein in its entirety by reference.

In one aspect, the invention provides a method of treating a patient (or subject) suffering from a lysosomal storage disease by administering to the patient a "multidomain therapeutic protein". The multidomain therapeutic protein enters the cells of the patient and delivers to the lysosomes an enzyme or enzymatic activity that (i.e., "replacement enzyme") that replaces the enzyme (i.e., "endogenous enzyme") or enzymatic activity that is associated with the LSD. In one embodiment, the multidomain therapeutic protein is delivered to the patient via a gene therapy vector that contains a polynucleotide that encodes the multidomain therapeutic protein.

LSDs include sphingolipidoses, a mucopolysaccharidoses, and glycogen storage diseases. In some embodiments, the LSD is any one or more of Fabry disease, Gaucher disease type I, Gaucher disease type II, Gaucher disease type III, Niemann-Pick disease type A, Niemann-Pick disease type BGM1-gangliosidosis, Sandhoff disease, Tay-Sachs disease, GM2-activator deficiency, GM3-gangliosidosis, metachromatic leukodystrophy, sphingolipid-activator deficiency, Scheie disease, Hurler-Sceie disease, Hurler disease, Hunter disease, Sanfilippo A, Sanfilippo B, Sanfilippo C, Sanfilippo D, Morquio syndrome A, Morquio syndrome B, Maroteaux-Lamy disease, Sly disease, MPS IX, and Pompe disease. In a specific embodiment, the LSD is Fabry disease. In another embodiment, the LSD is Pompe disease.

In some embodiments, the multidomain therapeutic protein comprises (a) the replacement enzyme, and (b) a molecular entity that binds an internalizing effector (delivery domain). In some cases, the replacement enzyme is any one or more of α-galactosidase, β-galactosidase, α-glucosidase, β-glucosidase, saposin-C activator, ceramidase, sphingomyelinase, β-hexosaminidase, GM2 activator, GM3 synthase, arylsulfatase, sphingolipid activator, α-iduronidase, iduronidase-2-sulfatase, heparin N-sulfatase, N-acetyl-α-glucosaminidase, α-glucosamide N-acetyltransferase, N-acetylglucosamine-6-sulfatase, N-acetylgalactosamine-6-sulfate sulfatase, N-acetylgalactosamine-4-sulfatase, β-glucuronidase, and hyaluronidase.

In some cases, the patient may not make sufficient protein such that a replacement enzyme is recognized by the patient as "non-self" and an immunological reaction ensues after administering a replacement enzyme. This is not desirable. Therefore, in some embodiments, the replacement enzyme is designed or produced in such a way as to avoid inducing an immunological reaction in the subject. One such solution is to use an "isozyme" as a replacement enzyme. An isozyme is sufficiently close to a "self" protein of the patient but has the replacement enzyme activity sufficient to ameliorate the symptoms of the LSD.

In one particular embodiment, in which the LSD is Pompe disease and the endogenous enzyme is α-glucosidase (GAA), the isozyme can be any one of acid α-glucosidase, sucrase-isomaltase (SI), maltase-glucoamylase (MGAM), glucosidase II (GANAB), and neutral α-glucosidase (C GNAC). In another particular embodiment, in which the LSD is Fabry disease and the endogenous enzyme is α-galactosidase A (GLA), the isozyme can be an α-N-acetylgalactosaminidase engineered to have GLA activity.

Provided herein are methods, other than to use an isozyme, to reduce cross-reactive immunological materials (CRIM) against the replacement enzyme. As demonstrated in FIGS. 5 and 6, administration of a multidomain therapeutic protein (e.g., via a gene therapy vector) comprising an internalizing effector binding domain and the enzyme domain reduces the level of CRIM against the replacement enzyme comprised to administration of a control therapeutic protein (lacking the internalizing effector domain and comprising an enzyme domain). As such, in one embodiment or reducing CRIM against an enzyme in a patient with a deficiency in the enzyme comprises administering to the patient the patient a multidomain therapeutic protein (or nucleic acid encoding same, e.g., a gene therapy vector containing a gene encoding the multidomain therapeutic protein, wherein the multidomain therapeutic protein comprises a delivery domain (e.g., internalizing effector binding protein) and an enzyme domain.

The multidomain therapeutic protein has an internalizing effector binding protein component that enables the uptake of the replacement enzyme into the cell. Thus, in some embodiments, the internalizing effector can be CD63, MHC-I, Kremen-1, Kremen-2, LRP5, LRP6, LRP8, transferrin receptor, LDL-receptor, LDL-related protein 1 receptor, ASGR1, ASGR2, amyloid precursor protein-like protein-2 (APLP2), apelin receptor (APLNR), PRLR (prolactin receptor), MAL (Myelin And Lymphocyte protein, a.k.a. VIP17), IGF2R, vacuolar-type H+ ATPase, diphtheria toxin receptor, folate receptor, glutamate receptors, glutathione receptor, leptin receptor, scavenger receptor, SCARA1-5, SCARB1-3, and CD36. In certain embodiments, the internalizing effector is a kidney specific internalizer, such as CDH16 (Cadheri-16), CLDN16 (Claudn-16), KL (Klotho), PTH1R (parathyroid hormone receptor), SLC22A13 (Solute carrier family 22 member 13), SLC5A2 (Sodium/glucose cotransporter 2), and UMOD (Uromodulin). In other certain embodiments, the internalizing effector is a muscle specific internalizer, such as BMPR1A (Bone morphogenetic protein receptor 1A), m-cadherin, CD9, MuSK (muscle-specific kinase), LGR4/GPR48 (G protein-coupled receptor 48), cholinergic receptor (nicotinic) alpha 1, CDH15 (Cadheri-15), ITGA7 (Integrin alpha-7), CACNG1 (L-type calcium channel subunit gamma-1), CACNA1S (L-type calcium channel subunit alpha-15), CACNG6 (L-type calcium channel subunit gamma-6), SCN1B (Sodium channel subunit beta-1), CHRNA1 (ACh receptor subunit alpha), CHRND (ACh receptor subunit delta), LRRC14B (Leucine-rich repeat-containing protein 14B), dystroglycan (DAG1), and POPDC3 (Popeye domain-containing protein 3). In some specific embodiments, the internalizing effector is ITGA7, CD9, CD63, APLP2, ASGR1, ASGR2, or PRLR.

In some embodiments, the internalizing effector-binding protein comprises an antigen-binding protein, which includes for example a receptor-fusion molecule, a trap molecule, a receptor-Fc fusion molecule, an antibody, an Fab fragment, an F(ab')2 fragment, an Fd fragment, an Fv fragment, a single-chain Fv (scFv) molecule, a dAb fragment, an isolated complementarity determining region (CDR), a CDR3 peptide, a constrained FR3-CDR3-FR4 peptide, a domain-specific antibody, a single domain antibody, a domain-deleted antibody, a chimeric antibody, a CDR-grafted antibody, a diabody, a triabody, a tetrabody, a minibody, a nanobody, a monovalent nanobody, a bivalent nanobody, a small modular immunopharmaceutical (SMIP), a camelid antibody (VHH heavy chain homodimeric antibody), and a shark variable IgNAR domain.

In one embodiment, the molecular entity that binds the internalizing effector is an antibody, an antibody fragment, or other antigen-binding protein. For example, the molecular entity can be a bispecific antibody, in which one arm binds the internalizing effector (e.g., ITGA7, CD9, CD63, PRLR, APLP2. ASGR1, ASGR2), and the other arm binds the replacement enzyme. Here, the multidomain therapeutic protein comprises the bispecific antibody and the replacement enzyme (FIG. 1A). In a specific embodiment, the disease treated is Fabry disease, and the multidomain therapeutic protein comprises GLA and a bispecific antibody that binds GLA and CD63. In a specific embodiment, the disease treated is Fabry disease, and the multidomain therapeutic protein comprises GLA and a bispecific antibody that binds GLA and ITGA7. In another specific embodiment, the disease treated is Pompe disease, and the multidomain therapeutic protein comprises GAA and a bispecific antibody that binds GAA and CD63. In another specific embodiment, the disease treated is Pompe disease, and the multidomain therapeutic protein comprises GAA and a bispecific antibody that binds GAA and ITGA7.

In another embodiment, the molecular entity that binds the internalizing effector comprises a half-antibody, and the replacement enzyme contains an Fc domain (enzyme-Fc fusion polypeptide). In one embodiment, the Fc domain of the enzyme-Fc fusion polypeptide associates with the Fc domain of the internalizing effector-specific half-body to form the multidomain therapeutic protein (FIG. 1B).

In other embodiments, the replacement enzyme is covalently linked to internalizing effector-binding protein. The enzyme-Fc fusion:half-body embodiment described in the previous paragraph (see also FIG. 1B) falls into this class, since the Fc dimer can be secured via one or more disulfide bridges. The covalent linkage between the enzyme activity domain or polypeptide and the internalization-binding domain or polypeptide may be any type of covalent bond, i.e., any bond that involved sharing of electrons. In some cases, the covalent bond is a peptide bond between two amino acids, such that the replacement enzyme and the internalizing effector-binding protein in whole or in part form a continuous polypeptide chain, as in a fusion protein. In some cases, the replacement enzyme portion and the internalizing effector-binding protein are directly linked. In other cases, a linker is used to tether the two portions. See Chen et al., "Fusion protein linkers: property, design and functionality," 65(10) Adv Drug Deliv Rev. 1357-69 (2013).

The term "linker" or "spacer" refers to a short (e.g., 2 to 25 amino acids) polypeptide that typically allow for proper folding of one or more linked components of the fusion protein, e.g., a VH linked to a VL of an scFv, a therapeutic protein (e.g., replacement enzyme) linked to a delivery domain (e.g., an anti-internalizing effector antibody) of a multidomain therapeutic protein as described herein. The linker provides a flexible junction region of the component of the fusion protein, allowing the two ends of the molecule to move independently, and may play an important role in retaining each of the two moieties' appropriate functions. Therefore, the junction region acts in some cases as both a linker, which combines the two parts together, and as a spacer, which allows each of the two parts to form its own biological structure and not interfere with the other part. Furthermore, the junction region should create an epitope that will not be recognized by the subject's immune system as foreign, in other words, will not be considered immunogenic. Linker selection may also have an effect on binding activity of the fusion molecule. (See Huston, et al, 1988, PNAS, 85:16:5879-83; Robinson & Bates, 1998, *PNAS* 95(11):5929-34; Arai, et al. 2001, *PEDS,* 14(8):529-32; and Chen, X. et al., 2013, *Advanced Drug Delivery Reviews* 65:1357-1369.) In one embodiment, the delivery domain is connected to the therapeutic polypeptide, or fragment thereof, via one or more peptide linkers. In another embodiment, the variable regions of an scFv antibody are connected to each other, or a fragment thereof, via one or more peptide linkers.

The length of the linker chain may be 2, 3, 4, 5, 6, 7, 8, 9, 10, 11, 12, 13, 14 15 or more amino acid residues, but typically is between 5 and 25 residues. Examples of linkers include polyGlycine linkers, such as Gly-Gly, Gly-Gly-Gly (3Gly), 4Gly, 5Gly, 6Gly, 7Gly, 8Gly or 9Gly. Examples of linkers also include Gly-Ser peptide linkers such as Ser-Gly, Gly-Ser, Gly-Gly-Ser, Ser-Gly-Gly, Gly-Gly-Gly-Ser, Ser-Gly-Gly-Gly, Gly-Gly-Gly-Gly-Ser, Ser-Gly-Gly-Gly-Gly, Gly-Gly-Gly-Gly-Gly-Ser, Ser-Gly-Gly-Gly-Gly-Gly, Gly-Gly-Gly-Gly-Gly-Gly-Ser, Ser-Gly-Gly-Gly-Gly-Gly-Gly, (Gly-Gly-Gly-Gly-Ser)n, and (Ser-Gly-Gly-Gly-Gly)n, wherein n=1 to 10. (Gly-Gly-Gly-Gly-Ser)n and (Ser-Gly-Gly-Gly-Gly)n are also known as (G4S)n and (S4G)n, respectively.

In some embodiment, the therapeutic protein, e.g., replacement enzyme, is covalently linked to the C-terminus of the heavy chain of an anti-internalizing effector antibody (see FIG. 1C) or to the C-terminus of the light chain (FIG. 1E). In some embodiments, the replacement enzyme is covalently linked to the N-terminus of the heavy chain of an anti-internalizing effector antibody (see FIG. 1D) or to the N-terminus of the light chain (FIG. 1F). In some embodiments, the enzyme is linked to the C-terminus of an anti-internalizing effector scFv domain (FIG. 1G).

In some cases, especially where the therapeutic protein, e.g., replacement enzyme, is not normally proteolytically processed in the lysosome, a cleavable linker is added to those embodiments of the multidomain therapeutic protein that comprise an antibody-enzyme fusion. In some embodiments, a cathepsin cleavable linker is inserted between the antibody and the replacement enzyme to facilitate removal of the antibody in the lysosome in order to a) possibly help preserve enzymatic activity by removing the sterically large antibody and b) possibly increase lysosomal half-life of the enzyme.

In one particular embodiment, the multidomain therapeutic protein is delivered to the patient or cell in a gene therapy vector that contains a polynucleotide that encodes the multidomain therapeutic protein. In one embodiment, the multidomain therapeutic protein comprises a delivery domain and an enzyme domain. In a specific embodiment, the delivery domain binds to an internalizing effector, such as CD63, MHC-I, Kremen-1, Kremen-2, LRP5, LRP6, LRP8, transferrin receptor, LDL-receptor, LDL-related protein 1 receptor, ASGR1, ASGR2, amyloid precursor protein-like protein-2 (APLP2), apelin receptor (APLNR), MAL (myelin and lymphocyte protein (MAL), IGF2R, vacuolar-type H+ ATPase, diphtheria toxin receptor, folate receptor, glutamate receptors, glutathione receptor, leptin receptors, scavenger receptor A1-5 (SCARA1-5), SCARB1-3, or CD36. In one embodiment, the delivery domain is a single-chain variable fragment (scFv) that binds to CD63 (i.e., anti-CD63 scFv). In another embodiment, the delivery domain is a single-chain variable fragment (scFv) that binds to ITGA7 (i.e., anti-ITGA7 scFv).

In one particular embodiment, the enzyme domain of the multidomain therapeutic protein comprises a hydrolase. In a specific embodiment, the enzyme domain comprises a hydrolase that is a glycosylase. In a more specific embodiment, the enzyme domain comprises a glycosylase that is a glycosidase. In a more specific embodiment, the enzyme domain is a glycosidase that is alpha-glucosidase.

Generally, disclosed herein are compositions comprising and use of polynucleotides, e.g., (m)RNA, DNA, and modified forms thereof, that encode a multidomain therapeutic protein comprising an internalizing effector domain and an enzyme domain in the treatment of lysosomal storage diseases, e.g., for the reduction of glycogen and/or the enhancement of immune tolerance for GAA in a patient with Pompe disease.

The term "polynucleotide" includes a polymer of nucleotides (e.g., RNA or DNA) that encodes at least one polypeptide, including fusion polypeptides, e.g., a multidomain therapeutic polypeptide comprising an internalizing effector domain and an enzyme domain. Polynucleotide as used herein encompasses polymers comprising both modified and unmodified nucleotides. A polynucleotide may contain one or more coding and non-coding regions. A polynucleotide can be purified from natural sources, produced using recombinant expression systems and optionally purified, chemically synthesized, etc. Where appropriate, e.g., in the case of chemically synthesized molecules, A polynucleotide can comprise nucleoside analogs such as analogs having chemically modified bases or sugars, backbone modifications, etc. A polynucleotide sequence is presented in the 5' to 3' direction unless otherwise indicated. In some embodiments, a polynucleotide is or comprises natural nucleosides (e.g., adenosine, guanosine, cytidine, uridine); nucleoside analogs (e.g., 2-aminoadenosine, 2-thiothymidine, inosine, pyrrolopyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

In some embodiments, a polynucleotide comprises one or more nonstandard nucleotide residues. The nonstandard nucleotide residues may include, e.g., 5-methyl-cytidine ("5mC"), pseudouridine ("ψU"), and/or 2-thio-uridine ("2sU"). See, e.g., U.S. Pat. No. 8,278,036 or WO2011012316, each of which is incorporated in its entirety by reference for a discussion of such residues and their incorporation into a polynucleotide. The presence of nonstandard nucleotide residues may render a polynucleotide more stable and/or less immunogenic than a control a polynucleotide with the same sequence but containing only standard residues. In further embodiments, a polynucleotide may comprise one or more nonstandard nucleotide residues chosen from isocytosine, pseudoisocytosine, 5-bromouracil, 5-propynyluracil, 6-aminopurine, 2-aminopurine, inosine, diaminopurine and 2-chloro-6-aminopurine cytosine, as well as combinations of these modifications and other nucleobase modifications. Certain embodiments may further include additional modifications to the furanose ring or nucleobase. Additional modifications may include, for example, sugar modifications or substitutions (e.g., one or more of a 2'-O-alkyl modification, a locked nucleic acid (LNA)). In some embodiments, the polynucleotide may be complexed or hybridized with additional polynucleotides and/or peptide polynucleotides (PNA). In embodiments where the sugar modification is a 2'-O-alkyl modification, such modification may include, but are not limited to a 2'-deoxy-2'-fluoro modification, a 2'-O-methyl modification, a 2'-O-methoxyethyl modification and a 2'-deoxy modification. In certain embodiments, any of these modifications may be present in 0-100% of the nucleotides—for example, more than 0%, 1%, 10%, 25%, 50%, 75%, 85%, 90%, 95%, or 100% of the constituent nucleotides individually or in combination. In some embodiments, a polynucleotide comprises messenger RNA (mRNA) molecules, which may or may not be modified, e.g., which may or may not comprise a modified nucleotide, by well-known methods to increase their stability and/or decrease their immunogenicity. In some embodiments, a polynucleotide comprises DNA molecules, which may which may or may not be modified, e.g., which may or may not comprise a modified nucleotide, by well-known methods to increase their stability and/or decrease their immunogenicity.

In some embodiments, the polynucleotide also includes a "locus-targeting nucleic acid sequence". The locus targeting sequence enables the integration of the multidomain therapeutic protein-encoding polynucleotide into the genome of the recipient host cell. In some embodiments, the locus targeting sequence include flanking homology arms to enable homologous recombination. In some embodiments, the locus targeting sequence includes guide RNA sequences and a type II Cas enzyme to facilitate integration (i.e., the CRISPR-Cas9 method). In some embodiments, the locus targeting sequence includes guide zinc-finger nuclease (ZFN) recognition sequences to facilitate integration. In some embodiments, the locus targeting sequence includes transcription activator-like effector nuclease (TALEN) recognition sequences to facilitate integration. In still other embodiments, the locus targeting sequence includes a single residue-to-nucleotide code used by BuD-derived nucleases to facilitate integration.

In some embodiments, the genomic locus into which the multidomain therapeutic protein-encoding polynucleotide is integrated is a "safe harbor locus". In one embodiment, a "safe harbor locus" enables high expression of the multidomain therapeutic protein, while not interfering with the expression of essential genes or promoting the expression of oncogenes or other deleterious genes. In one embodiment, the genomic locus is at or proximal to the liver-expressed albumin (Alb) locus, a EESYR locus, a SARS locus, position 188,083,272 of human chromosome 1 or its non-human mammalian orthologue, position 3,046,320 of human chromosome 10 or its non-human mammalian orthologue, position 67, 328,980 of human chromosome 17 or its non-human mammalian orthologue, an adeno-associated virus site 1 (AAVS1) on chromosome, a naturally occurring site of integration of AAV virus on human chromosome 19 or its non-human mammalian orthologue, a chemokine receptor 5 (CCRS) gene, a chemokine receptor gene encoding an HIV-1 coreceptor, or a mouse Rosa26 locus or its non-murine mammalian orthologue. In one embodiment, the genomic locus is an adeno-associated virus site. In one embodiment, the genomic locus for integration is selected according to the method of Papapetrou and Schambach, J. Molecular Therapy, vol. 24 (4):678-684, April 2016, which is herein incorporated by reference for the step-wise selection of a safe harbor genomic locus for gene therapy vector integration; see also Barzel et al. Nature, vol. 517:360-364, incorporated herein by reference in its entirety, for the promoterless gene targeting into the liver-expressed albumin (Alb) locus.

In some embodiments, the polynucleotide, e.g., DNA, also contains a promoter operably linked to the multidomain therapeutic protein-encoding nucleic acid sequence. In a specific embodiment, the promoter is a tissue-specific promoter that drives gene expression in a particular tissue. In one embodiment, the tissue specific promoter is a liver-specific enhancer/promoter derived from serpinal (e.g., SEQ ID NO:9) and/or is a TTR promoter (SEQ ID NO:8). In other embodiments, the promoter is a CMV promoter. In other embodiments, the promoter is a ubiquitin C promoter In one embodiment, the multidomain therapeutic protein-encoding "gene therapy vector" is any vector capable of delivering the polynucleotide encoding the multidomain therapeutic protein to a host, e.g., a patient. In some embodiments the gene therapy vector targets a specific host cell or organ, e.g., for local delivery, e.g., tissue specific delivery. Typically, local delivery requires a protein (e.g., a multidomain therapeutic protein) encoded by mRNAs be translated and expressed mainly in and/or by an organ, e.g., a liver, whereby thereby forming a depot, e.g., a liver depot for production (and secretion) of the protein. In some embodiments, a gene therapy vector delivers a multidomain therapeutic protein polynucleotide to the liver in a patient to form a liver depot. See, e.g., DeRosa et al. *Gene Therapy*, vol. 10:699-707, incorporated herein by reference in its entirety. In some embodiments, a gene therapy vector delivers a polynucleotide encoding a multidomain therapeutic protein to muscle tissue in a patient. In some embodiments, a gene therapy vector delivers a polynucleotide encoding a multidomain therapeutic protein to the brain of a patient.

Any now-known or future-developed gene therapy delivery vector, natural or engineered, can be used in the practice of this invention. In some embodiments, the gene therapy vector is a viral vector, e.g., comprises a virus, viral capsid, viral genome etc. In some embodiments, the gene therapy vector is a naked polynucleotide, e.g., an episome. In some embodiments, the gene therapy vector comprises a polynucleotide complex. Exemplary non-limiting polynucleotide complexes for use as a gene therapy vector include lipoplexes, polymersomes, polypexes, dendrimers, inorganic nanoparticles (e.g., polynucleotide coated gold, silica, iron oxide, calcium phosphate, etc.). In some embodiments, a gene therapy vector as described herein comprises a combination of a viral vector, naked polynucleotides, and polynucleotide complexes.

In one embodiment, the gene therapy vector is a virus, including a retrovirus, adenovirus, herpes simplex virus, pox virus, vaccinia virus, lentivirus, or an adeno-associated virus. In one embodiment, the gene therapy vector is an adeno-associated virus (AAV), including serotypes AAV1, AAV2, AAV3, AAV4, AAV5, AAV6, AAV7, AAV8, AAV9, AAV10, and AAV11, or engineered or naturally selected variants thereof.

In one embodiment, the polynucleotide also contains adeno-associated virus (AAV) nucleic acid sequence. In one embodiment, the gene therapy vector is a chimeric adeno-associated virus containing genetic elements from two or more serotypes. For example, an AAV vector with rep genes from AAV1 and cap genes from AAV2 (designated as AAV1/2 or AAV RC1/2) may be used as a gene therapy vector to deliver the multidomain therapeutic protein polynucleotide to a cell or a cell of a patient in need. In one embodiment, the gene therapy vector is an AAV1/2, AAV1/3, AAV1/4, AAV1/5, AAV1/6, AAV1/7, AAV1/8, AAV1/9, AAV1/10, AAV1/11, AAV2/1, AAV2/3, AAV2/4, AAV2/5, AAV2/6, AAV2/7, AAV2/8, AAV2/9, AAV2/10, AAV2/11, AAV3/1, AAV3/2, AAV3/4, AAV3/5, AAV3/6, AAV3/7, AAV3/8, AAV3/9, AAV3/10, AAV3/10, AAV4/1, AAV4/2, AAV4/3, AAV4/5, AAV4/6, AAV4/7, AAV4/8, AAV4/9, AAV4/10, AAV4/11, AAV5/1, AAV5/2, AAV5/3, AAV5/4, AAV5/6, AAV5/7, AAV5/8, AAV5/9, AAV5/10, AAV5/11, AAV6/1, AAV6/2, AAV6/3, AAV6/4, AAV6/5, AAV6/7, AAV6/8, AAV6/9, AAV6/10, AAV6/10, AAV7/1, AAV7/2, AAV7/3, AAV7/4, AAV7/5, AAV7/6, AAV7/8, AAV7/9, AAV7/10, AAV7/11, AAV8/1, AAV8/2, AAV8/3, AAV8/4, AAV8/5, AAV8/6, AAV8/7, AAV8/9, AAV8/10, AAV8/11, AAV9/1, AAV9/2, AAV9/3, AAV9/4, AAV9/5, AAV9/6, AAV9/7, AAV9/8, AAV9/10, AAV9/11, AAV10/1, AAV10/2, AAV10/3, AAV10/4, AAV10/5, AAV10/6, AAV10/7, AAV10/8, AAV10/9, AAV10/11, AAV11/1, AAV11/2, AAV11/3, AAV11/4, AAV11/5, AAV11/6, AAV11/7, AAV11/8, AAV11/9, AAV11/10, chimeric viral vector or derivatives thereof. Gao et al., "Novel adeno-associated viruses from rhesus monkeys as vectors for human gene therapy," PNAS 99(18): 11854-11859, Sep. 3, 2002, is incorporated herein by reference for AAV vectors and chimeric viral vectors useful as gene therapy vectors, and their construction and use.

In a more specific embodiment, the gene therapy vector is a chimeric AAV vector with a serotype 2 rep gene sequence and a serotype 8 cap sequence ("AAV2/8" or "AAV RC2/8).

In some embodiments, the gene therapy vector is a viral vector that has been pseudotyped (e.g., engineered) to target a specific cell, e.g., a hepatocyte. Many of the advances in targeted gene therapy using viral vectors may be summarized as non-recombinatorial (non-genetic) or recombinatorial (genetic) modification of the viral vector, which result in the pseudotyping, expanding, and/or retargeting of the natural tropism of the viral vector. (Reviewed in Nicklin and Baker (2002) Curr. Gene Ther. 2:273-93; Verheiji and Rottier (2012) Advances Virol 2012:1-15; each of which references is incorporated herein in its entirety by reference). Non-genetic approaches typically utilize an adaptor, which recognizes both a wildtype (non-modified) virus surface protein and a target cell. Soluble pseudo-receptors (for the wildtype virus), polymers such as polyethylene glycol, and antibodies or portions thereof, have been used as the virus binding domain of the adaptors, while natural peptide or vitamin ligands, and antibodies and portions thereof have been used for the cell binding domain of the adaptors described above. For example, retargeting of the viral vector to a target cell may be accomplished upon binding of the vector:adaptor complex to a protein expressed on the surface of the target cell, e.g., a cell surface protein. Such approach has been used for AAV (Bartlett et al. (1999) Nat. Biotechnol. 74: 2777-2785), adenoviruses (Hemminki et al. (2001) Cancer Res. 61: 6377-81; van Beusechem et al. (2003) Gene Therapy 10:1982-1991; Einfeld, et al. (2001) Virol. 75:11284-91; Glasgow et al. (2009) PLOS One 4:e8355), herpesviruses (Nakano et al. (2005) Mol. Ther. 11:617-24), and paramyxoviruses (Bian et al. (2005) Cancer Gene Ther. 12:295-303; Bian et al. (2005) Int. J. Oncol. 29:1359-69), Coronaviruses (Haijema et al. (2003) J. Virol. 77:4528-4538; Wurdinger et al. (2005) Gene Therapy 12:1394-1404; each of which references is incorporated herein in its entirety by reference).

A more popular approach has been the recombinatorial genetic modification of viral capsid proteins, and thus, the surface of the viral capsid. In indirect recombinatorial approaches, a viral capsid is modified with a heterologous "scaffold", which then links to an adaptor. The adaptor binds to the scaffold and the target cell. (Arnold et al. (2006) Mol. Ther. 5:125-132; Ponnazhagen et al. (2002) J Virol. 76:12900-907; see also WO 97/05266 each of which references is incorporated herein in its entirety by reference) Scaffolds such as (1) Fc binding molecules (e.g., Fc receptors, Protein A, etc.), which bind to the Fc of antibody adaptors, (2) (strept)avidin, which binds to biotinylated adaptors, (3) biotin, which binds to adaptors fused with (strept)avidin, and (4) protein:protein binding pairs that form isometric peptide bonds such as SpyCatcher, which binds a SpyTagged adaptor, have been incorporated into Ad (Pereboeva et al. (2007) Gene Therapy 14: 627-637; Park et al. (2008) Biochemical and Biophysical Research Communications 366: 769-774; Henning et al. (2002) Human Gene Therapy 13:1427-1439; Banerjee et al. (2011) Bioorganic and Medicinal Chemistry Letters 21:4985-4988), AAV (Gigout et al. (2005) Molecular Therapy 11:856-865; Stachler et al. (2008) Molecular Therapy 16:1467-1473), and togavirus (Quetglas et al. (2010) Virus Research 153: 179-196; Ohno et al. (1997) Nature Biotechnology 15:763-767; Klimstra et al. (2005) Virology 338:9-21; each of which references is incorporated herein in its entirety by reference).

In a direct recombinatorial targeting approach, a targeting ligand is directly inserted into, or coupled to, a viral capsid, i.e., protein viral capsids are modified to express a heterologous ligand. The ligand than redirects, e.g., binds, a receptor or marker preferentially or exclusively expressed on a target cell. (Stachler et al. (2006) Gene Ther. 13:926-931; White et al. (2004) Circulation 109:513-519; each of which references is incorporated herein in its entirety by reference). Direct recombinatorial approaches have been used in AAV (Park et al., (2007) Frontiers in Bioscience 13:2653-59; Girod et al. (1999) Nature Medicine 5:1052-56; Grifman et al. (2001) Molecular Therapy 3:964-75; Shi et al. (2001) Human Gene Therapy 12:1697-1711; Shi and Bartlett (2003) Molecular Therapy 7:515-525, each of which references is incorporated herein in its entirety by reference), retrovirus (Dalba et al. *Current Gene Therapy* 5:655-667; Tai and Kasahara (2008) *Frontiers in Bioscience* 13:3083-3095; Russell and Cosset (1999) *Journal of Gene Medicine* 1:300-311; Erlwein et al. (2002) *Virology* 302:333-341; Chadwick et al. (1999) *Journal of Molecular Biology* 285: 485-494; Pizzato et al. (2001) *Gene Therapy* 8:1088-1096), poxvirus (Guse et al. (2011) *Expert Opinion on Biological Therapy* 11:595-608; Galmiche et al. (1997) *Journal of General Virology* 78:3019-3027; Paul et al. (2007) *Viral Immunology* 20:664-671), paramyxovirus (Nakamura and Russell (2004) *Expert Opinion on Biological Therapy* 4:1685-1692; Hammond et al. (2001) *Journal of Virology* 75:2087-2096; Galanis (2010) *Clinical Pharmacology and Therapeutics* 88:620-625; Blechacz and Russell (2008) *Current Gene Therapy* 8:162-175; Russell and Peng (2009) *Current Topics in Microbiology and Immunology* 330:213-241), and herpesvirus (Shah and Breakefield (2006) *Current Gene Therapy* 6:361-370; Campadelli-Fiume et al. (2011) *Reviews in Medical Virology* 21:213-226; each of which references is incorporated herein in its entirety by reference).

In some embodiments, a gene therapy vector as described herein is pseudotyped to those tissues that are particularly suited for generating a regulatory response, e.g., tolerance toward, e.g., the replacement enzyme. Such tissues include, but are not limited to mucosal tissue, e.g., gut-associated lymphoid tissue (GALT), hematopoietic stem cells, and the liver. In some embodiments, the gene therapy vector, or gene encoding a multidomain therapeutic protein as described herein is expressed under the control of promoters specific for those tissues, e.g., a liver specific promoter.

In some embodiments, a gene therapy vector as described herein comprises a naked polynucleotide. For example, in some embodiments, a polynucleotide encoding a multidomain therapeutic polypeptide may be injected, e.g., intramuscularly, directly into an organ for the formation of a depot, intravenously, etc. Additional methods well-known for the enhanced delivery of naked polynucleotides include but are not limited to electroporation, sonoporation, use of a gene gun to shoot polynucleotides coated gold particles, magnetofection, and hydrodynamic delivery.

In some embodiments, a gene therapy vector as described herein comprises polynucleotide complexes, such as, but not limited to, nanoparticles (e.g., polynucleotide self-assembled nanoparticles, polymer-based self-assembled nanoparticles, inorganic nanoparticles, lipid nanoparticles, semiconductive/metallic nanoparticles), gels and hydrogels, polynucleotide complexes with cations and anions, microparticles, and any combination thereof.

In some embodiments, the polynucleotides disclosed herein may be formulated as self-assembled nanoparticles. As a non-limiting example, polynucleotides may be used to make nanoparticles which may be used in a delivery system for the polynucleotides (See e.g., International Pub. No. WO2012125987; herein incorporated by reference in its entirety). In some embodiments, the polynucleotide self-assembled nanoparticles may comprise a core of the polynucleotides disclosed herein and a polymer shell. The polymer shell may be any of the polymers described herein and are known in the art. In an additional embodiment, the polymer shell may be used to protect the polynucleotides in the core.

In some embodiment, these self-assembled nanoparticles may be microsponges formed of long polymers of polynucleotide hairpins which form into crystalline 'pleated' sheets before self-assembling into microsponges. These microsponges are densely-packed sponge like microparticles which may function as an efficient carrier and may be able to deliver cargo to a cell. The microsponges may be from 1 µm to 300 nm in diameter. The microsponges may be complexed with other agents known in the art to form larger microsponges. As a non-limiting example, the microsponge may be complexed with an agent to form an outer layer to promote cellular uptake such as polycation polyethyleneime (PEI). This complex can form a 250-nm diameter particle that can remain stable at high temperatures (150° C.) (Grabow and Jaegar, Nature Materials 2012, 11:269-269; herein incorporated by reference in its entirety). Additionally, these microsponges may be able to exhibit an extraordinary degree of protection from degradation by ribonucleases. In another embodiment, the polymer-based self-assembled nanoparticles such as, but not limited to, microsponges, may be fully programmable nanoparticles. The geometry, size and stoichiometry of the nanoparticle may be precisely controlled to create the optimal nanoparticle for delivery of cargo such as, but not limited to, polynucleotides.

In some embodiments, polynucleotides may be formulated in inorganic nanoparticles (U.S. Pat. No. 8,257,745, herein incorporated by reference in its entirety). The inorganic nanoparticles may include, but are not limited to, clay substances that are water swellable. As a non-limiting example, the inorganic nanoparticle may include synthetic smectite clays which are made from simple silicates (See e.g., U.S. Pat. Nos. 5,585,108 and 8,257,745 each of which are herein incorporated by reference in their entirety).

In some embodiments, a polynucleotide may be formulated in water-dispersible nanoparticle comprising a semiconductive or metallic material (U.S. Pub. No. 20120228565; herein incorporated by reference in its entirety) or formed in a magnetic nanoparticle (U.S. Pub. No. 20120265001 and 20120283503; each of which is herein incorporated by reference in its entirety). The water-dispersible nanoparticles may be hydrophobic nanoparticles or hydrophilic nanoparticles.

In some embodiments, the polynucleotides disclosed herein may be encapsulated into any hydrogel known in the art which may form a gel when injected into a subject. Hydrogels are a network of polymer chains that are hydrophilic, and are sometimes found as a colloidal gel in which water is the dispersion medium. Hydrogels are highly absorbent (they can contain over 99% water) natural or synthetic polymers. Hydrogels also possess a degree of flexibility very similar to natural tissue, due to their significant water content. The hydrogel described herein may be used to encapsulate lipid nanoparticles which are biocompatible, biodegradable and/or porous.

As a non-limiting example, the hydrogel may be an aptamer-functionalized hydrogel. The aptamer-functionalized hydrogel may be programmed to release one or more polynucleotides using polynucleotide hybridization. (Battig et al., J. Am. Chem. Society. 2012 134:12410-12413; herein incorporated by reference in its entirety). In some embodiment, the polynucleotide may be encapsulated in a lipid nanoparticle and then the lipid nanoparticle may be encapsulated into a hydrogel.

In some embodiments, the polynucleotides disclosed herein may be encapsulated into a fibrin gel, fibrin hydrogel or fibrin glue. In another embodiment, the polynucleotides may be formulated in a lipid nanoparticle or a rapidly eliminated lipid nanoparticle prior to being encapsulated into a fibrin gel, fibrin hydrogel or a fibrin glue. In yet another embodiment, the polynucleotides may be formulated as a lipoplex prior to being encapsulated into a fibrin gel, hydrogel or a fibrin glue. Fibrin gels, hydrogels and glues comprise two components, a fibrinogen solution and a thrombin solution which is rich in calcium (See e.g., Spicer and Mikos, Journal of Controlled Release 2010. 148: 49-55; Kidd et al. Journal of Controlled Release 2012. 157:80-85; each of which is herein incorporated by reference in its entirety). The concentration of the components of the fibrin gel, hydrogel and/or glue can be altered to change the characteristics, the network mesh size, and/or the degradation characteristics of the gel, hydrogel and/or glue such as, but not limited to changing the release characteristics of the fibrin gel, hydrogel and/or glue. (See e.g., Spicer and Mikos, Journal of Controlled Release 2010. 148: 49-55; Kidd et al. Journal of Controlled Release 2012. 157:80-85; Catelas et al. Tissue Engineering 2008. 14:119-128; each of which is herein incorporated by reference in its entirety). This feature may be advantageous when used to deliver the polynucleotide disclosed herein. (See e.g., Kidd et al. Journal of Controlled Release 2012. 157:80-85; Catelas et al. Tissue Engineering 2008. 14:119-128; each of which is herein incorporated by reference in its entirety).

In some embodiments, a polynucleotide disclosed herein may include cations or anions. In one embodiment, the formulations include metal cations such as, but not limited to, Zn2+, Ca2+, Cu2+, Mg+ and combinations thereof. As a non-limiting example, formulations may include polymers and a polynucleotide complexed with a metal cation (See e.g., U.S. Pat. Nos. 6,265,389 and 6,555,525, each of which is herein incorporated by reference in its entirety).

In some embodiments, a polynucleotide may be formulated in nanoparticles and/or microparticles. These nanoparticles and/or microparticles may be molded into any size shape and chemistry. As an example, the nanoparticles and/or microparticles may be made using the PRINT® technology by LIQUIDA TECHNOLOGIES® (Morrisville, N.C.) (See e.g., International Pub. No. WO2007024323; herein incorporated by reference in its entirety).

In some embodiments, the polynucleotides disclosed herein may be formulated in NanoJackets and NanoLiposomes by Keystone Nano (State College, Pa.). NanoJackets are made of compounds that are naturally found in the body including calcium, phosphate and may also include a small amount of silicates. Nanojackets may range in size from 5 to 50 nm and may be used to deliver hydrophilic and hydrophobic compounds such as, but not limited to, polynucleotides, primary constructs and/or polynucleotide. NanoLiposomes are made of lipids such as, but not limited to, lipids which naturally occur in the body. NanoLiposomes may range in size from 60-80 nm and may be used to deliver hydrophilic and hydrophobic compounds such as, but not limited to, polynucleotides, primary constructs and/or polynucleotide. In one aspect, the polynucleotides disclosed herein are formulated in a NanoLiposome such as, but not limited to, Ceramide NanoLiposomes.

In one embodiment, the multidomain therapeutic protein is an anti-CD63 scFv-GAA fusion protein or an anti-ITGA7 scFv-GAA fusion protein. The administration of the anti-CD63 scFv-GAA fusion protein or the anti-ITGA7 scFv-GAA fusion protein via AAV-delivery provides long term stable production of GAA in the serum of the patient after administration of the multidomain therapeutic protein-harboring gene therapy vector. In one embodiment, the level of GAA in the serum of the recipient patient is ≥1.5 fold to 100 fold, ≥1.5 fold to 10 fold, ≥2.5 fold, 2.5 fold-3 fold, 2.5 fold, 2.6 fold, 2.7 fold, 2.8 fold, 2.9 fold, 3.0 fold, 3.1 fold, 3.2 fold, 3.3 fold, 3.4 fold, 3.5 fold, 3.6 fold, 3.7 fold, 3.8 fold, 3.9 fold, 4 fold, 5 fold, 6 fold, 7 fold, 8 fold, 9 fold, or 10 fold greater than the serum levels of a patient receiving GAA not linked to a delivery domain after 1 month, 3 months, 4 months, 5 months, or 6 months after administration of the multidomain therapeutic protein-harboring gene therapy vector.

In one embodiment, the administration of the anti-CD63 scFv-GAA fusion protein or the anti-ITGA7 scFv-GAA fusion protein via AAV-delivery provides long term stable reduction in stored glycogen levels in patients with Pompe disease. In one embodiment, the glycogen levels in heart, skeletal muscle, and liver tissue in the patient are reduced to wildtype (non-disease) levels. In one embodiment, the glycogen levels in heart, skeletal muscle, and liver tissue in the patient are maintained at wildtype levels 1 month, 2 months, 3 months, 4 months, 5 months, or 6 months after administration of the multidomain therapeutic protein-harboring gene therapy vector.

In one embodiment, the administration of the anti-CD63 scFv-GAA fusion protein or the anti-ITGA7 scFv-GAA fusion protein via AAV-delivery provides long term restoration of muscle strength in patients with Pompe disease. In one embodiment, the strength of the patient as measured by grip strength is restored to normal (i.e., non-disease normal levels) 1 month, 2 months, 3 months, 4 months, 5 months, or 6 months after administration of the multidomain therapeutic protein-harboring gene therapy vector.

In another aspect, the invention provides a composition comprising an enzyme activity and an antigen-binding protein, wherein the enzyme is associated with an enzyme-deficiency disease (LSD) and internalizing effector-binding protein. Enzymes (which include proteins that are not per se catalytic) associated with lysosomal storage diseases include for example any and all hydrolases, α-galactosidase, β-galactosidase, α-glucosidase, β-glucosidase, saposin-C activator, ceramidase, sphingomyelinase, β-hexosaminidase, GM2 activator, GM3 synthase, arylsulfatase, sphingolipid activator, α-iduronidase, iduronidase-2-sulfatase, heparin N-sulfatase, N-acetyl-α-glucosaminidase, α-glucosamide N-acetyltransferase, N-acetylglucosamine-6-sulfatase, N-acetylgalactosamine-6-sulfate sulfatase, N-acetylgalactosamine-4-sulfatase, δ-glucuronidase, hyaluronidase, and the like.

Internalizing effector-binding proteins for example include a receptor-fusion molecule, a trap molecule, a receptor-Fc fusion molecule, an antibody, an Fab fragment, an F(ab')2 fragment, an Fd fragment, an Fv fragment, a single-chain Fv (scFv) molecule, a dAb fragment, an isolated complementarity determining region (CDR), a CDR3 peptide, a constrained FR3-CDR3-FR4 peptide, a domain-specific antibody, a single domain antibody, a domain-deleted antibody, a chimeric antibody, a CDR-grafted antibody, a diabody, a triabody, a tetrabody, a minibody, a nanobody, a monovalent nanobody, a bivalent nanobody, a small modular immunopharmaceutical (SMIP), a camelid antibody (VHH heavy chain homodimeric antibody), a shark variable IgNAR domain, other antigen-binding proteins, and the like.

Internalizing effectors include for example CD63, MHC-I, Kremen-1, Kremen-2, LRP5, LRP6, LRP8, transferrin receptor, LDL-receptor, LDL-related protein 1 receptor, ASGR1, ASGR2, amyloid precursor protein-like protein-2 (APLP2), apelin receptor (APLNR), PRLR (prolactin receptor), MAL (Myelin And Lymphocyte protein, a.k.a. VIP17), IGF2R, vacuolar-type H+ ATPase, diphtheria toxin receptor, folate receptor, glutamate receptors, glutathione receptor, leptin receptor, scavenger receptor, SCARA1-5, SCARB1-3, and CD36. In certain embodiments, the internalizing effector is a kidney specific internalizer, such as CDH16 (Cadheri-16), CLDN16 (Claudn-16), KL (Klotho), PTH1R (parathyroid hormone receptor), SLC22A13 (Solute carrier family 22 member 13), SLC5A2 (Sodium/glucose cotransporter 2), and UMOD (Uromodulin). In other certain embodiments, the internalizing effector is a muscle specific internalizer, such as BMPR1A (Bone morphogenetic protein receptor 1A), m-cadherin, CD9, MuSK (muscle-specific kinase), LGR4/GPR48 (G protein-coupled receptor 48), cholinergic receptor (nicotinic) alpha 1, CDH15 (Cadheri-15), ITGA7 (Integrin alpha-7), CACNG1 (L-type calcium channel subunit gamma-1), CACNAIS (L-type calcium channel subunit alpha-15), CACNG6 (L-type calcium channel subunit gamma-6), SCN1B (Sodium channel subunit beta-1), CHRNA1 (ACh receptor subunit alpha), CHRND (ACh receptor subunit delta), LRRC14B (Leucine-rich repeat-containing protein 14B), dystroglycan (DAG1), and POPDC3 (Popeye domain-containing protein 3). In some specific embodiments, the internalizing effector is ITGA7, CD9, CD63, ALPL2, ASGR1, ASGR2 or PRLR.

In some embodiments, the enzyme is covalently linked (i.e., electrons shared across atoms) to the antigen-binding protein. In one particular embodiment, the internalizing effector-binding protein consists of or contains a half-body; the enzyme is fused to an Fc-fusion domain (e.g., at the C-terminus); and the Fc-domain that is covalently linked to the enzyme associates with the Fc-domain of the antigen-binding protein, such that the association contains one or more disulfide bridges. This particular embodiment is schematically depicted in FIG. 1A, panel B.

In another particular embodiment, the internalizing effector-binding protein (delivery domain) consists of or contains an antibody or an antibody fragment, and the enzyme is covalently linked to the antibody or antibody fragment. In a specific embodiment, the delivery domain is an antibody, and the enzyme is covalently linked (directly through a peptide bond, or indirectly via a linker) to the C-terminus of the heavy chain or the light chain of the antibody (FIG. 1A, panels C or E, respectively). In another specific embodiment, the delivery domain is an antibody, and the enzyme is covalently linked (directly through a peptide bond, or indirectly via a linker) to the N-terminus of the heavy chain or the light chain of the antibody (FIG. 1A, panels D or F, respectively).

In some embodiments, the enzyme and delivery domain are not covalently linked, but are combined in an admixture. The delivery domain and the enzyme can associate through non-covalent forces to form a complex. For example, in one particular embodiment, the delivery domain is a bispecific antibody in which one arm of the antibody binds the internalizing effector and the other arm binds the enzyme. This embodiment is schematically depicted in FIG. 1A, panel A.

In some embodiments, the enzyme is GAA or comprises GAA activity (e.g., an isozyme with GAA activity), and the internalizing effector is ITGA7, CDH15, CD9, CD63, APLP2, ASGR1, ASGR2 or PRLR. In a particular embodiment, the enzyme is GAA or comprises GAA activity, the internalization domain is CD63, and the delivery domain is a bispecific antibody with specificity for CD63 and GAA. In a particular embodiment, the enzyme is GAA or comprises GAA activity, the internalization domain is ITGA7, and the delivery domain is a bispecific antibody with specificity for ITGA7 and GAA.

In some embodiments, the enzyme is GLA or comprises GLA activity (e.g., an isozyme with GAA activity), and the internalizing effector is ITGA7, CD9, CD63, APLP2, ASGR1, ASGR2, or PRLR. In a particular embodiment, the enzyme is GLA or comprises GLA activity, the internalization domain is CD63, and the delivery domain is a bispecific antibody with specificity for CD63 and GLA. In a particular embodiment, the enzyme is GLA or comprises GLA activity, the internalization domain is ITGA7, and the delivery domain is a bispecific antibody with specificity for ITGA7 and GLA.

Pharmaceutical Compositions and Administration Thereof

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21.sup.st Edition, A. R. Gennaro (Lippincott, Williams & Wilkins, Baltimore, Md., 2006; incorporated herein by reference in its entirety) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical compositions.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, etc., and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and VEEGUM® [magnesium aluminum silicate]), long chain amino acid derivatives, high molecular weight alcohols (e.g. stearyl alcohol, cetyl alcohol, olelyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWEEN® 20], polyoxyethylene sorbitan [TWEEN® 60], polyoxyethylene sorbitan monooleate [TWEEN® 80], sorbitan monopalmitate [SPAN® 40], sorbitan monostearate [SPAN® 60], sorbitan tristearate [SPAN® 65], glyceryl monooleate, sorbitan monooleate [SPAN® 80]), polyoxyethylene esters (e.g. polyoxyethylene monostearate [MYRJ® 45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers, (e.g. polyoxyethylene lauryl ether [BRIJ® 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLUORINC® F 68, POLOXAMER® 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol,); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfate, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL® 115, GERMABEN® II, NEOLONE™, KATHON™, and/or EUXYL®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, chamomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof Excipients such as cocoa butter and suppository waxes, coloring agents, coating agents, sweetening, flavoring, and/ or perfuming agents can be present in the composition, according to the judgment of the formulator.

Delivery

The present disclosure encompasses the delivery of the gene therapy vector (e.g., the polynucleotides) by any appropriate route taking into consideration likely advances in the sciences of drug delivery. Delivery may be naked or formulated.

Naked Delivery

The polynucleotides of the present invention may be delivered to a cell naked. As used herein in, "naked" refers to delivering polynucleotides free from agents which promote transfection. For example, the polynucleotides delivered to the cell may contain no modifications. The naked polynucleotides may be delivered to the cell using routes of administration known in the art and described herein.

Formulated Delivery

The polynucleotides may be formulated, using the methods described herein. The formulations may contain polynucleotides and may further include, but are not limited to, cell penetration agents, a pharmaceutically acceptable carrier, a delivery agent, a bioerodible or biocompatible polymer, a solvent, and a sustained-release delivery depot. The formulated polynucleotides mRNA may be delivered to the cell using routes of administration known in the art and described herein.

Administration

The polynucleotides of the present invention may be administered by any route which results in a therapeutically effective outcome. These include, but are not limited to enteral, gastroenteral, epidural, oral, transdermal, epidural (peridural), intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection, (into the base of the penis), intravaginal administration, intrauterine, extra-amniotic administration, transdermal (diffusion through the intact skin for systemic distribution), transmucosal (diffusion through a mucous membrane), insufflation (snorting), sublingual, sublabial, enema, eye drops (onto the conjunctiva), or in ear drops. In specific embodiments, compositions may be administered in a way which allows them to cross the blood-brain barrier, vascular barrier, or other epithelial barrier. Non-limiting routes of administration for the polynucleotides, primary constructs or mRNA of the present invention are described below.

Parenteral and Injectable Administration

Liquid dosage forms for parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as CREMOPHOR®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are prepared by entrapping the drug in liposomes or microemulsions which are compatible with body tissues.

Depot Administration

As described herein, in some embodiments, the composition is formulated in depots for extended release. Generally, a specific organ or tissue (a "target tissue") is targeted for administration.

In some aspects of the invention, the polynucleotides are spatially retained within or proximal to a target tissue. Provided are method of providing a composition to a target tissue of a mammalian subject by contacting the target tissue (which contains one or more target cells) with the composition under conditions such that the composition, in particular the nucleic acid component(s) of the composition, is substantially retained in the target tissue, meaning that at least 10, 20, 30, 40, 50, 60, 70, 80, 85, 90, 95, 96, 97, 98, 99, 99.9, 99.99 or greater than 99.99% of the composition is retained in the target tissue. Advantageously, retention is determined by measuring the amount of the nucleic acid present in the composition that enters one or more target cells. For example, at least 1, 5, 10, 20, 30, 40, 50, 60, 70, 80, 85, 90, 95, 96, 97, 98, 99, 99.9, 99.99 or greater than 99.99% of the nucleic acids administered to the subject are present intracellularly at a period of time following administration. For example, intramuscular injection to a mammalian subject is performed using an aqueous composition containing a polynucleotide and a transfection reagent, and retention of the composition is determined by measuring the amount of the ribonucleic acid present in the muscle cells.

Aspects of the invention are directed to methods of providing a composition to a target tissue of a mammalian subject, by contacting the target tissue (containing one or more target cells) with the composition under conditions such that the composition is substantially retained in the target tissue. The composition contains an effective amount of a polynucleotide such that the polypeptide of interest is produced in at least one target cell. The compositions generally contain a cell penetration agent, although "naked" nucleic acid (such as nucleic acids without a cell penetration agent or other agent) is also contemplated, and a pharmaceutically acceptable carrier.

In some circumstances, the amount of a protein produced by cells in a tissue is desirably increased. Preferably, this increase in protein production is spatially restricted to cells within the target tissue. Thus, provided are methods of increasing production of a protein of interest in a tissue of a mammalian subject. A composition is provided that contains polynucleotides characterized in that a unit quantity of composition has been determined to produce the polypeptide of interest in a substantial percentage of cells contained within a predetermined volume of the target tissue.

In some embodiments, the composition includes a plurality of different polynucleotides, where one or more than one of the polynucleotides encodes a polypeptide of interest. Optionally, the composition also contains a cell penetration agent to assist in the intracellular delivery of the composition. A determination is made of the dose of the composition required to produce the polypeptide of interest in a substantial percentage of cells contained within the predetermined volume of the target tissue (generally, without inducing significant production of the polypeptide of interest in tissue adjacent to the predetermined volume, or distally to the target tissue). Subsequent to this determination, the determined dose is introduced directly into the tissue of the mammalian subject.

In one embodiment, the invention provides for the polynucleotides to be delivered in more than one injection or by split dose injections.

In one embodiment, the invention may be retained near target tissue using a small disposable drug reservoir, patch pump or osmotic pump. Non-limiting examples of patch pumps include those manufactured and/or sold by BD® (Franklin Lakes, N.J.), Insulet Corporation (Bedford, Mass.), SteadyMed Therapeutics (San Francisco, Calif.), Medtronic (Minneapolis, Minn.) (e.g., MiniMed), UniLife (York, Pa.), Valeritas (Bridgewater, N.J.), and SpringLeaf Therapeutics (Boston, Mass.). A non-limiting example of an osmotic pump include those manufactured by DURECT® (Cupertino, Calif.) (e.g., DUROS® and ALZET®).

Dosing

The present invention provides methods comprising administering a gene therapy vector comprising polynucleotide encoding a multidomain therapeutic polypeptide, and optionally subsequently the multidomain therapeutic polypeptide to a subject in need thereof. In some embodiments, a method comprises administering a gene therapy vector comprising polynucleotide encoding a multidomain therapeutic polypeptide in a therapeutically effective amount to a patient in need thereof, wherein the therapeutically effective amount is sufficient to obviate the subsequent administration of the multidomain therapeutic polypeptide. Accordingly, in some embodiments, a method of treating a patient in need thereof lacking an enzyme, e.g., reducing glycogen levels and/or reducing CRIM to GAA in a patient with Pompe disease, comprises administering to the patient a gene therapy vector comprising a polynucleotide encoding a multidomain therapeutic protein comprising the replacement enzyme, e.g., an anti-CD63 scFv::GAA fusion protein, e.g., a multidomain therapeutic protein comprising the sequence set forth as SEQ ID NO:11, in a therapeutically effective amount, wherein the therapeutically effective amount negates the need for subsequent administration to the patient of the replacement enzyme, e.g., GAA or derivatives thereof. In some embodiments, a method of treating a patient lacking an enzyme and in need thereof, e.g., reducing glycogen levels and/or reducing CRIM to GAA in a patient with Pompe disease, comprises administering to the patient a gene therapy vector comprising a polynucleotide encoding a multidomain therapeutic protein comprising a replacement enzyme, e.g., an anti-CD63 scFv::GAA fusion protein, e.g., a multidomain therapeutic protein comprising the sequence set forth as SEQ ID NO:11, in a therapeutically effective amount, and further comprises administering to the patient a therapeutically effective amount of the replacement enzyme. Nucleic acids, proteins or complexes, or pharmaceutical, imaging, diagnostic, or prophylactic compositions thereof, may be administered to a subject using any amount and any route of administration effective for preventing, treating, diagnosing, or imaging a disease, disorder, and/or condition (e.g., a disease, disorder, and/or condition relating to working memory deficits).

The exact amount required will vary from subject to subject, depending on the species, age, and general condition of the subject, the severity of the disease, the particular composition, its mode of administration, its mode of activity, and the like.

The dose of AAV viral vectors, e.g., the units of dose in vector genomes/per kilogram of body weight (vg/kg), required to achieve a desired effect or "therapeutic effect" (e.g., a certain serum concentration of a replacement enzyme) will vary based on several factors including, but not limited to: the route of AAV administration, the level of expression required to achieve a therapeutic effect, the specific disease or disorder being treated, and the stability of the expression multidomain therapeutic protein. One of skill in the art can readily determine a AAV virion dose range to treat a subject having a particular disease or disorder based on the aforementioned factors, as well as other factors that are well known in the art, see, e.g., CDER "Guidance for Industry Estimating the Maximum Safe Starting Dose in Initial Clinical Trials for Therapeutics in Adult Healthy Volunteers," July 2005, incorporated herein in its entirety by reference. An effective amount of the AAV is generally in the range of from about 10 µl to about 100 ml of solution containing from about $10^9$ to $10^{16}$ genome copies per subject. Other volumes of solution may be used. The volume used will typically depend, among other things, on the size of the subject, the dose of the AAV, and the route of administration. In some embodiments, a dosage between about $10^{10}$ to $10^{12}$ AAV viral genome per subject is appropriate. In some embodiments the AAV is administered at a dose of $10^{10}$, $10^{11}$, $10^{12}$, $10^{13}$, $10^{14}$, or $10^{15}$ genome copies per subject. In some embodiments the AAV is administered at a dose of $10^{10}$, $10^{11}$, $10^{12}$, $10^{13}$, or $10^{14}$ viral genomes per kg. In some embodiments, at least $2\times10^{12}$ viral genomes per kilogram (vg/kg) is administered. In some embodiments, the dose administered provides a threshold multidomain therapeutic protein serum level. In some embodiments the threshold therapeutic protein serum level is at least 1 µg/mL. In some embodiments, the dose administered provides a multidomain therapeutic protein serum level of greater than 2 µg/mL. In some embodiments, the dose administered provides a multidomain therapeutic protein serum level of greater than 3 µg/mL. In some embodiments, the dose administered provides a multidomain therapeutic protein serum level of greater than 4 µg/mL. In some embodiments, the dose administered provides a multidomain therapeutic protein serum level of greater than 5 µg/mL. In some embodiments, the dose administered provides a multidomain therapeutic protein serum level of greater than 6 µg/mL. In some embodiments, the dose administered provides a multidomain therapeutic protein serum level of greater than 7 µg/mL. In some embodiments, the dose administered provides a multidomain therapeutic protein serum level of greater than 8 µg/mL. In some embodiments, the dose administered provides a multidomain therapeutic protein serum level of greater than 9 µg/mL. In some embodiments, the dose administered provides a multidomain therapeutic protein serum level of greater than 10 µg/mL. In some embodiments, the dose administered provides a multidomain therapeutic protein serum level of greater than 11 µg/mL. In some embodiments, the dose administered provides a multidomain therapeutic protein serum level of greater than 12 µg/mL. In some embodiments, the dose administered provides a multidomain therapeutic protein serum level of greater than 13 µg/mL. In some embodiments, the dose administered provides a multidomain therapeutic protein serum level of greater than 14 µg/mL. In some embodiments, the dose administered provides a multidomain therapeutic protein serum level of greater than 15 µg/mL.

Compositions in accordance with the invention are typically formulated in dosage unit form for ease of administration and uniformity of dosage. It will be understood, however, that the total daily usage of the compositions of the present invention may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Nonlimiting and exemplary embodiments are listed below.

Embodiment 1. A method of delivering a therapeutic protein to the central nervous system (CNS) of a subject, comprising administering to the subject a nucleotide composition encoding a multidomain therapeutic protein via a liver-targeted delivery method sufficient to provide a therapeutically effective amount of the multidomain therapeutic protein in the CNS, wherein the multidomain therapeutic protein comprises a delivery domain and an enzyme domain.

Embodiment 2. The method of embodiment 1, wherein the delivery domain is an antibody or antigen-binding fragment thereof that binds specifically to an internalizing effector.

Embodiment 3. The method of embodiment 1 or embodiment 2, wherein the therapeutic protein is a lysosomal enzyme.

Embodiment 4. The method of embodiment 3, wherein the lysosomal enzyme is GAA.

Embodiment 5. The method of any one of embodiments 1-4, wherein the nucleotide composition is administered via a viral vector, optionally wherein the nucleotide composition is administered at a dose of at least $2 \times 10^{12}$ viral genomes per kilogram (vg/kg).

Embodiment 6. The method of embodiment 5, wherein the viral vector is an AAV vector.

Embodiment 7. The method of any one of embodiments 1-6, wherein the internalizing effector is expressed on the surface of cells selected from the group consisting of: cells in the CNS, epithelial cells, and cells that cross the blood brain barrier.

Embodiment 8. The method of any one of embodiments 1-7, wherein the delivery domain binds an internalizing effector
  (i) selected from the group consisting of CD63, Integrin alpha-7 (ITGA7), Kremen-1, Kremen-2, LRP5, LRP6, LRP8, transferrin receptor, LDL-receptor, LDL-related protein 1 receptor, ASGR1, ASGR2, amyloid precursor protein-like protein-2 (APLP2), apelin receptor (APLNR), myelin and lymphocyte protein (MAL), IGF2R, vacuolar-type H+ ATPase, diphtheria toxin receptor, folate receptor, glutamate receptors, glutathione receptor, leptin receptors, scavenger receptor A1-5 (SCARA1-5), SCARB1-3, and CD36;
  (ii) expressed in several tissue types, optionally selected from the group consisting of CD63, MHC-I, vacuolar-type H+ ATPase, IGF2R, Integrin alpha-7 (ITGA7), LRP5, LRP6, LRP8, Kremen-2, LDL-receptor, LDL-related protein 1 receptor, amyloid precursor protein-like protein-2 (APLP2), apelin receptor (APLNR), PRLR, MAL (myelin and lymphocyte protein (MAL), diphtheria toxin receptors, HBEGF (heparin binding EGF like growth factor), glutathione receptors, glutamate receptors, leptin receptors, and folate receptors,
  optionally wherein the subject exhibits one or more symptoms of a disease selected from the group consisting of Fabry disease, Gaucher disease, MPS I, MPS II, MPS IIIA, MPS IIIB, MPS IIID, MPS IVB, MPS VI, MPS VII, MPS IX, Pompe disease, Lysosomal acid lipase deficiency, Metachromatic leukodystrophy, Niemann-Pick diseases types A, B, and C2, Alpha mannosidosis, Neuraminidase deficiency, Sialidosis, Aspartylglycosaminuria, Combined saposin deficiency, Atypical Gaucher disease, Farber lipogranulomatosis, Fucosidosis, and Beta mannosidosis;
  (iii) preferentially expressed by bone and/or cartilage, optionally selected from the group consisting of Collagen X, Integrin alpha 10 (ITGA10), Fibroblast growth factor receptor 3 (FGFR3), Fibroblast growth factor receptor isoform C (FGFR3C), Hyaluronan and proteoglycan link protein 1 (CRTL1), Aggrecan, Collagen II, and Kremen-1,
  optionally wherein the subject exhibits one or more symptoms of a disease selected from the group consisting of MPS I, MPS II, MPS IIIA, MPS IIIB, MPS IIID, MPS IVA, MPS IVB, MPS VI, MPS VII, MPS IX, Beta mannosidosis, Gaucher disease, atypical Gaucher disease, combined Saposin deficiency, Aspartylglycosaminuria, Farber lipogranulomatosis, Sialidosis, Neuraminidase deficiency, and Alpha mannosidosis;

(iv) preferentially expressed by monocytes, macrophages, or microglia, optionally selected from the group consisting of scavenger receptor A1-5 (SCARA1-5), SCARB1-3, CD36, MSR1 (macrophage scavenger receptor 1), MRC1 (macrophage mannose receptor 1), VSIG4 (V-set and immunoglobulin domain-containing protein 4), CD68 (Macrosialin), and CSF1R (Macrophage colony-stimulating factor 1 receptor), optionally wherein the subject exhibits one or more symptoms of a disease selected from the group consisting of lysosomal acid lipase deficiency, Gaucher disease, Atypical Gaucher disease, combined Saposin deficiency, and Farber lipogranulomatosis;

(v) preferentially expressed by kidney cells, optionally selected from the group consisting of CDH16 (Cadheri-16), CLDN16 (Claudn-16), KL (Klotho), PTH1R (parathyroid hormone receptor), SLC22A13 (Solute carrier family 22 member 13), SLC5A2 (Sodium/glucose cotransporter 2), and UMOD (Uromodulin), optionally wherein the subject exhibits one or more symptoms or is diagnosed with a disease selected from the group consisting of Fabry disease, Alport syndrome, polycystic kidney disease, and Thrombotic Thrombocytopenic Purpura;

(vi) preferentially expressed by liver cells, optionally ASGR1 or ASGR2, optionally wherein the subject exhibits one or more symptoms or is diagnosed with a disease selected from the group consisting of as lysosomal acid lipase deficiency, Gaucher disease, MPS VI, MPS VII, MPS II, Niemann-Pick diseases types A, B, and C2, Sialidosis, Neuraminidase deficiency, atypical Gaucher disease, combined Saposin deficiency, Farber lipogranulomatosis;

(vii) preferentially expressed by muscle cells, optionally selected from the group consisting of BMPR1A (Bone morphogenetic protein receptor 1A), m-cadherin, CD9, MuSK (muscle-specific kinase), LGR4/GPR48 (G protein-coupled receptor 48), cholinergic receptor (nicotinic) alpha 1, CDH15 (Cadheri-15), ITGA7 (Integrin alpha-7), CACNG1 (L-type calcium channel subunit gamma-1), CACNA1S (L-type calcium channel subunit alpha-15), CACNG6 (L-type calcium channel subunit gamma-6), SCN1B (Sodium channel subunit beta-1), CHRNA1 (ACh receptor subunit alpha), CHRND (ACh receptor subunit delta), LRRC14B (Leucine-rich repeat-containing protein 14B), dystroglycan (DAG1), and POPDC3 (Popeye domain-containing protein 3), optionally wherein the subject exhibits one or more symptoms or is diagnosed with Pompe disease;

(viii) selected from the group consisting of ITGA7, CD9, CD63, ALPL2, MSR1, ASGR1, ASGR2, or PRLR; or (ix) that is CD63.

Embodiment 9. The method of any one of embodiments 1-8, wherein the delivery domain is a single-chain variable fragment (scFv).

Embodiment 10. The method of any one of embodiments 1-9, wherein the cell surface receptor (CSR)-binding protein (CSR-BP) comprises an amino acid sequence of SEQ ID NO:2.

Embodiment 11. The method of any one of embodiments 1-10, wherein the therapeutic protein comprises a hydrolase.

Embodiment 12. The method of any one of embodiments 1-11, wherein the therapeutic protein comprises a glycosylase.

Embodiment 13. The method of any one of embodiments 1-12, wherein the therapeutic protein comprises a glycosidase.

Embodiment 14. The method of any one of embodiments 1-13, wherein the therapeutic protein comprises an alpha-glucosidase.

Embodiment 15. The method of any one of embodiments 1-14, wherein the therapeutic protein comprises an amino acid sequence of SEQ ID NO:1 or SEQ ID NO:13, or a fragment thereof.

Embodiment 16. The method of any one of embodiments 1-15, wherein the therapeutic protein comprises an anti-ABeta, or an anti-Tau antibody.

Embodiment 17. The method of any one of embodiments 1-16, wherein the polynucleotide comprises a nucleic acid sequence of SEQ ID NO:11.

Embodiment 18. The method of any one of embodiments 1-17, wherein the enzyme domain comprises an alpha-glucosidase, and wherein the glycogen levels in any CNS tissue in the subject is reduced for at least nine months post-treatment.

Embodiment 19. The method of any one of embodiments 1-18, wherein the subject has Pompe disease.

Embodiment 20. The method of any one of embodiments 1-19, wherein the administered nucleotide composition provides a multidomain therapeutic protein serum level of at least 1 µg/mL.

Embodiment 21. A multidomain therapeutic protein comprising one or more delivery domain(s) and an enzyme domain, wherein the one or more delivery domain(s) binds human transferrin receptor (hTfR).

Embodiment 22. The multidomain therapeutic protein of embodiment 21, further comprising a second delivery domain that binds to an internalizing effector.

Embodiment 23. The multidomain therapeutic protein of embodiment 22, wherein the second delivery domain binds to (i) an internalizing effector selected from the group consisting of CD63, Integrin alpha-7 (ITGA7), MHC-I, Kremen-1, Kremen-2, LRP5, LRP6, LRP8, transferrin receptor, LDL-receptor, LDL-related protein 1 receptor, ASGR1, ASGR2, amyloid precursor protein-like protein-2 (APLP2), apelin receptor (APLNR), myelin and lymphocyte protein (MAL), IGF2R, vacuolar-type H+ ATPase, diphtheria toxin receptor, folate receptor, glutamate receptors, glutathione receptor, leptin receptors, scavenger receptor A1-5 (SCARA1-5), SCARB1-3, and CD36;

(ii) an internalizing effector expressed in several tissue types, optionally selected from the group consisting of CD63, vacuolar-type H+ ATPase, IGF2R, Integrin alpha-7 (ITGA7), LRP5, LRP6, LRP8, Kremen-2, LDL-receptor, LDL-related protein 1 receptor, amyloid precursor protein-like protein-2 (APLP2), apelin receptor (APLNR), PRLR, MAL (myelin and lymphocyte protein (MAL), diphtheria toxin receptors, HBEGF (heparin binding EGF like growth factor), glutathione receptors, glutamate receptors, leptin receptors, and folate receptors;

(iii) an internalizing effector preferentially expressed by bone and/or cartilage, optionally selected from the group consisting of Collagen X, Integrin alpha 10 (ITGA10), Fibroblast growth factor receptor 3 (FGFR3), Fibroblast growth factor receptor isoform C (FGFR3C), Hyaluronan and proteoglycan link protein 1 (CRTL1), Aggrecan, Collagen II, and Kremen-1;

(iv) an internalizing effector preferentially expressed by monocytes, macrophages, or microglia, optionally selected from the group consisting of scavenger receptor A1-5 (SCARA1-5), SCARB1-3, CD36, MSR1 (macrophage scavenger receptor 1), MRC1 (macrophage mannose receptor 1), VSIG4 (V-set and immunoglobulin domain-containing protein 4), CD68 (Macrosialin), and CSF1R (Macrophage colony-stimulating factor 1 receptor);

(v) an internalizing effector preferentially expressed by kidney cells, optionally selected from the group consisting of CDH16 (Cadheri-16), CLDN16 (Claudn-16), KL (Klotho), PTH1R (parathyroid hormone receptor), SLC22A13 (Solute carrier family 22 member 13), SLC5A2 (Sodium/glucose cotransporter 2), and UMOD (Uromodulin). In other certain embodiments, the internalization effector is a muscle specific internalizer, such as BMPR1A (Bone morphogenetic protein receptor 1A), m-cadherin, CD9, MuSK (muscle-specific kinase), LGR4/GPR48 (G protein-coupled receptor 48), cholinergic receptor (nicotinic) alpha 1, CDH15 (Cadheri-15), ITGA7 (Integrin alpha-7), CACNG1 (L-type calcium channel subunit gamma-1), CACNA1S (L-type calcium channel subunit alpha-15), CACNG6 (L-type calcium channel subunit gamma-6), SCN1B (Sodium channel subunit beta-1), CHRNA1 (ACh receptor subunit alpha), CHRND (ACh receptor subunit delta), LRRC14B (Leucine-rich repeat-containing protein 14B), dystroglycan (DAG1), and POPDC3 (Popeye domain-containing protein 3);

(vi) an internalizing effector preferentially expressed by liver cells, optionally ASGR1 or ASGR2;

(vii) an internalizing effector preferentially expressed by muscle cells, optionally selected from the group consisting of BMPR1A (Bone morphogenetic protein receptor 1A), m-cadherin, CD9, MuSK (muscle-specific kinase), LGR4/GPR48 (G protein-coupled receptor 48), cholinergic receptor (nicotinic) alpha 1, CDH15 (Cadheri-15), ITGA7 (Integrin alpha-7), CACNG1 (L-type calcium channel subunit gamma-1), CACNA1S (L-type calcium channel subunit alpha-15), CACNG6 (L-type calcium channel subunit gamma-6), SCN1B (Sodium channel subunit beta-1), CHRNA1 (ACh receptor subunit alpha), CHRND (ACh receptor subunit delta), LRRC14B (Leucine-rich repeat-containing protein 14B), dystroglycan (DAG1), and POPDC3 (Popeye domain-containing protein 3), or (viii) an internalizing effector protein selected from the group consisting of ITGA7, CD9, CD63, ALPL2, MSR1, ASGR1, ASGR2, or PRLR.

Embodiment 24. The multidomain therapeutic protein of any one of embodiments 21-23, wherein the second delivery domain binds to the internalizing effector CD63.

Embodiment 25. The multidomain therapeutic protein of any one of embodiments 21-24, wherein at least one of the one or more delivery domain(s) comprises an antigen-binding protein.

Embodiment 26. The multidomain therapeutic protein of embodiment 25, wherein each of the one or more delivery domain(s) comprises an antigen-binding protein.

Embodiment 27. The multidomain therapeutic protein of any one of embodiments 21-26, wherein at least one of the one or more delivery domain(s) comprises a single-chain variable fragment (scFv).

Embodiment 28. The multidomain therapeutic protein of any one of embodiments 21-27, wherein at least one of the one or more delivery domain(s) comprises a half-body.

Embodiment 29. The multidomain therapeutic protein of embodiment 28, wherein the delivery domain that binds hTfR is an scFv, wherein the half-body binds CD63, wherein the enzyme domain is GAA, and wherein GAA is conjugated to the carboxy terminus of the half-body that binds CD63.

Embodiment 30. The multidomain therapeutic protein of embodiment 27, wherein each of the one or more delivery domain(s) comprises an scFv.

Embodiment 31. The multidomain therapeutic protein of any one of embodiments 27-30, wherein at least one scFv is fused to an Fc.

Embodiment 32. The multidomain therapeutic protein of embodiment 31, wherein the Fc comprises a wildtype human IgG4 isotype, or derivative thereof.

Embodiment 33. The multidomain therapeutic protein of any one of embodiments 31-32, wherein GAA is conjugated to the carboxy terminus of the Fc.

Embodiment 34. The multidomain therapeutic protein of embodiment 30, comprising an anti-hTfR scFv, an anti-hCD63 scFv.

Embodiment 35. The multidomain therapeutic protein of embodiment 34, wherein the anti-hTfR scFv and anti-hCD63 scFv are both linked, at their carboxy termini, to a single GAA enzyme.

Embodiment 36. The multidomain therapeutic protein of any one of embodiments 21-27, wherein the delivery domain is an anti-hTfR scFv, and the enzyme domain is linked to carboxy terminus of the VL domain of the scFv.

Embodiment 37. The multidomain therapeutic protein of embodiment 36, further comprising a second delivery domain linked to the N-terminus of the VH domain of the anti-hTfR scFv.

Embodiment 38. The multidomain therapeutic protein of embodiment 37, wherein the second delivery domain is an anti-hCD63 scFV.

Embodiment 39. The multidomain therapeutic protein of any one of the preceding embodiments, wherein the enzyme domain comprises the amino acid sequence set forth as SEQ ID NO:1

Embodiment 40. A polynucleotide encoding the multidomain therapeutic protein of any one of embodiments 21-39 or embodiments 50-64.

Embodiment 41. The polynucleotide of embodiment 40, further comprising a virus nucleic acid sequence and a locus-targeting nucleic acid sequence.

Embodiment 42. The polynucleotide of embodiment 40 or embodiment 41, further comprising a virus nucleic acid sequence and a locus-targeting nucleic acid sequence, wherein the virus nucleic acid sequence is an adeno-associated virus (AAV) nucleic acid sequence.

Embodiment 43. The polynucleotide of any one of embodiments 40-42, further comprising a virus nucleic acid sequence and a locus-targeting nucleic acid sequence, wherein the virus nucleic acid sequence is an adeno-associated virus (AAV) nucleic acid sequence, and wherein the AAV nucleic acid sequence comprises an internal terminal repeat sequence, and optionally, a tissue specific regulatory element such as a liver specific promoter or a neuronal specific promoter.

Embodiment 44. The polynucleotide of any one of embodiments 40-43, further comprising a virus nucleic acid sequence and a locus-targeting nucleic acid sequence, wherein the virus nucleic acid sequence is an adeno-associated virus (AAV) nucleic acid sequence comprising an internal terminal repeat sequence that comprises SEQ ID NO:6, SEQ ID NO:7, or both, and optionally, a tissue specific regulatory element such as a liver specific promoter or a neuronal specific promoter.

Embodiment 45. The polynucleotide of any one of embodiments 40-44 further comprising a tissue specific regulatory element comprising the sequence set forth as SEQ ID NO:8 and/or SEQ ID NO:9.

Embodiment 46. A gene therapy vector comprising a polynucleotide of any one of embodiments 40-45.

Embodiment 47. The gene therapy vector of embodiment 46, wherein the gene therapy vector is selected from the group consisting of
a viral vector, optionally wherein the viral vector is a natural virus, an engineered virus, or a chimeric virus,
a naked polynucleotide comprising the polynucleotide of any one of embodiments 20-25,
a polynucleotide complex, optionally wherein the polynucleotide complex is a lipid nanoparticle comprising the polynucleotide of any one of embodiments 20-25 and lipids, and
any combination thereof.

Embodiment 48. The gene therapy vector of embodiment 46 or embodiment 47, wherein the gene therapy vector is a viral vector selected from the group consisting of a retrovirus, adenovirus, herpes simplex virus, pox virus, vaccinia virus, lentivirus, or an adeno-associated virus.

Embodiment 49. The gene therapy vector of embodiment 47 or embodiment 48, wherein the gene therapy vector is AAV9, Anc80, an AAV2/8 chimera and/or an AAV pseudotyped to a specific tissue, e.g., the liver or neuronal tissue.

Embodiment 50. A multidomain therapeutic protein comprising at least two delivery domains and at least one enzyme domain, wherein each of the two delivery domains is independently selected from the group consisting of an antibody, a half-body, and an scFv, and wherein at least one or more of the delivery domains is associated the at least one enzyme domain, preferably wherein the one or more delivery domains is covalently linked to the at least one enzyme domain.

Embodiment 51. The multidomain therapeutic protein of embodiment 50, comprising no more than two delivery domains.

Embodiment 52. The multidomain therapeutic protein of embodiment 50 or embodiment 51, wherein only one of the delivery domains is associated with the at least one enzyme domain.

Embodiment 53. The multidomain therapeutic protein of any one of embodiments 50-52, wherein each of the at least two delivery domains is covalently linked to an enzyme domain.

Embodiment 54. The multidomain therapeutic protein of embodiment 53, wherein each of the at least two delivery domains is covalently linked to the same enzyme domain.

Embodiment 55. The multidomain therapeutic protein of embodiment 53, wherein each of the at least two delivery domains is covalently linked to a different enzyme domain.

Embodiment 56. The multidomain therapeutic protein of any one of embodiments 50-55, wherein the multidomain therapeutic protein comprises no more than two delivery domains, wherein the first delivery domain comprises a half-body, and wherein the second delivery domain comprises an scFv.

Embodiment 57. The multidomain therapeutic protein of embodiment 56, wherein the scFv is fused to an Fc.

Embodiment 58. The multidomain therapeutic protein of embodiment 56 or embodiment 57, wherein the half-body is covalently linked at its carboxy terminus to a first enzyme domain and/or wherein the scFv is covalently linked at its carboxy terminus to an Fc, and optionally, a second enzyme domain.

Embodiment 59. The multidomain therapeutic protein of any one of embodiments 50-55, wherein the multidomain therapeutic protein comprises no more than two delivery domains, wherein the first and second delivery domains each comprise an scFv.

Embodiment 60. The multidomain therapeutic protein of embodiment 59, wherein both the first and second scFv are covalently linked to an enzyme domain.

Embodiment 61. The multidomain therapeutic protein of embodiment 59, comprising from N-terminus to C-terminus: the first scFv, the second scFv, and the enzyme domain.

Embodiment 62. The multidomain therapeutic protein of any one of embodiments 50-61, wherein at least one delivery domain binds a lysosomal trafficking molecule and at least one delivery domain binds a transcytosis effector.

Embodiment 63. The multidomain therapeutic protein of embodiment 62, wherein the lysosomal trafficking molecule is selected from the group consisting of CD63, ITGA7, CD9, CD63, CD81, CD82, or CD151, and wherein the transcytosis effector is selected from the group consisting of an LDL receptor, an IgA receptor, a transferrin receptor, a neonatal Fc receptor, insulin receptor, CD98, and Basigin.

Embodiment 64. The multidomain therapeutic protein of any one of embodiments 50-63, comprising a structure as depicted in FIG. 1C, FIG. 1D, FIG. 1E, or FIG. 1F.

Embodiment 65. Use of a nucleotide that encodes the multidomain therapeutic protein of any one of embodiments 21-39 and 50-64, the polynucleotide of any one of embodiments 40-45, or the gene therapy vector of any one of embodiments 46-49 in the method of any one of embodiments 1-20.

The following examples are provided to further illustrate the methods of the present invention. These examples are illustrative only and are not intended to limit the scope of the invention in any way.

EXAMPLES

Example 1: Construction of Anti-hCD63 ScFv::GAA Polynucleotide and Gene Therapy Vector AAV2/8 viruses encoding for the expression of human GAA (hGAA; SEQ ID NO: 1; nucleic acid sequence represented by SEQ ID NO:12) or an anti-human CD63 single chain variable fragment (ScFv) fused on its C-terminus to human GAA (anti-hCD63 ScFv-hGAA; SEQ ID NO: 10; nucleic acid represented by SEQ ID NO:11) were generated using a standard triple transfection protocol (Gray et al. 2011; see also "Production of recombinant adeno-associated viral vectors and use in vitro and in vivo administration", Current Protocols in Neuroscience, John Wiley & Sons, New York (1999), pp. 4.17.1-4.17.25, Vol 1). For the production, $1 \times 10^7$ HEK293 cells were plated onto 15 cm plates. The following day the cells were transfected with (A) either 8 µg of a control pAAV vector comprising a liver specific serpina 1 enhancer (SEQ ID NO:9) and encoding TTR driven human GAA or test pAAV comprising a liver specific serpina 1 enhancer (SEQ ID NO:9) and encoding a TTR driven hCD63 ScFv-hGAA (see FIG. 1B) and (B) pAAV RC2/8-derived vector (Gao, 2002) and 16 µg of pHelper (Agilent, Cat #240074) using PEIpro (Polyplus transfection, New York, N.Y. catalog #115-100)-mediated transfection at ratio of 1:1 (1 ul PEIpro:1 µg DNA). Seventy-two hours after transfection, the cells were collected and lysed in a buffer comprised of 20 mM Tris-HCl, 1 mM MgCl2, 2.5 mM KCl, 100 mM NaCl using a standard freeze-thaw method. Next, benzonase (Sigma, Cat #E1014-25KU) was added to the samples at a final concentration of 0.5 U/µL, and this was then incubated at 37° C. for 60 minutes. Viruses were then purified using iodixanol gradient ultracentrifugation as described in (Zolotukhin et al., 1999, Gene Ther 1999; 6:973-985) and were subsequently titrated by qPCR.

AAV samples were treated with DNaseI (Thermofisher Scientific, Cat #EN0525) at 37° C. for one hour and lysed using DNA extract All Reagents (Thermofisher Scientific Cat #4403319). Encapsidated viral genomes were quantified using an QuantStudio 3 Real-Time PCR System (Thermofisher Scientific) using primers directed to the AAV2 ITRs. The sequences of the AAV2 ITRs primers are 5'-GGAACCCCTAGTGATGGAGTT-3' (fwd ITR; SEQ ID NO:3) and 5'-CGGCCTCAGTGAGCGA-3' (rev ITR; SEQ ID NO:4) (Aurnhammer et al., 2012), derived the left internal inverted repeat (ITR) sequence from of the AAV (SEQ ID NO:6) and the right internal inverted repeat (ITR) sequence from of the AAV (SEQ ID NO:7), respectively. The sequence of the AAV2 ITRs probe is 5'-6-FAM-CACTCCCTCTCTGCGCGCTCG-TAMRA-3' (SEQ ID NO:5) (Aurnhammer C., Haase M., Muether N., et al., 2012, Hum. Gene Ther. Methods 23, 18-28). After a 95° C. activation step for 10 min, a two-step PCR cycle was performed at 95° C. for 15 seconds and 60° C. for 30 seconds for 40 cycles. The TaqMan Universal PCR Master Mix (Thermofisher Scientific, Cat #4304437) was used in the qPCR. DNA plasmid (Agilent, Cat #240074) was used as standard to determine absolute titers.

Anti-human CD63 antibodies and their fusions used the H5C6 mouse anti-human CD63 variable domains (amino acids 1-119 of SEQ ID NO:10 provide the amino acid sequence of the heavy chain variable domain ($V_H$) of the H5C6 antibody and amino acids 135-245 of SEQ ID NO:10 provide the amino acid sequence of the light chain variable domain ($V_L$) of the H5C6 antibody). The anti-hCD63 ScFv used here (SEQ ID NO:2) was derived from the H5C6 clone, which is mouse-anti-hCD63 monoclonal IgG1, kappa light chain antibody (H5C6 was deposited to the Developmental Studies Hybridoma Bank at the University of Iowa by August, J. T./Hildreth, J. E. K. (DSHB Hybridoma Product H5C6; DSHB Cat #h5c6, RRID:AB 528158). ScFv versions of the antibodies were cloned with variable domains in heavy-light order with a glycine-serine linker in between (5'-VH-Gly-Ser-VL-3')

Example 2: Glycogen Content in Murine Pompe Model Post-AAV

To determine the effect of AAV delivered anti-hCD63 ScFv-GAA fusion versus AAV delivered GAA, in a relevant glycogen storage in vivo model, both therapies were delivered to a Pompe disease mouse model where mice were homozygous for the deletion of the mouse GAA gene and were homozygous for the expression of human CD63 in place of mouse CD63 with a strain background of 75% C57BL/6; 25% 129SvJ. These mice are herein referred to as CD63 HumIn GAA KO mice or alternatively as CD63hu/hu; $GAA^{-/-}$ mice.

For the experiment, 2-month-old CD63 HumIn GAA KO mice were administered via tail vein injection with either AAV2/8 virus containing a genome with either the TTR liver specific promoter driving human GAA (AAV-hGAA; described in Example 1) or the TTR liver specific promoter driving anti-human CD63 ScFv fused at its C-terminus with human GAA (AAV-anti-hCD63 ScFv-hGAA; described in Example 1). Both AAV2/8 viruses were delivered at either one of two doses, 1e10 vg/mouse or 1e11 vg/mouse. As controls, untreated CD63 HumIn GAA KO mice and untreated CD63 HumIn with the mouse GAA gene intact were included in the assay. Mice were housed for 3 months after treatment and bled incrementally (monthly) during this period for serum measurements of GAA levels and anti-GAA antibodies. After 3 months, all mice were sacrificed and individual tissues were harvested for glycogen measurements, PAS-H staining, quantification of central nuclei, measurement of lysosomal proliferation, and measurement of LC3b expression. Experimental dosing and treatment protocol for groups of mice are shown in Table 3.

TABLE 3

Experimental dosing and treatment protocol for groups of mice

| Group | Mice | Number of Mice | Treatment | Dosage |
|---|---|---|---|---|
| 1 | CD63 HumIn GAA KO | 4 | None | N/A |
| 2 | CD63 HumIn GAA KO | 4 | AAV-hGAA | 1e10 vg/mouse |
| 3 | CD63 HumIn GAA KO | 4 | AAV-hGAA | 1e11 vg/mouse |
| 4 | CD63 HumIn GAA KO | 5 | AAV-anti-hCD63 ScFv-hGAA | 1e10 vg/mouse |
| 5 | CD63 HumIn GAA KO | 4 | AAV-anti-hCD63 ScFv-hGAA | 1e11 vg/mouse |
| 6 | CD63 HumIn GAA WT | 2 | None | N/A |

The results are also depicted in FIG. 2, which shows that anti-hCD63scFv::GAA brings glycogen down to wildtype levels in skeletal muscle, unlike GAA alone. Treatment with the two-domain anti-hCD63scFv::GAA multidomain therapeutic protein resulted in much greater reduction in stored glycogen compared to the single-domain GAA replacement enzyme. By plotting quadriceps glycogen levels (FIG. 3) or heart glycogen levels (FIG. 4) against the total serum expression of GAA or scfv-GAA over three months for individual mice, it was observed that the anti-hCD63scFv::GAA fusion protein removes more glycogen than the GAA enzyme alone, even at similar serum levels (FIGS. 3 and 4).

Example 3: Immunological Response to GAA

To measure anti-human GAA antibody serum levels, serum from all the treatment groups was separated from the blood collected during the terminal bleed using serum separator tubes (BD Biosciences, Cat #365967) as per the manufacturer's specifications. Separately, 96-well high protein binding plates (ThermoFisher, Cat #15041) were coated with 20 μg of hGAA (R&D Systems, Cat #8329-GH-025) diluted in PBS overnight. Plates were washed with PBS+ 0.05% Tween (PBS-T) 3 times. Plates were blocked with 0.5% BSA in PBS-T, and serial dilutions of mouse serum ranging from 1:300 to 1:5.1e7 were added to the plate overnight. Total anti-mouse IgG (subclasses 1+2a+2b+3) was measured using a HRP conjugated goat anti-mouse IgG antibody (Jackson Immuno Research, Cat #115-035-164) and the BD Opt EIA substrate kit. The colormetric reactions were stopped using 1 N phosphoric acid. Absorbance was then read at 450 nm on a Spectramax i3 plate reader (Molecular Devices). Dilution curves were fit to sigmoidal curves, and titers were calculated from the curves. The titers expressed as mean total IgG titer+/−SD are shown in Table 4.

As shown in Table 4, mice that did not receive treatment showed an average background titer with mean levels of 1.1E+03. Mice treated with the low dose of virus (1e10 vg/mouse) of either AAV-anti-hCD63 ScFv-hGAA or AAV-hGAA demonstrated high titers, whereas in mice treated with the high dose (1e11 vg/mouse), titers were lower. Mice treated with 1e11 vg of AAV-anti-hCD63 ScFv-hGAA that had the highest levels of GAA in serum had titers within the range of untreated mice.

TABLE 4

Serum anti-GAA antibody levels

|  | Total IgG anti-GAA titer CD63 HumIn GAA KO + no treatment | CD63 HumIn GAA KO + AAV-hGAA (1e10 vg) | CD63 HumIn GAA KO + AAV-hGAA (1e11 vg) | CD63 HumIn GAA KO + AAV-anti-hCD63 ScFv-hGAA (1e10 vg) | CD63 HumIn GAA KO + AAV-anti-hCD63 ScFv-hGAA (1e11 vg) |
|---|---|---|---|---|---|
| Mean | 1.1E+03 | 7.6E+06 | 2.4E+04 | 5.5E+04 | 4.0E+03 |
| SD | 1.3E+03 | 1.0E+07 | 2.5E+04 | 1.9E+04 | 4.9E+03 |

Higher levels of GAA or anti-hCD63scFv::GAA after AAV administration correspond with lower anti-GAA titers. The serum of GAA null mice treated with high or low titers of AAV-anti-hCD63scFv::GAA or AAV-GAA were assessed for anti-GAA antibodies over the course of the three months post-injection. FIG. 5 depicts serum anti-GAA antibody titers vs GAA exposure (i.e., the total serum expression over 3 months of GAA or scfv-GAA) for individual mice, which demonstrates a negative correlation between antibody titer and serum exposure to GAA, demonstrating that mice with high GAA exposure were tolerized to GAA. Likewise, FIG. 6, which plots anti-GAA antibody titers for various groups infected with AAV encoding GAA or an anti-hCD63scFv::GAA protein, demonstrates that higher doses of construct led to lower titers of anti-GAAs.

Example 4: Serum GAA

To measure human GAA serum levels over the course of the experiment, samples were collected at monthly time points via tail bleed. Serum was separated from the blood using serum separator tubes (BD Biosciences, Cat #365967) as per the manufacturer's specifications. 1 μL of isolated serum was then loaded onto a 4-20% Novex wedgewell pre-cast gel, run at 220V for 45 minutes and transferred to nitrocellulose membrane at 200 mA for 1 hour using standard procedures. The nitrocellulose membrane was then probed with an anti-GAA primary antibody (Abcam, #ab137068) used at a dilution of 1:2000 and an anti-GAPDH antibody (Abcam, #AB9484) used at a dilution of 1:1000 in 12 mL and incubated overnight at 4° C. After primary antibody incubation, the membrane was washed three times with 1×TBST for 5 minutes per wash. Anti-rabbit IgG (LiCor, 926-32211) and anti-mouse IgG (LiCor, 925-68070) (LiCor, Lincoln, Nebr.) secondary antibodies at a dilution of 1:15000 in 12 mL were then added to the membrane and incubated for 1 hour at room temperature. After secondary antibody incubation, the membrane was washed two times with 1×TBST for 5 minutes per wash and one time with 1×TBS for 5 minutes. The membrane was then imaged and quantified using a LiCor Odyssey instrument (LI-COR Biotechnology). Serum levels of GAA expressed as mean+/− standard deviation (SD) in arbitrary units are shown in Table 5.

As shown in Table 5, CD63 HumIn GAA KO mice treated with the high dose ($10^{11}$ vg/mouse) of AAV-anti-hCD63 ScFv-hGAA or AAV-hGAA tested demonstrated sustained levels of GAA in the serum over the course of the experiment, with serum levels of GAA somewhat higher in AAV-anti-hCD63 ScFv-hGAA treated mice than in the AAV-hGAA treated mice. In mice treated with the treated with the low dose ($10^{10}$ vg/mouse) of either AAV-anti-hCD63 ScFv-hGAA or AAV-hGAA, the levels of GAA dropped over the course of the experiment, approaching negligible levels in some mice by the 12 week time point.

TABLE 5

Serum GAA levels

| Week | AAV-anti-hCD63 ScFv-hGAA ($10^{10}$ vg) | | AAV-hGAA ($10^{10}$ vg) | | AAV-anti-hCD63 ScFv-hGAA ($10^{11}$ vg) | | AAV-hGAA ($10^{11}$ vg) | |
|---|---|---|---|---|---|---|---|---|
|  | Mean | SD | Mean | SD | Mean | SD | Mean | SD |
| 1 | 0.21 | 0.17 | 0.04 | 0.03 | 2.36 | 1.78 | 0.77 | 0.53 |
| 2 | 0.19 | 0.16 | 0.07 | 0.07 | 2.02 | 1.18 | 1.15 | 0.56 |
| 4 | 0.17 | 0.15 | 0.01 | 0.02 | 2.80 | 1.16 | 1.22 | 0.75 |
| 8 | 0.29 | 0.33 | 0.03 | 0.05 | 2.58 | 1.18 | 0.62 | 0.60 |
| 12 | 0.12 | 0.19 | 0.00 | 0.01 | 2.61 | 1.53 | 0.77 | 0.86 |
| Area under the curve | 2.27 | 2.23 | 0.27 | 0.36 | 28.13 | 13.73 | 9.80 | 7.22 |

Expression of GAA or anti-hCD63scfv::GAA was maintained over time in mice receiving the high dose of AAV ($10^{11}$ vg/mouse), but fell off in mice receiving the lower dose ($10^{10}$ vg/mouse). FIG. 7A depicts a graph plotting serum levels of GAA, as probed by western blot, over time for various groups infected with AAV encoding GAA or an anti-hCD63 scfv fusion to GAA. The fusion protein (scFv::GAA) demonstrated consistently higher levels (e.g., 2.5 to 3-fold) of serum GAA than the GAA enzyme without the delivery domain (FIG. 7A).

Real-time PCR quantifications of expression in liver, heart, and quadriceps lysates 3 months after injection are shown in FIG. 7B. Liver expression was detected for all injections of AAV construct, with highest levels for the 1e11 vg/mouse injections for both AAV-hGAA and AAV-anti-hCD63::hGAA (both driven by liver-specific promoter, LSP). A comparison of serum GAA level to RNA expression level of GAA was also made (FIG. 7C) and the results show that mice receiving the AAV encoding the fusion protein presented lower GAA RNA expression localized to the liver at 3 months however GAA serum levels were high in that particular mouse. AAV-LSP-hGAA injections did not present high serum levels of GAA when RNA levels were low in the liver. See FIG. 7C. This data suggests that the AAV encoding the fusion protein (and expression is driven by a liver-specific promoter) attains an improved secretion profile for GAA.

A higher secreted to intracellular ratio of antibody::hGAA versus hGAA alone in Huh-7 hepatocytes was also observed. In one experiment, Huh-7 human hepatocytes were transiently transfected with liver-specific promoter driven constructs encoding for hGAA, anti-hCD63 scFv::GAA fusion, or a non-binding scFv::GAA fusion control. Both scFv::GAA fusion constructs had a higher ratio of protein in the secreted supernatant than hGAA alone 3 days after transfection (statistically significant to p<0.05, n=3). Addition of M6P into the supernatant during the experimental period to mitigate CI-MPR-mediated uptake did not affect the ratio.

Example 5: Tissue Measurement of Glycogen and Histological Characterization of Muscle Tissue Tissue Measurements of Glycogen:

To measure the glycogen content in individual tissues, heart, quadriceps, gastrocnemius, diaphragm, soleus, and EDL tissue were dissected from mice from all groups immediately after $CO_2$ asphyxiation, and were then snap frozen in liquid nitrogen, and stored at −80° C.~50 mg of each tissue was lysed on a benchtop homogenizer with stainless steel beads in distilled water at a ratio of 1 mg to 25 µL water for glycogen measurements. Glycogen analysis lysates were heated at 105° for 15 minutes and centrifuged at 21000×g to clear debris. Glycogen measurements were performed using a Glycogen Assay Kit (Sigma-Aldrich, #MAK016) according to manufacturer's instructions for fluorometric assays. The fluorescence of each sample was measured at 535 nm excitation and 587 nm emission on a fluorescence plate reader (Molecular Devices, Spectramax i3). The calculated amount of glycogen was calculated using the following formula provided by the manufacturer. The calculated amount of glycogen from each tissue in each treatment group was then averaged and is expressed as mean+/−standard deviation (SD) in Table 6.

As shown in Table 6, loss of Gaa causes a large increase in mean glycogen levels across all tissues measured, as compared to GAA WT mice. Treatment with AAV-anti-hCD63 ScFv-hGAA at $10^{11}$ vg/mouse reduced glycogen to WT- or near-WT levels in all tissues tested, unlike treatment with AAV-GAA which only partially reduced stored glycogen. The low doses of either virus also reduced glycogen, but to a lesser extent that the high doses. The $10^{10}$ vg/mouse dose of AAV-anti-hCD63 ScFv-hGAA reduced glycogen levels in a similar manner as the $10^{11}$ vg/mouse dose of AAV-GAA.

TABLE 6

Mean +/− SD glycogen level measured in heart, quadriceps, gastrocnemius, diaphragm, soleus, and EDL

|  | no treatment | | AAV-hGAA ($10^{10}$ vg) | | AAV-hGAA ($10^{11}$ vg) | |
| --- | --- | --- | --- | --- | --- | --- |
|  | Mean | SD | Mean | SD | Mean | SD |
| Heart | 27.798 | 3.013 | 17.246 | 4.375 | 1.770 | 2.279 |
| Quadricep | 14.650 | 1.783 | 11.012 | 0.528 | 5.878 | 3.504 |
| Gastrocnemius | 14.295 | 0.480 | 10.990 | 0.868 | 6.073 | 3.080 |
| Diaphragm | 15.463 | 1.173 | 11.446 | 1.237 | 3.995 | 3.395 |
| Soleus | 17.260 | 2.262 | 13.684 | 2.506 | 6.533 | 5.201 |
| EDL | 13.588 | 0.498 | 11.178 | 1.760 | 6.275 | 3.159 |

|  | AAV-anti-hCD63 ScFv-hGAA ($10^{10}$ vg) | | AAV-anti-hCD63 ScFv-hGAA ($10^{11}$ vg) | | CD63 HumIn GAA WT mice (control) | |
| --- | --- | --- | --- | --- | --- | --- |
|  | Mean | SD | Mean | SD | Mean | SD |
| Heart | 2.190 | 2.678 | 0.058 | 0.010 | 0.085 | 0.007 |
| Quadricep | 4.485 | 3.147 | 0.798 | 0.251 | 0.440 | 0.042 |
| Gastrocnemius | 5.198 | 2.516 | 0.825 | 0.461 | 0.790 | 0.014 |
| Diaphragm | 3.083 | 2.968 | 0.388 | 0.121 | 0.385 | 0.007 |
| Soleus | 5.268 | 2.786 | 1.040 | 0.896 | 0.545 | 0.049 |
| EDL | 2.495 | 1.750 | 0.313 | 0.099 | 0.260 | 0.141 |

Quadricep Harvest for Histopathology and Quantification:

Quadricep tissue samples from mice from each group besides the low dose (1e10 vg/mouse) treatment group were either snap frozen immediately after dissection in liquid nitrogen and stored at −80° C. for quantification of LC3b expression or were placed onto blocks containing O.C.T medium (Tissue-Tek, #4583).

Tissues samples in O.C.T medium were sent to Histoserv, Inc. (Germantown, Md.) for sectioning and periodic acid Schiff (PAS) staining to detect polysaccharides. Additional sections were prepared and returned for staining of central nuclei and lysosomal proliferation.

Pas Staining:

PAS stain sections were imaged using a Leica slide scanner at 20× magnification. The resulting images from representative mice for each treatment group are shown in FIG. 8.

As shown in FIG. 8, CD63 HumIn GAA KO that were treated with AAV-anti-hCD63 ScFv-hGAA at 3 months demonstrated a marked decrease in staining as compared to both the CD63 HumIn GAA KO mice with no treatment and the CD63 HumIn GAA KO mice treated with AAV-hGAA, which displayed high levels of PAS staining. This further indicates that the treatment with AAV-anti-hCD63 ScFv-hGAA can reduce polysaccharides accumulation in CD63 HumIn GAA KO mice and can do so in a uniform manner across muscle fibers.

Quantification of Central Nuclei and Lysosomal Proliferation:

Unstained sections from Histoserv were removed from the freezer and then fixed with 4% paraformaldehyde in PBS for 15 minutes in a staining chamber. The fixed slides were then washed twice for 5 minutes in PBS and subsequently incubated with blocking buffer (eBiosciences, 00-4953-54) for 1 hour at room temperature. Slides were then either stained with either a rat anti-Lamp-1 antibody (Abcam, #AB25245) at a dilution of 1:50 in blocking buffer, a rabbit anti-Laminin antibody (Sigma, #L9393) at a dilution of 1:1000 in blocking buffer or blocking buffer with no added antibody while in a humidified staining chamber and then transferred to 4° C. for overnight incubation. The following day, slides were then washed twice for 5 minutes in PBS and subsequently stained with either goat anti-rabbit IgG (H+L) superclonal secondary antibody conjugated with Alexa Fluor 647 (Life Tech Thermo, #A27040) or goat anti-rat IgG (H+L) cross-adsorbed secondary antibody conjugated with Alexa Fluor 555 (Life Tech Thermo, #A21434) in a staining chamber then allowed to incubate for 1 hour at room temperature. Stained slides were then washed twice for 5 minutes in PBS before they were mounted with Fluoromount-G with DAPI (Life Tech Thermo, #00-4959-52) and imaged on a Zeiss LSM710 instrument (Carl Zeiss Microscopy GmbH). Number of centralized nuclei was quantified using Halo software (Indica Labs, NM) and is expressed as percentage of fibers showing central nuclei+/−standard deviation are shown in Table 7. Lysosomal proliferation is depicted in FIG. 8.

TABLE 7

Quantification of central nuclei

|  | no treatment | | AAV-hGAA (1e11 vg) | | AAV-anti-hCD63 ScFv-hGAA (1e11 vg) | | CD63 HumIn GAA WT mice (control) | |
| --- | --- | --- | --- | --- | --- | --- | --- | --- |
|  | Mean | SD | Mean | SD | Mean | SD | Mean | SD |
| % of Fiber with central nuclei | 22.00 | 10.10 | 33.00 | 4.36 | 12.75 | 6.29 | 8.50 | 7.78 |

Quantification of LC3b Expression:

For quantification of LC3b expression, snap frozen samples were thawed, homogenized and then lysed in RIPA buffer at a 1 mg tissue to 254 RIPA buffer ratio (150 mM NaCl, 1.0% IGEPAL® CA-630, 0.5% sodium deoxycholate, 0.1% SDS, 50 mM Tris, pH 8.0, Sigma Aldrich, R0278) by bead impaction for 45 seconds (MP Biomedical). Lysates were cleared of insoluble material by centrifugation at 21,000×g and then 300 µg of lysate in RIPA buffer was loaded on a 4-20% Novex wedgewell pre-cast gel, transferred to a nitrocellulose membrane and analyzed by western blot using a similar protocol as previously described for the analysis of serum GAA levels, substituting the use of primary antibody that recognizes mouse LC3b-I and LC3b-II (Sigma, #L7543) in place of the primary antibody against GAA. The membrane was then imaged and quantified using a LiCor Odyssey instrument (LI-COR Biotechnology). LC3b-I and LC3b-II levels expressed as (mean+/−standard deviation) in arbitrary units are shown in Table 8.

As shown in Table 8, there was a significant increase in both mean LC3b-I and LC3b-II levels in mice lacking GAA as compared to CD63 HumIn GAA WT mice. Treatment with AAV-anti-hCD63 ScFv-hGAA decreased mean LC3b-I and LC3b-II levels in CD63 HumIn GAA KO to the WT- or near-WT levels. CD63 HumIn GAA KO treated with AAV-hGAA demonstrated slightly decreased mean LC3b-I and LC3b-II levels as compared to CD63 HumIn GAA KO mice, but this decrease was not as pronounced as with AAV-anti-hCD63 ScFv-hGAA treatment.

TABLE 8

LC3b-I and LC3b-II levels in the quadriceps of mice

| treatment | un-treated | AAV-hGAA | AAV-anti-hCD63 ScFv-hGAA | CD63 HumIn GAA WT (control) |
| --- | --- | --- | --- | --- |
| LC3b-I levels (arbitrary units) | | | | |
| average | 833 | 628 | 403 | 282 |
| SD | 109 | 139 | 33 | 49 |
| LC3b-II levels (arbitrary units) | | | | |
| average | 3308 | 2888 | 445 | 369 |
| SD | 582 | 1282 | 398 | 33 |

Example 6: AAV Anti-hCD63::GAA Treatment Leads to Significant Gains in Tests of Muscle Strength and Coordination Grip strength and Rotarod test performance of mice treated (see above) with either AAV-LSP hGAA or AAV-LSP anti-hCD63::hGAA. Accelerating Rotarod measurements (FIG. 9A) and forelimb grip strength measurements (FIG. 9B) of wild-type GAA mice, untreated control, AAV-LSP-hGAA (1e11 vg/mouse) or AAV-LSP-anti-hCD63:: hGAA treatment (1e11 vg/mouse) were taken at monthly intervals for 6 months. Error bars are +/−SD. N=8-10 for all groups.

Example 7: Other Membrane Proteins as "Guides" Directing GAA to Tissues

Other membrane proteins were tested, such as anti-ITGA7 (Integrin alpha-7) fusion proteins, to guide GAA to tissues to replace GAA in enzyme-deficient mice. C2C12 mouse myoblasts were incubated overnight with anti-mCD63-GAA or anti-ITGA7-GAA with or without the presence of 5 mM M6P. Active GAA enzyme was detected in myoblast lysates over time for both fusion proteins (FIG. 10A). In further experiments, GAA KO mice humanized for CD63 (GAA−/−;CD63hu/hu) were given plasmids encoding an scFv::GAA format of anti-hCD63::GAA or a full-length IgG4::GAA format of anti-integrin alpha-7 by hydrodynamic delivery (HDD), and mice were sacrificed 3 weeks post-HDD. Tissue glycogen levels were measured in heart, quadriceps, gastrocnemius and diaphragm. Untreated control mice, GAA−/−×CD63hu/hu and untreated wild-type GAA control mice, GAA+/+;CD63hu/hu (4) were also tested under the same conditions. Glycogen levels were at very low levels in both anti-hCD63::GAA treated mice and anti-ITGA7::GAA treated mice groups, as in the wild-type mice. See FIG. 10B.

Example 8: At Comparable Serum Levels, AAV Anti-CD63::GAA Treatment is More Effective than AAV with Optimized GAA Construct CD63 HumIn GAA KO mice (GAA$^{-/-}$×CD63$^{hu/hu}$) infected with AAVs containing a liver specific enhancer (serpina 1; SEQ ID NO:9) and a liver specific promoter (LSP; TTR; SEQ ID NO:8) driving the expression of an anti-hCD63::GAA multidomain therapeutic (SEQ ID NO:10), which uses a chymotrypsinogen B2 signal peptide (SP7) and contains amino acids 36-952 of human GAA (Δ8GAA) exhibited significant gains in tests of muscle strength and coordination. Three different doses were given for each virus: 5e11 vg/kg, 2e12 vg/kg, and 4e12 vg/kg.

Serum was collected by submandibular bleeds on a regular basis. One month post-AAV infection, mice were sacrificed. Cardiac and skeletal muscle tissue samples were collected and snap frozen in liquid nitrogen and kept at −80° C. for storage. Glycogen in tissues were measured by homogenizing tissues by bead impaction in distilled water. Samples were boiled and centrifuged, and the supernatants were used in a commercial glycogen assay kit. Serum was quantified using western blot with an antibody against human GAA as described in previous examples. For each mouse, the glycogen level in each tissue was plotted against the serum level of the construct at 1 month. 4-parameter curve fits were used to determine the EC50 of the two treatments in each tissue.

Infection with AAVs containing a liver specific promoter (LSP) encoding either anti-hCD63::GAA or sp7-48GAA provided comparable serum levels of GAA at each infection dose. FIG. 11. However, in every muscle tissue assayed, an ~2.2 fold reduction in EC50 was observed when using anti-hCD63::GAA vs. sp7-Δ8GAA, demonstrating that at equivalent serum levels, anti-CD63::GAA clears glycogen more efficiently than a modified GAA expression construct that is not fused to an antibody. See FIG. 12.

Example 9: Glycogen Content in CNS of Murine Pompe Model Post-AAV Treatment with Various GAA Constructs and Doses Two-month-old CD63 HumIn GAA KO mice were administered via tail vein injection with either AAV2/8 virus containing a genome with either the TTR liver specific promoter driving human GAA (AAV-hGAA; described in Example 1) or the TTR liver specific promoter driving anti-human CD63 ScFv fused at its C-terminus with human GAA (AAV-anti-hCD63 ScFv-hGAA; described in Example 1). Both AAV2/8 viruses were delivered at 1e11 vg/mouse. As controls, untreated CD63 HumIn GAA KO (Gaa$^{-/-}$) mice and untreated CD63 HumIn with the mouse GAA gene intact (wildtype mice) were included in the assay. Mice were housed for 9 months after treatment, after which all mice were sacrificed and individual tissues were harvested for glycogen measurements. CNS tissues) were dissected on ice and quickly flash frozen 9 months after AAV transduction. Spinal cord, cerebellum, and hippocampus tissues were homogenized in distilled deionized water using bead impaction, and glycogen was measured in the tissue lysate supernatants using a commercial fluorometric glycogen assay kit (FIG. 13).

In another analogous experiment, knockout mice were treated with AAV constructs encoding GAA (1e11 vg) or anti-CD63ScFv-GAA fusion (doses 1e10 vg, 5e10 vg, or 1e11 vg). Wild-type mice and the amount of stored glycogen per mg of CNS tissue (spinal cord: FIG. 14A; brain: FIG. 14B) was examined 3 months after AAV delivery. Wild-type mice and KO mice (GAA−/−) that were untreated were used as comparators for their stored glycogen levels in CNS tissue for the same duration (3 months).

ScFv-GAA fusion constructs were more effective than GAA alone at reducing stored glycogen levels in diseased mice at a dose of 1e11 vg/mouse (FIGS. 13-14). A dose of 5e10 vg ScFv-GAA fusion provided decreased glycogen storage levels equivalent to the higher dosed GAA alone construct (FIGS. 14A-14B). These levels of reduced glycogen storage were shown to be effective by Hordeaux et al 2017 (e.g. a decrease in glycogen and improved muscle strength in mice injected intrathecally with AAV GAA). The correlative serum level of ScFv-GAA fusion protein is detectable at 5e10 vg and more than 15 ug/mL in the mice receiving 1e11 vg (Table 9).

TABLE 9

Correlation of dose by weight and level of anti-CD63::GAA in the serum.

| Experimental dose (viral genomes/mouse) | Approximate dose by weight (viral genomes/kg) | Level of anti-CD63::GAA in the serum (micrograms/mL) |
|---|---|---|
| 1e10 | 4e11 | undetectable |
| 5e10 | 2e12 | 1.97 +/− 1.18 |
| 1e11 | 4e12 | 15.84 +/− 13.37 |

Without being bound by any one theory, detectable serum levels, e.g., serum levels higher than 1 ug/mL of GAA linked to a delivery domain that crosses the blood-brain-barrier are considered therapeutic.

Example 10: Expression of Multidomain Therapeutic Proteins Comprising at Least Two Delivery Domains CHO cells were transfected with an expression constructs depicted in FIGS. 1C-1G, and expression of each of the constructs was confirmed (data not shown). Additionally, binding of some of the multidomain therapeutic proteins encoded by 4W1 and 4M1 (FIG. 1F) to CD63 was confirmed by ELISA (data not shown).

What is claimed is:

1. A multidomain therapeutic protein comprising a first delivery domain, a second delivery domain, and an enzyme domain, wherein the first delivery domain binds human transferrin receptor (hTfR), and wherein the second delivery domain comprises a single-chain variable fragment (scFv) that binds CD63, wherein the scFv that binds CD63 comprises the sequence set forth in SEQ ID NO: 2.

2. The multidomain therapeutic protein of claim 1, wherein the first delivery domain comprises a single-chain variable fragment (scFv).

3. The multidomain therapeutic protein of claim 2, wherein the first delivery domain scFv or the second delivery domain scFv is fused to an Fc.

4. The multidomain therapeutic protein of claim 3, wherein the Fc comprises a wildtype human IgG4 isotype.

5. The multidomain therapeutic protein of claim 3, wherein GAA is conjugated to the carboxy terminus of the Fc.

6. The multidomain therapeutic protein of claim 1, wherein the first delivery domain comprises a half-body.

7. The multidomain therapeutic protein of claim 1, wherein the enzyme domain is alpha-glucosidase (GAA).

8. The multidomain therapeutic protein of claim 1, wherein the multidomain therapeutic protein comprises the sequence set forth in SEQ ID NO: 10.

9. The multidomain therapeutic protein of claim 8, comprising an anti-hTfR scFv and an anti-hCD63 scFv, wherein the anti-hTfR scFv and anti-hCD63 scFv are both linked, at their carboxy termini, to a single GAA enzyme.

10. The multidomain therapeutic protein of claim 1, wherein the first delivery domain is an anti-hTfR scFv, and the enzyme domain is linked to carboxy terminus of the VL domain of the anti-hTfR scFv.

11. The multidomain therapeutic protein of claim 10, wherein the second delivery domain is linked to the N-terminus of the VH domain of the anti-hTfR scFv.

12. The multidomain therapeutic protein of claim 1, wherein the enzyme domain comprises the amino acid sequence set forth in SEQ ID NO: 1.

13. A polynucleotide encoding the multidomain therapeutic protein of claim 1.

14. The polynucleotide of claim 13, further comprising a virus nucleic acid sequence.

15. The polynucleotide of claim 14, wherein the virus nucleic acid sequence is an adeno-associated virus (AAV) nucleic acid sequence.

16. The polynucleotide of claim 13, further comprising a virus nucleic acid sequence and a locus-targeting nucleic acid sequence, wherein the virus nucleic acid sequence is an adeno-associated virus (AAV) nucleic acid sequence.

17. The polynucleotide of claim 13, further comprising a tissue specific regulatory element that is a liver specific promoter or a neuronal specific promoter.

18. The polynucleotide of claim 17, wherein the tissue specific regulatory element comprises the sequence set forth in SEQ ID NO:8 and/or SEQ ID NO:9.

19. A gene therapy vector comprising a polynucleotide of claim 13.

20. The gene therapy vector of claim 19, wherein the gene therapy vector is selected from the group consisting of:
 a viral vector;
 a naked polynucleotide; and
 a polynucleotide complex that is a lipid nanoparticle comprising the polynucleotide and lipids.

21. The gene therapy vector of claim 20, wherein the gene therapy vector is an AAV9, an Anc80, an AAV2/8 chimera, or an AAV pseudotyped to the liver or neuronal tissue.

22. The gene therapy vector of claim 19, wherein the gene therapy vector is a viral vector selected from the group consisting of a retrovirus, an adenovirus, a herpes simplex virus, a pox virus, a vaccinia virus, a lentivirus, and an adeno-associated virus.

23. A method of delivering a therapeutic protein to the central nervous system (CNS) of a patient, comprising delivering the polynucleotide of claim 13 encoding the multidomain therapeutic protein to the liver of the patient to form a liver depot for the production and secretion of the multidomain therapeutic at a consistent serum level of at least 1 g/mL over consecutive days, weeks or months following delivery to provide a therapeutically effective amount of the multidomain therapeutic protein in the CNS.

* * * * *

UNITED STATES PATENT AND TRADEMARK OFFICE
CERTIFICATE OF CORRECTION

PATENT NO. : 12,258,597 B2
APPLICATION NO. : 16/968452
DATED : March 25, 2025
INVENTOR(S) : Andrew Baik et al.

Page 1 of 1

It is certified that error appears in the above-identified patent and that said Letters Patent is hereby corrected as shown below:

In the Claims

In Column 94, Line 48, delete "1 g/mL" and insert -- 1 µg/mL --

Signed and Sealed this
Third Day of June, 2025

Coke Morgan Stewart
*Acting Director of the United States Patent and Trademark Office*